United States Patent
Andersen et al.

(10) Patent No.: US 12,173,313 B2
(45) Date of Patent: Dec. 24, 2024

(54) ASSEMBLY OF FUNCTIONALLY INTEGRATED HUMAN FOREBRAIN SPHEROIDS AND METHODS OF USE THEREOF

(71) Applicant: The Board of Trustees of the Leland Stanford Junior University, Stanford, CA (US)

(72) Inventors: Jimena Andersen, Palo Alto, CA (US); Fikri Birey, Palo Alto, CA (US); Sergiu P. Pasca, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 122 days.

(21) Appl. No.: 17/671,430

(22) Filed: Feb. 14, 2022

(65) Prior Publication Data
US 2022/0169983 A1    Jun. 2, 2022

Related U.S. Application Data

(62) Division of application No. 16/884,980, filed on May 27, 2020, now Pat. No. 11,279,914, which is a division of application No. 15/938,564, filed on Mar. 28, 2018, now Pat. No. 10,676,715.

(60) Provisional application No. 62/477,858, filed on Mar. 28, 2017.

(51) Int. Cl.
| | |
|---|---|
| *C12N 5/079* | (2010.01) |
| *C12N 5/00* | (2006.01) |
| *C12N 5/074* | (2010.01) |
| *C12N 5/0793* | (2010.01) |
| *C12N 5/0797* | (2010.01) |
| *C12N 5/10* | (2006.01) |
| *G01N 33/50* | (2006.01) |

(52) U.S. Cl.
CPC ......... *C12N 5/0622* (2013.01); *C12N 5/0619* (2013.01); *C12N 5/0623* (2013.01); *C12N 5/0696* (2013.01); *C12N 5/10* (2013.01); *G01N 33/5058* (2013.01); *C12N 5/0012* (2013.01); *C12N 5/0062* (2013.01); *C12N 2501/01* (2013.01); *C12N 2501/11* (2013.01); *C12N 2501/115* (2013.01); *C12N 2501/13* (2013.01); *C12N 2501/15* (2013.01); *C12N 2501/155* (2013.01); *C12N 2501/385* (2013.01); *C12N 2506/45* (2013.01); *G01N 2333/70571* (2013.01)

(58) Field of Classification Search
CPC .. C12N 5/0622; C12N 5/0619; C12N 5/0623; C12N 5/0696; C12N 5/10; C12N 5/0012; C12N 5/0062; C12N 2501/01; C12N 2501/11; C12N 2501/115; C12N 2501/13; C12N 2501/15; C12N 2501/155; C12N 2501/385; C12N 2506/45; C12N 2501/727; C12N 2502/088; C12N 5/0697; C12N 2501/415; G01N 33/5058; G01N 2333/70571

See application file for complete search history.

(56) References Cited

U.S. PATENT DOCUMENTS

| | | |
|---|---|---|
| 2016/0059203 A1 | 3/2016 | Petcavich |
| 2017/0002324 A1 | 1/2017 | Petcavich |
| 2017/0166857 A1 | 6/2017 | Petcavich |
| 2017/0322194 A1 | 11/2017 | Petcavich |
| 2018/0113118 A1 | 4/2018 | Petcavich |

FOREIGN PATENT DOCUMENTS

| | | |
|---|---|---|
| EP | 2028268 | 2/2009 |
| WO | WO2009024448 | 2/2009 |

OTHER PUBLICATIONS

Darville et al., EBioMedicine 9, (2016) 293-305 (Year: 2016).*
Bell et al., Stem Cell Reports vol. 11:183-196, Jul. 10, 2018 (Year: 2019).*
Noelanders et al., The Neuroscientist, 23(3):314-329, first published online Sep. 13, 2016 (Year: 2016).*
Powell et al. J Neurosci, 23(2):622-631, Jan. 15, 2003 (Year: 2003).*
Ziliotto et al., Frontiers in Neurol., vol. 10, Sec. Multiple Sclerosis and Neuroimmunology, Apr. 24, 2019 (Year: 2019).*
Bagley et al., "Fused dorsal-ventral cerebral organoids model complex interactions between diverse brain regions", Nature, Jul. 2017, pp. 743-751, vol. 14, No. 7, Macmillan Publishers Limited, Basingstoke, United Kingdom.
Huangfu et al., "Induction of pluripotent stem cells from primary human fibroblasts with only Oct4 and Sox2", Nature Biotechnology, Nov. 2008, pp. 1269-1275, vol. 26, No. 11, Nature Publishing, London, United Kingdom.
Kim et al., "Generation of human induced pluripotent stem cells by direct delivery of reprogramming proteins", Cell Stem Cell, Jun. 5, 2009, pp. 472-476, vol. 4, Issue 6, Elsevier Inc., Amsterdam, Netherlands.
Lancaster et al., "Cerebral organoids model human brain development and microcephaly", Nature, Aug. 28, 2013, pp. 373-379, vol. 501, No. 7467, Macmillan Publishers Limited, Basingstoke, United Kingdom.

(Continued)

*Primary Examiner* — Kimberly Ballard
*Assistant Examiner* — Stacey N MacFarlane
(74) *Attorney, Agent, or Firm* — Bozicevic, Field & Francis LLP; Andrew R. Guzman; Pamela J. Sherwood

(57) ABSTRACT

Human pluripotent stem cells are differentiated in vitro into forebrain subdomain structures, which are then fused to generate an integrated system for use in analysis, screening programs, and the like.

2 Claims, 15 Drawing Sheets
Specification includes a Sequence Listing.

(56) References Cited

OTHER PUBLICATIONS

Li et al., "Generation of rat and human induced pluripotent stem cells by combining genetic reprogramming and chemical inhibitors", Cell Stem Cell, , Jan. 9, 2009, pp. 16-19, 4, Elsevier Inc., Amsterdam, Netherlands.

Park et al., "Reprogramming of human somatic cells to pluripotency with defined factors", Nature, Jan. 10, 2008, pp. 141-146, 451, Nature Publishing, London, United Kingdom.

Pasca et al., "Functional cortical neurons and astrocytes from human pluripotent stem cells in 3D culture", Nature, ds. May 25, 2015, pp. 671-678, vol. 12, No. 7, Macmillan Publishers Limited, Basingstoke, United Kingdom.

Qian et al., "Brain-Region-Specific Organoids Using Minibloreactors for Modeling ZIKV Exposure", Cell, May 19, 2016, pp. 1238-1254. vol. 165, No. 5, Elsevier, New York City, NY.

Soldner et al., "Parkinson's disease patient-derived induced pluripotent stem cells free of viral reprogramming factors", Cell, Mar. 6, 2009, pp. 964-977, vol. 136, Issue 5, Elsevier Inc., Amsterdam, Netherlands.

Takahashi et al., "Induction of Pluripotent Stem Cells from Adult Human Fibroblasts by Defined Factors", Cell, Nov. 30, 2007, pp. 861-872, vol. 131, Issue 5, Elsevier Inc., Amsterdam, Netherlands.

Yu et al., "Induced Pluripotent Stem Cell Lines Derived from Human Somatic Cells", Science, Dec. 21, 2007, pp. 1917-1920, vol. 318, Issue 5858, American Association for the Advancement of Science, Washington, D.C.

Birey et al: "Assembly of functionally integrated human forebrain spheroids". Nature. vol. 545. No. 7652.May 4, 2017, pp. 54-59.

Sloan et al. "Generation and assembly of human brain region-specific three-dimensional cultures". Nature Protocols. Nature Publishing Group, vol. 13. No. 9, Sep. 10, 2018, pp. 2062-2085.

Gage et al. "Neural Stem Cells: Generating and Regenerating the Brain" Neuron. vol 80. No. 3, Oct. 1, 2013 (Oct. 1, 2013). pp. 588-601.

Quadrato et al. "Present and future of modeling human brain development in 3D organoids" Current Opinion in Cell Biology, Jan. 1, 2017, pp. 47-52.

\* cited by examiner

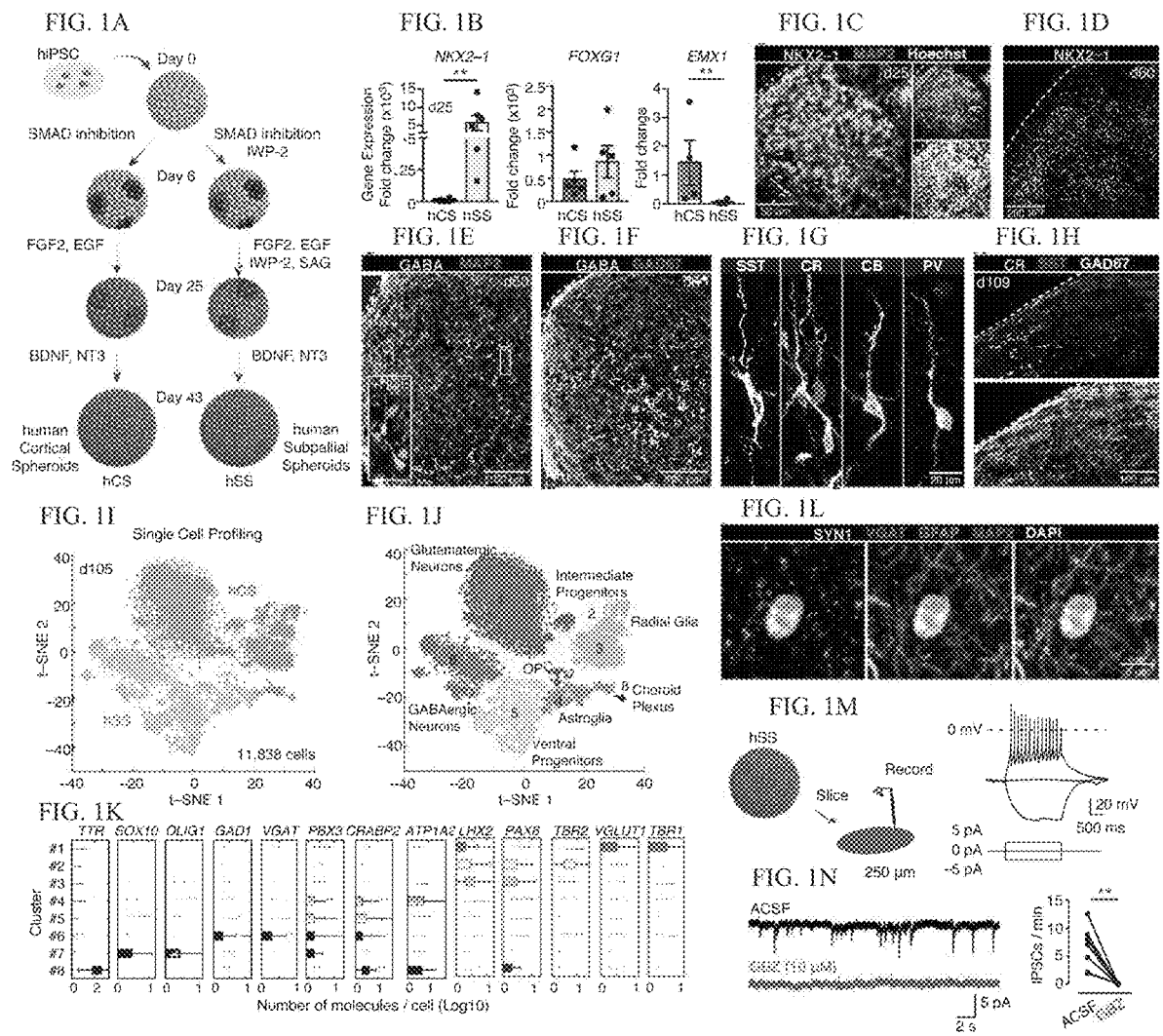

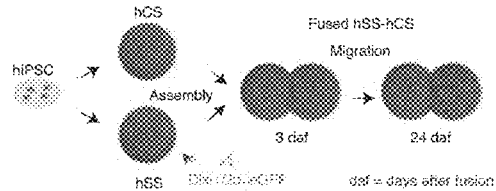
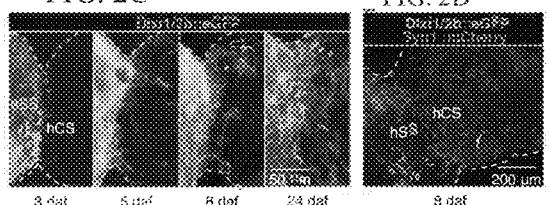
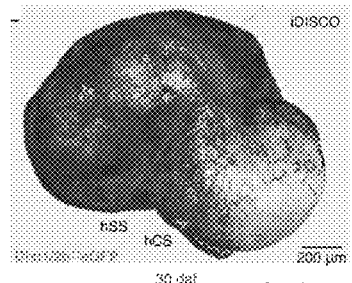
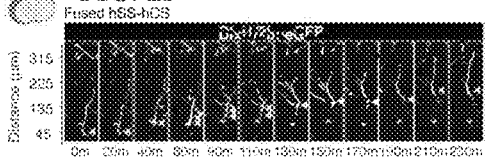
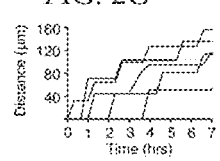
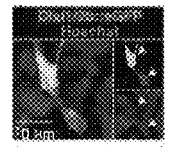
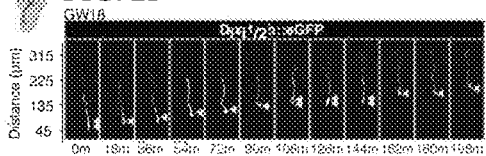
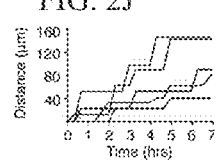
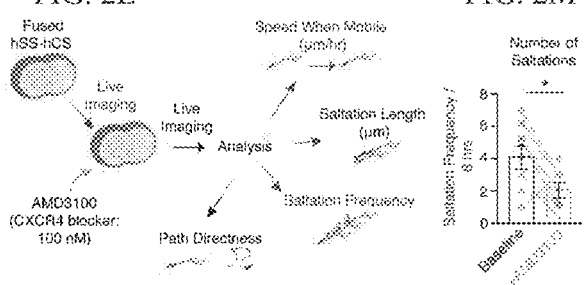
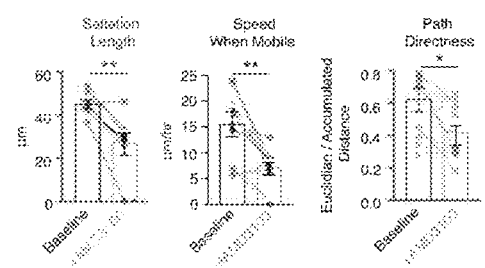

FIG. 3A  FIG. 3B  FIG. 3C
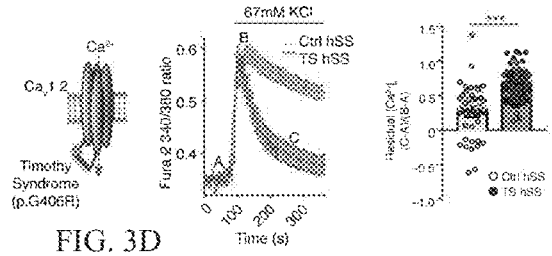
FIG. 3D
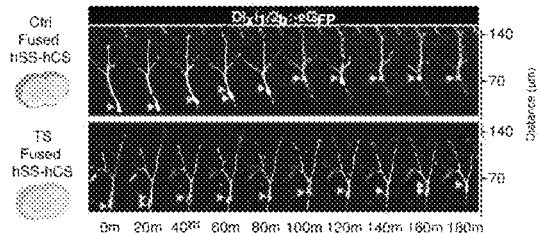
FIG. 3E  FIG. 3F  FIG. 3G
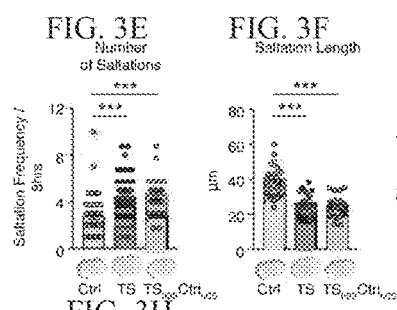
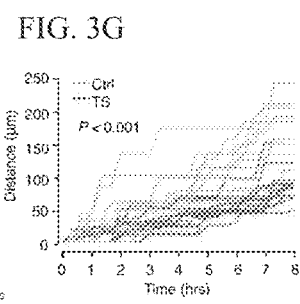
FIG. 3H  FIG. 3I
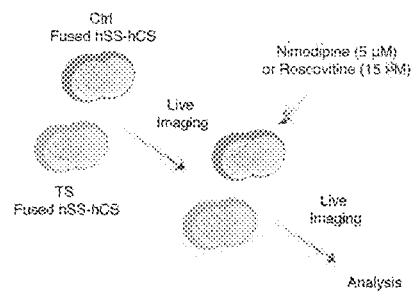
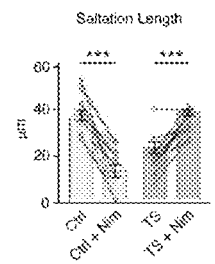

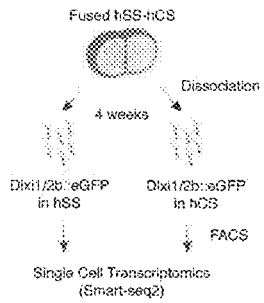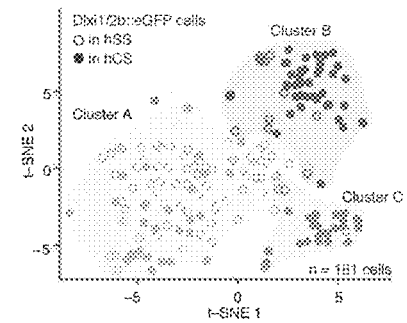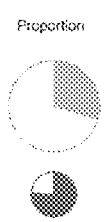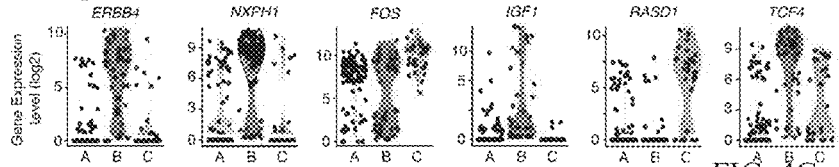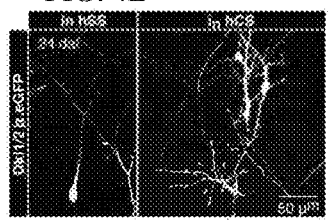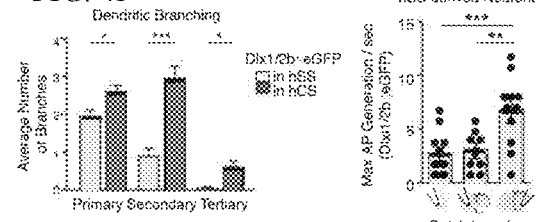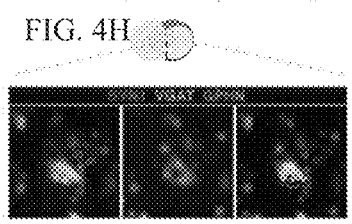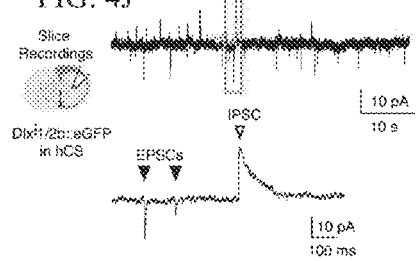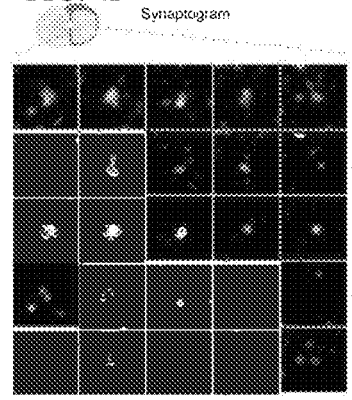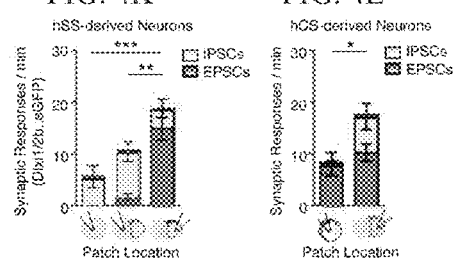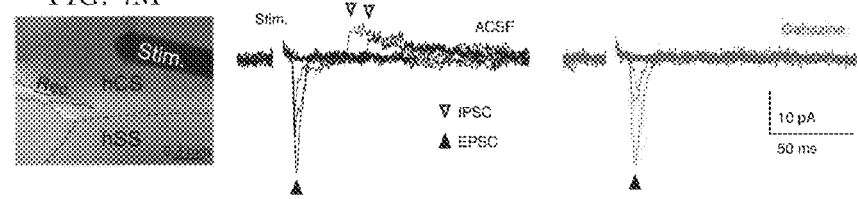

FIG. 8A
FIG. 8B
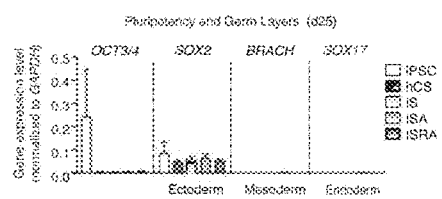
FIG. 8C
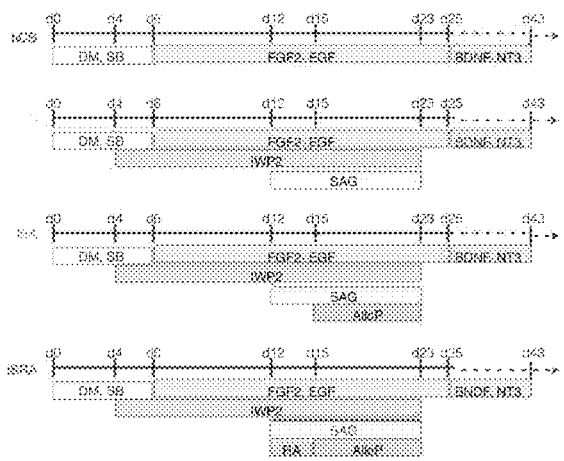
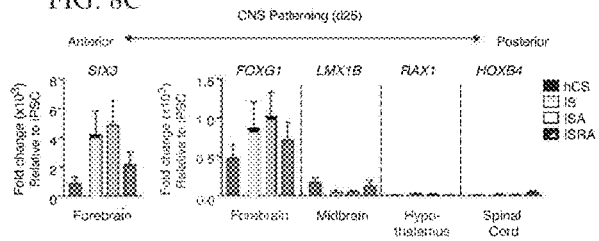
FIG. 8D
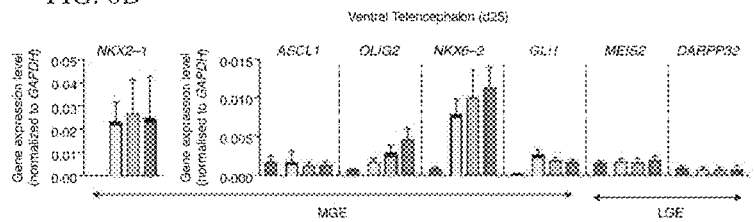
FIG. 8E
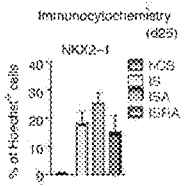
FIG. 8F
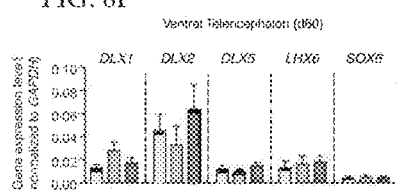
FIG. 8G
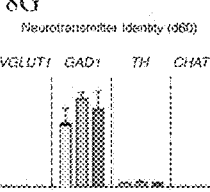
FIG. 8H
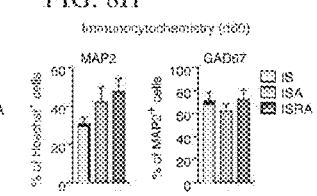
FIG. 8I
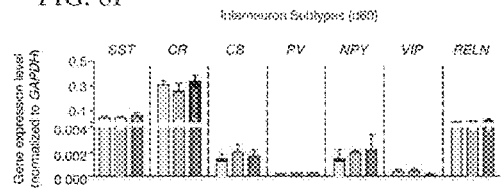
FIG. 8J
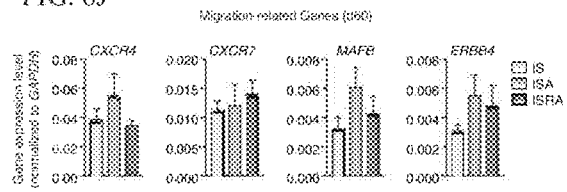

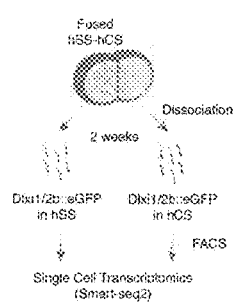
FIG. 11A
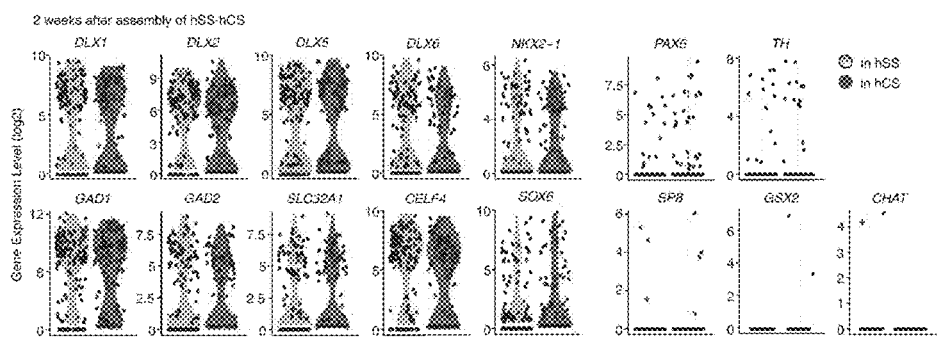
FIG. 11B
FIG. 11C
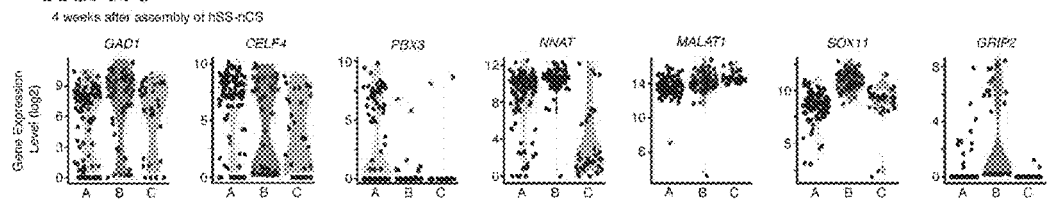
FIG. 11D
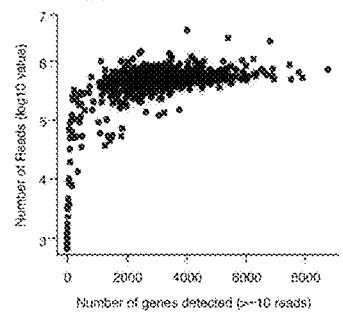
FIG. 11E
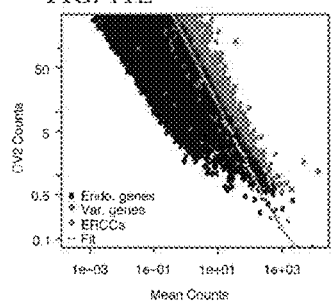

FIG. 13A
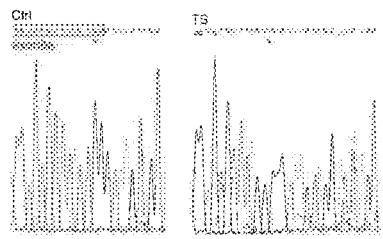
FIG. 13B
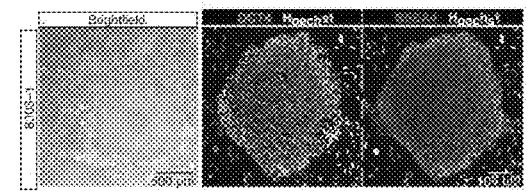
FIG. 13C
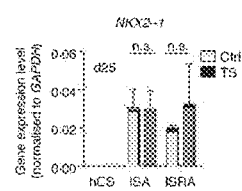
FIG. 13D
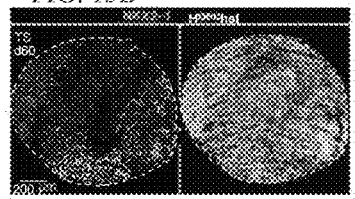
FIG. 13E
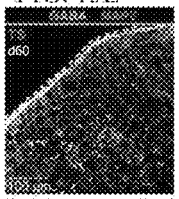
FIG. 13F
FIG. 13G
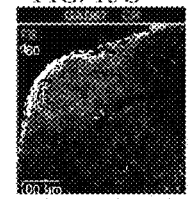
FIG. 13H
FIG. 13I
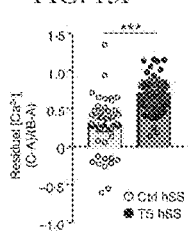
FIG. 13J
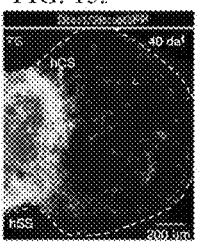
FIG. 13K
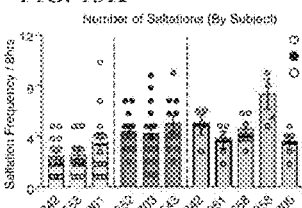
FIG. 13L
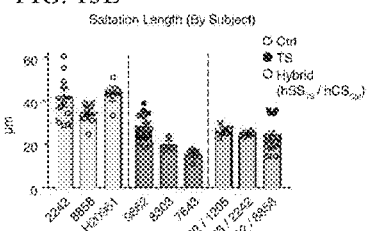
FIG. 13M
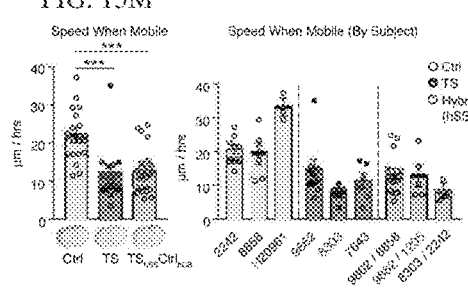
FIG. 13N
FIG. 13O
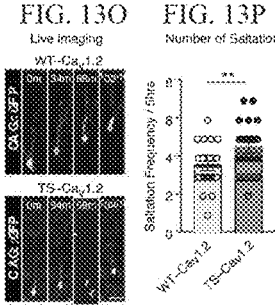
FIG. 13P
FIG. 13Q
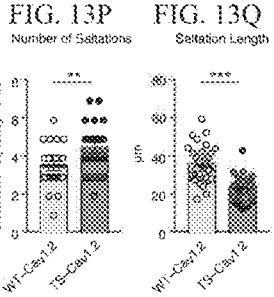
FIG. 13R
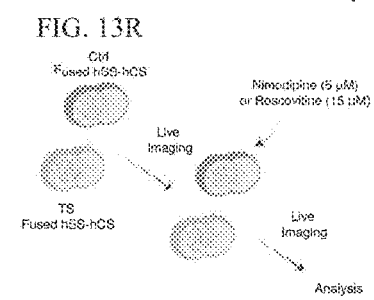
FIG. 13S
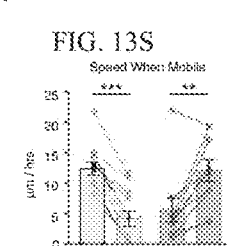
FIG. 13T
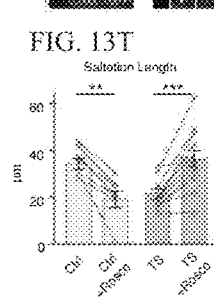
FIG. 13U
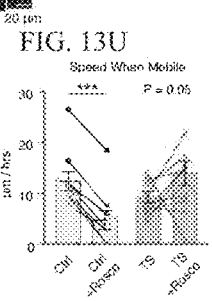

ASSEMBLY OF FUNCTIONALLY INTEGRATED HUMAN FOREBRAIN SPHEROIDS AND METHODS OF USE THEREOF

CROSS REFERENCE

This application claims benefit and is a Divisional of application Ser. No. 16/884,980, filed May 27, 2020, which claims benefit of application Ser. No. 15/938,564 filed Mar. 28, 2018, which claims benefit of U.S. Provisional Patent Application No. 62/477,858, filed Mar. 28, 2017, which application is incorporated herein by reference in its entirety.

FEDERALLY SPONSORED RESEARCH AND DEVELOPMENT

This invention was made with Government support under contract MH107800 awarded by the National Institutes of Health. The Government has certain rights in the invention.

BACKGROUND OF THE INVENTION

Progress in understanding the intricate development of the human central nervous system and elucidating the mechanisms of neuropsychiatric disorders in patients has been greatly limited by restricted access to functional human brain tissue. While studies in rodents and other mammals have provided important insights into the fundamental principles of neural development, we know little about the cellular and molecular processes responsible for the massive expansion of the forebrain in primates, nor many of its human specific features. In recent years, a paradigm shift has been achieved in the field with the introduction of cellular reprogramming—a process during which terminally differentiated somatic cells can be converted into pluripotent stem cells, named human induced pluripotent stem cells (hiPSC). These hiPSCs can be generated from any individual and, importantly, can be directed to differentiate in vitro into all germ layer derivatives, including neural cells.

While the methods and efficiency of generating hiPSCs have been significantly improved and standardized across laboratories, the methods for deriving specific neuronal cell types and glial cells remain challenging. Over the past decade, improvements in neural specification and differentiation protocols of pluripotent stem cells in monolayer have led to the generation of a variety of cell types. Nonetheless, two-dimensional (2D) methods are unlikely to recapitulate the cyto-architecture of the developing three-dimensional (3D) nervous system or the complexity and functionality of in vivo neural networks and circuits. Moreover, these methods are laborious, costly, have limited efficiency, give rise to relatively immature neurons and incompatible with long-term culturing of neurons.

Pharmaceutical drug discovery utilizes the identification and validation of therapeutic targets, as well as the identification and optimization of lead compounds. The explosion in numbers of potential new targets and chemical entities resulting from genomics and combinatorial chemistry approaches over the past few years has placed massive pressure on screening programs. The rewards for identification of a useful drug are enormous, but the percentages of hits from any screening program are generally very low. Desirable compound screening methods solve this problem by both allowing for a high-throughput so that many individual compounds can be tested; and by providing biologically relevant information so that there is a good correlation between the information generated by the screening assay and the pharmaceutical effectiveness of the compound.

Some of the more important features for pharmaceutical effectiveness are specificity for the targeted cell or disease, a lack of toxicity at relevant dosages, and specific activity of the compound against its molecular target. Therefore, one would like to have a method for screening compounds or libraries of compounds that allows simultaneous evaluation for the effect of a compound on the biologically relevant cell population, where the assay predicts clinical effectiveness.

The effect of drugs on specific human neural or glial cell types is of particular interest, where efficacy and toxicity may rest in sophisticated analysis of cell migration, activity, or the ability of neurons to form functional networks, rather than on simple viability assays. The discrepancy between the number of lead compounds in clinical development and approved drugs may partially be a result of the methods used to generate the leads and highlights the need for new technology to obtain more detailed and physiologically relevant information on cellular processes in normal and diseased states.

A number of important clinical conditions are associated with altered neuronal or glial function, including neurodegenerative disorders (Alzheimer's disease (AD), Parkinson's disease (PD), Huntington's disease (HD), and amyotrophic lateral sclerosis (ALS), or psychiatric conditions such as schizophrenia and other psychoses, bipolar disorders, mood disorders, intellectual disability (ID) or autism spectrum disorders (ASD).

In addition to pharmaceutical drug discovery, there is a pressing need for meaningful screening platforms to identify and explore specific toxicity effects due to the increasing number of new therapeutic compounds and chemical substances with human exposure. Particularly, in the field of neurotoxicity, assays capable of assessing the impairment of neuronal or glial function are still lacking for human cells.

Therefore, the development of in vitro screening platforms that recapitulate highly functional human tissue is of utmost importance.

Publications. Methods to reprogram primate somatic cells to a pluripotent state include differentiated somatic cell nuclear transfer, differentiated somatic cell fusion with pluripotent stem cells and direct reprogramming to produce induced pluripotent stem cells (iPS cells) (Takahashi K, et al. (2007) Cell 131:861-872; Park I H, et al. (2008) Nature 451:141-146; Yu J, et al. (2007) Science 318:1917-1920; Kim D, et al. (2009) Cell Stem Cell 4:472-476; Soldner F, et al. (2009) Cell. 136:964-977; Huangfu D, et al. (2008) Nature Biotechnology 26:1269-1275; Li W, et al. (2009) Cell Stem Cell 4:16-19).

SUMMARY OF THE INVENTION

Compositions and methods are provided for in vitro generation of a human 3D microphysiological system (MPS) that comprises functionally-integrated excitatory glutamatergic and GABAergic neurons. This system is generated by the directed differentiation of subdomains of the forebrain that functionally interact in development. Subdomains are then assembled (fused) into a functionally integrated forebrain spheroid. The system captures in vitro processes typical of in vivo central nervous system (CNS) development that could not otherwise be modeled with conventional 2D cultures, including the saltatory migration of interneurons on their way to the cerebral cortex. After migrating into an active neural network, interneurons mature and integrate into a synaptically connected microphysiological system without the requirement of seeding onto rodent cortical cultures or brain slice cultures. Assembling networks using this modular system allows the study of excitation to inhibition interplay during cortical development in normal and disease states. More importantly, this system illustrates a novel concept for deriving and then assembling developmentally and disease relevant human brain regions from pluripotent stem cells (hESC, hiPSC) with the goal of capturing novel, emerging features of the CNS and to enable mechanistic and therapeutic studies of these processes in vitro. For instance, one could assemble human cortico-cortical spheroids to mimic interhemispheric axonal guidance and communication, but also cortico-striatal spheroids, striato-nigral, cortico-spinal, etc.

In one embodiment, methods are provided for the generation of a human 3D microphysiological (MPS) forebrain system. The methods comprise an initial step of differentiating pluripotent cells (hPSC) into the forebrain subdomains of (i) a ventral forebrain structure, referred to herein as a subpallial spheroid (hSS) comprising primarily GABAergic cortical interneurons; and (ii) a cerebral cortical, or dorsal pallium structure (hCS) comprising cortical gluamatergic neurons of various layers. These neural spheroids may also comprise neural progenitor cells, astrocytes, oligodendrocytes, neurons and the like. Following this differentiation step, subpallial spheroid(s) (hSS) and cortical spheroid(s) (hCS) are placed adjacent to each other in culture under conditions permissive for fusion of the two spheroids and generation of the integrated forebrain system. One or both of the spheroids may comprise cells detectably labeled with, for example, a fluorescent or luminescent expressed protein marker. During the fusion process, the saltatory migration of neurons from hSS to hCS can be observed. The fused forebrain comprises functionally integrated cortical neurons of excitatory and inhibitory types, which provides a platform for analysis of the effect of agents on brain structure and function. The validity of this platform has been assessed by performed live imaging of Dlxi1/2b::eGFP-labeled cells in human forebrain tissue at gestational weeks 18 and 20. More specifically, it was observed that the average saltation length in fetal forebrain tissue was 43.54 µm±2.39 and very similar to the 38.17 µm±1.33 saltation length observed in fused hSS-hCS. Similarly, the average frequency of saltation per 8 hours was 3.08±0.18 in human fetal tissue versus 2.9±0.25 saltations in fused hSS-hCS. Taken together, these data suggests that this platform recapitulates with great accuracy the migration pattern of human cortical interneurons in the developing forebrain. Live imaging data and 3D reconstructions with optical clearing methods of fused (assembled) hSS-hCS indicate that interneurons migrating close to the surface of hCS and often encounter layer 1 neurons (RELN$^+$, TBR1$^+$), which are positioned on the surface of hCS, reminiscent of a marginal zone-like migration. At the same time, interneurons at the hSS-hCS interface often penetrate and encounter cortical glutamatergic neurons, which are primarily deep-layer cortical neurons at this in vitro developmental stage of hCS. This deeper migration also makes possible for some of these interneurons to get closer to pallial proliferative zones and undergo ventricular-directed migration.

In some embodiments, methods are provided for determining the activity of a candidate agent on human cells present in the integrated forebrain system or isolated from the integrated forebrain system, the method comprising contacting the candidate agent with one or a panel of integrated forebrain system or purified cells derived therefrom. The cell populations optionally comprise at least one allele encoding a mutation associated or potentially with a neuropsychiatric disease; and determining the effect of the agent on morphological, genetic or functional parameters, including without limitation gene expression profiling. Methods of analysis at the single cell level are also of interest, e.g. migration assays, axonal growth and pathfinding assays, atomic force microscopy, super resolution microcopy, light-sheet microscopy, two-photon microscopy, patch clamping, single cell gene expression (RNA-seq), calcium imaging with pharmacological screens, modulation of synaptogenesis, and the like.

In some embodiments, one or more such integrated forebrain systems are provided, including without limitation a panel of such in vitro derived integrated forebrain systems are provided, where the panel includes two or more genetically different cells. In some embodiments a panel of such integrated forebrain systems are provided, where the systems can be subjected to a plurality of candidate agents, or a plurality of doses of a candidate agent. Candidate agents include small molecules, i.e. drugs, genetic constructs that increase or decrease expression of an RNA of interest, infectious agents, electrical changes, and the like. In some embodiments a panel refers to a system or method utilizing patient-specific systems from two or more distinct conditions, and may be three or more, four or more, five or more, six or more, seven or more genetically distinct conditions. In one embodiment, methods are provided for generating human subpallial spheroids (hSS) and cells comprised therein, including, for example neural progenitors and GABAergic interneurons. A feature of the invention is the ability to generate these cells, and systems comprising such cells, from patient samples, allowing disease-relevant generation and screening of the cells for therapeutic drugs and treatment regimens, where the methods utilize in vitro cell cultures or animal models derived therefrom for such purposes. The methods utilize induced human pluripotent stem cells (hiPSCs), which may be obtained from patient or carrier cell samples, e.g. adipocytes, fibroblasts, keratinocytes, blood cells and the like. The hiPSCs are instructed to develop a neural fate in vitro, and then specified into human subpallial spheroids (hSS). The cell populations can be isolated from the hSS, the intact hSS can be used as a model for interacting neural cell populations, or fused to an hCS as a model for more complex neural interactions. The hSS and cells derived therefrom may be used for transplantation in mammals and other species, for experimental evaluation including screening of drugs and biological entities, as a source of lineage and cell specific products, and the like. In some embodiments the cell cultures are feeder-free and xeno-free. In some embodiments of the invention, populations of purified human cells from the spheroids (hCS, hSS), e.g. GABAergic interneurons and progenitors thereof, etc. are provided, where the cells are differentiated from induced human pluripotent stem cells (hiPSCs). In some embodiments the spheroids find use in analyzing cell-autonomous or region-autonomous phenotypes in disease states. Various combinations of assemblies can be generated, for example a cortical spheroid generated from control-derived (normal) hiPSCs can be assembled with a subpallium spheroids generated from patient-derived (disease state) hiPSCs and the like.

After differentiation in hSSs or integrated forebrain system, individual cell types of interest can be isolated for various purposes. The cells are harvested at an appropriate stage of development, which may be determined based on the expression of markers and phenotypic characteristics of the desired cell type. Cultures may be empirically tested by immunostaining for the presence of the markers of interest, by morphological determination, etc. The cells are optionally enriched before or after the positive selection step by drug selection, panning, density gradient centrifugation, flow cytometry etc. In another embodiment, a negative selection is performed, where the selection is based on expression of one or more of markers found on hESCs, fibroblasts, neural cells, epithelial cells, and the like. Selection may utilize panning methods, magnetic particle selection, particle sorter selection, fluorescent activated cell sorting (FACS) and the like.

Various somatic cells find use as a source of hiPSCs; of particular interest are adipose-derived stem cells, fibroblasts, and the like. The use of hiPSCs from individuals of varying genotypes, particularly genotypes potentially associated with neurologic and psychiatric disorders or even idiopathic forms of neuropsychiatric disease (autism spectrum disorders, psychosis, etc) are of particular interest. The hiPSCs are dissociated and grown in suspension; then induced to a neural fate by inhibition of BMP and ROCK pathways. The spheroids are then moved to neural medium in the presence of FGF2 and EGF. To generate the hSS, the medium further comprises modulators of Wnt and sonic hedgehog (SHH) signaling pathways, and may optionally also comprise one or both of allopregnanolone and transient exposure to retinoic acid. The spheroids are then changed to medium comprising the growth factors BDNF and NT3. After such culture, the spheroids can be maintained for extended periods of time in neural medium in the absence of growth factors, e.g. for periods of 1, 2, 3, 4, 5, 6, 7, 8, 9, 10, 11, 12, 24, 36 months or longer.

These and other objects, advantages, and features of the invention will become apparent to those persons skilled in the art upon reading the details of the subject methods and compositions as more fully described below.

BRIEF DESCRIPTION OF THE DRAWINGS

FIG. 1A-1N. Characterization of hSS derived from hiPSC. (FIG. 1A) Scheme illustrating the main stages for the generation of hCS and hSS from hiPSC. (FIG. 1B) Fold changes in gene expression (relative to expression in hiPSC and normalized to GAPDH) of NKX2-1 (n=6 hiPSC lines; Mann-Whitney test, P=0.002), FOXG1 (n=5 hiPSC lines; t-test, P=0.35) and EMX1 (n=4 hiPSC lines; Mann-Whitney test, P=0.02) in hCS and hSS at day 25. (FIG. 1C, 1D) Immunostaining for NKX2-1 in cryosections of hSS at day 25 and day 60 of differentiation. (FIG. 1E, 1F) Immunostaining in cryosections of hSS showing expression of GABA and GAD67 and the neuronal marker MAP2 (day 60 of differentiation). (FIG. 1G, 1H) Examples of immunostaining showing cells expressing the GABAergic subtype markers somatostatin (SST), calretinin (CR), calbindin (CB) at day 60 and day 109, and parvalbumin (PV) at day 209. (FIG. 1*l*) t-SNE visualization of single cell gene expression in hCS (magenta) and hSS (green) at day 105 of differentiation (n=11,838 cells; BDTM Resolve system). (FIG. 1J, 1K) Main single cell clusters and boxplots for genes enriched in each cluster (expression of the top 25 genes in each cluster is shown in FIG. 6*d-k*. (FIG. 1L) Volume rendering by array tomography of the interior of a hSS (19.4×18.4×2.9 μm) showing expression of the neuronal marker MAP2 (red), the glial marker GFAP (cyan), and the synaptic proteins SYN1 (green) and VGAT (magenta) (DAPI shown in white). (FIG. 1M) Scheme illustrating patch clamping in sliced hSS and a representative trace of whole-cell current-clamp recording. (FIG. 1N) Representative traces and quantification of spontaneous IPSCs recorded before (black) and during (blue) application of Gabazine (GBZ, 10 μM) in an acute slice preparation of hSS (paired t-test, **P=0.004). Representative traces of EPSCs recorded from hCS are shown in FIG. 9*a*.

FIG. 2A-2P. Cell migration in fused hSS-hCS. (FIG. 2A) Scheme illustrating the assembly of hCS and hSS. Cells in hSS are labeled with Dlxi1/2b::eGFP prior to fusion. (FIG. 2B) Morphology of hCS and hSS before and after assembly. (FIG. 2C) Time-lapse of migration of representative Dlxi1/2b::eGFP+ cells from hSS into hCS over 24 days. (FIG. 2D) Representative example showing the assembly of a fluorescently labeled hCS (AAV-hSyn1::mCherry) and a fluorescently labeled hSS (*Lenti*-Dlxi1/2b::eGFP) after 8 days. (FIG. 2E) 3D reconstruction of an iDISCO-cleared hSS-hCS at 24 days after fusion. (FIG. 2F) Representative example of time-lapse live imaging showing the saltatory migration of Dlxi1/2b::eGFP+ cells in fused hSS-hCS. Yellow arrowheads indicate soma and nucleokinesis. (FIG. 2G) Cumulative plot showing the saltatory migration and pausing of representative Dlxi1/2b::eGFP+ cells in fused hSS-hCS (n=5 cells). (FIG. 2H) Representative immunostaining showing a Dlxi1/2b::eGFP+ cell undergoing nucleokinesis. Yellow arrowheads indicate the cell soma. (FIG. 2I) Representative example of time-lapse live imaging showing the saltatory migration of Dlxi1/2b::eGFP+ cells in human fetal forebrain (GW18). Yellow arrowheads indicate soma and nucleokinesis. (FIG. 2J) Cumulative plot showing the saltatory migration and pausing of representative Dlxi1/2b::eGFP+ cells in human fetal forebrain (n=5 cells). (FIG. 2K) Representative immunostaining showing a Dlxi1/2b::eGFP+ cell undergoing nucleokinesis in slices of human fetal forebrain at GW18. Yellow arrowheads indicate the cell soma. (FIG. 2L) Scheme illustrating the pharmacological manipulation of Dlxi1/2b::eGFP+ cells migrating in hSS-hCS. (FIG. 2M, 2N, 2O, 2P) Quantification of Dlxi1/2b::eGFP+ cell migration before and after exposure to 100 nM of the CXCR4 antagonist AMD3100 (n=8 cells from 2 hiPSC lines; paired t-tests, *P=0.03 for number of saltations, P=0.006 for saltation length, P=0.006 for speed when mobile, *P=0.02 for path directness). Tracking of the migration path of individual Dlxi1/2b::eGFP+ cells is shown in FIG. 10*t*.

FIG. 3A-3I. Modeling of interneuron migration in hSS-hCS derived from Timothy syndrome. (FIG. 3A) Scheme depicting the L-type calcium channel (LTCC) Cav1.2 and the p.G406R gain-of-function mutation (blue star) that causes TS. (FIG. 3B) Calcium imaging (Fura-2) in dissociated hSS derived from TS subjects and controls (Ctrl: n=38 cells from 2 subjects; TS: n=68 cells from 2 subjects). (FIG. 3C) Quantification of residual intracellular calcium ([Ca2+]i) following depolarization of Ctrl and TS cells in hSS. Residual intracellular calcium was calculated by dividing the plateau calcium (C–A) level by the peak calcium elevation (B–A); (t-test, ***P<0.0001). Residual intracellular calcium in Ctrl and TS hCS cells is shown in FIG. 13*h*. (FIG. 3D) Time-lapse of migration of representative Dlxi1/2b::eGFP+ cells in TS and control hSS-hCS. Yellow arrowheads indicate soma and nucleokinesis. A representative image of fused hCS-hSS shown in FIG. 13*i*. (FIG. 3E, 3F) Quantification of the number of saltations (Ctrl: n=48 cells from 3 hiPSC lines from 3 subjects; TS: n=51 cells from 3 hiPSC lines from 3 subjects; TS-Ctrl hybrid: n=24 cells from 5 hiPSC line combinations), and saltation length (Ctrl: n=21 cells from 3 hiPSC lines from 3 subjects; TS: n=29 cells from 3 hiPSC from 3 subjects; TS-Ctrl hybrid: n=12 cells from 3 hiPSC line combinations); one-way ANOVA with Dunnett's multiple comparison test (***, P<0.001). Averages for individual hiPSC lines are shown in FIG. 13*j-l*. (FIG. 3G) Cumulative plot showing migration of TS and control Dlxi1/2b::eGFP+ cells in fused hSS-hCS (two-way ANOVA, interaction $F(24, 408)=17.71$, $P<0.0001$). (FIG. 3H) Scheme illustrating pharmacological manipulation of LTCC during live imaging of fused hSS-hCS in TS versus Ctrl. (FIG. 3I) Quantification of saltation length following exposure to the LTCC antagonist nimodipine (5 µM) in TS versus control (paired t-tests; Ctrl: n=13 cells from 3 hiPSC lines from 3 subjects, *$P<0.001$; TS: n=12 cells from 2 hiPSC lines from 2 subjects, *$P<0.001$).

FIG. 4A-4M. Functional integration of interneurons in fused hSS-hCS. (FIG. 4A) Scheme showing the isolation by dissociation and FACS of Dlxi1/2b::eGFP+ cells from the hSS or hCS side of 4-week fused hCSS-hSS for single cell transcriptional analysis. (FIG. 4B) t-SNE visualization of single cell gene expression of Dlxi1/2b::eGFP+ cells isolated from hSS and hCS of fused hSS-hCS at day 121 of differentiation (4 weeks after forebrain spheroid assembly; n=181 cells; cells form 2 hiPSC lines; Smart-seq2 system). (FIG. 4C) Distribution of cells across clusters A, B and C ($\chi^2$-test, $\chi^2=43.39$, $P<0.0001$). (FIG. 4D) Violin plots showing expression (normalized log 2 transformed) in Dlxi1/2b::eGFP+ cells in clusters A, B, and C (likelihood ratio test; ERBB4, NXPH1, IGF1, TCF4: $P<e^{-6}$ for B versus A & C; FOS, RAD1: $P<e^{-8}$ for C versus A & B). (FIG. 4E) Representative morphologies of Dlxi1/2b::eGFP+ cells before and after migration into hCS in fused hSS-hCS. A 3D reconstruction of Dlxi1/2b::eGFP+ cells before and after migration is shown in FIG. 14*a*. (FIG. 4F) Quantification of dendritic branching of Dlxi1/2b::eGFP+ cells before (n=58 cells) and after (n=55 cells) fusion of hSS to hCS (two-way ANOVA; interaction $F(2, 129)=11.29$, $P<0.001$; Bonferroni post-hoc *$P<0.05$, *$P<0.001$). (FIG. 4G) Action potential generation (slice recordings) in Dlxi1/2b::eGFP+ cells in unfused hSS, in hSS of fused hSS-hCS and in hCS after migration in fused hSS-hCS (one-way ANOVA, $F(2, 30)=1.25$; *$P<0.001$; Bonferroni post-hoc, $P<0.01$; *$P<0.001$). Representative traces are shown in FIG. 14*b*. (FIG. 4H) Array tomography showing a volume reconstruction (4.0×4.0×2.1 µm) on the pallial side of fused hCS-hSS with SYN1 (red) and the GABAergic synapse proteins GPHN (green) and VGAT (cyan). (FIG. 4I) Synaptogram of a Dlxi1/2b::eGFP+ cell illustrating the colocalization with SYN1 (red), GPHN (cyan), and VGAT (white); 5 consecutive 70 nm sections (3×3 µm). (FIG. 4J) Representative traces of EPSCs and IPSCs in Dlxi1/2b::eGFP+ cells after migration into hCS. (FIG. 4K) Quantification of synaptic responses in Dlxi1/2b::eGFP+ cells (IPSCs in green, EPSCs in magenta) in hSS, in hSS of fused hSS-hCS and in hCS after migration in fused hSS-hCS (two-way ANOVA, interaction $F(2, 61)=18.46$, $P<0.0001$; Bonferroni post-hoc for EPSCs, *$P<0.0001$, $P<0.001$). Representative traces are shown in FIG. 14*d*. (FIG. 4L) Quantification of synaptic responses in excitatory cells (IPSCs in green, EPSCs in magenta) in hCS, in hCS of fused hSS-hCS and in hCS after migration in fused hSS-hCS (two-way ANOVA, cortical neurons in hCS before and after fusion $F(1, 26)=5.6$, $P<0.05$; Bonferroni post-hoc for IPSC, *$P<0.05$). Representative traces are shown in FIG. 14*e* (FIG. 4M) Electrical stimulation and patch clamp recording in fused hSS-hCS showing evoked EPSCs and IPSCs before (black trace) and after exposure to 10 µM Gabazine (red trace). Quantification of pre- and post-stimulus events is shown in FIG. 14*f*.

(FIG. 6D-6K) top 25 genes in each of the 8 clusters shown in FIG. 1*j* (proportion of molecules per cells). (FIG. 6L) Scatter plot showing the number of genes detected versus the number of useful reads.

(FIG. 7A) Representative traces of intracellular calcium measurements (Fluo-4) demonstrating spontaneous activity in hSS at ~day 50 of differentiation. (FIG. 7B) Average calcium spike frequency across three distinct hSS differentiation conditions: IS (n=114 cells), ISA (n=327), ISRA (n=136); cells from 3 hiPSC lines; one-way ANOVA, $P=0.006$.

FIG. 8A-8J. Characterization of hSS differentiation conditions. (FIG. 8A) Schematic illustrating the differentiation conditions for deriving hCS or hSS: IS, ISA and ISRA. (FIG. 8B) Gene expression (RT-qPCR, normalized to GAPDH) showing down-regulation of OCT3/4 and the lack of mesoderm (BRACH) and endoderm (SOX17) markers following differentiation of hiPSC into hCS and hSS conditions. (FIG. 8C) Gene expression (RT-PCR, fold change versus hiPSC and normalized to GAPDH) showing upregulation of forebrain markers (SIX3, FOXG1) but not midbrain (LMX1B), hypothalamus (RAX1) or spinal cord (HOXB4) markers. (FIG. 8D) Expression of ventral forebrain genes in hSS and hCS (RT-qPCR, normalized to GAPDH) at day 25. (FIG. 8E) Average percentage of the proportion of NKX2-1 by immunostaining in dissociated hCS or hSS at day 25. (FIG. 8F) Expression of ventral forebrain genes in hSS (RT-qPCR, normalized to GAPDH) at day 60. (FIG. 8G) Expression of glutamatergic, GABAergic, dopaminergic and cholinergic neurotransmitter identify genes in hSS (RT-qPCR, normalized to GAPDH) at day 60. (FIG. 8H) Average percentage of the proportion of MAP2/Hoechst and GAD67/MAP2 by immunostaining in dissociated hSS at day 60. (FIG. 8I, 8J) Expression of interneuron subtypes genes and markers associated with interneuron migration in hSS (RT-qPCR, normalized to GAPDH) at day 60. (n=3-6 hiPSC lines from 1-3 differentiations).

(FIG. 9A) Representative EPSCs traces quantification of recordings from hCS neurons (sliced preparation) before (black trace) and during (green trace) exposure to the glutamate receptor blocker kynurenic acid (1 mM) (Mann-Whitney test, **$P=0.007$). (FIG. 9B) Overlap of averaged EPSCs (red trace) recorded in hCS neurons and averaged IPSCs (black trace) recorded in hSS (n=5-6; mean±standard deviation).

(FIG. 10A, 10B) Representative immunostaining in cryosections of hSS showing co-expression of Dlxi1/2::eGFP and GAD67 and GABA. (FIG. 10T) Plot illustrating the trajectory of Dlxi1/2b::eGFP+ cells in fused hSS-hCS before and after exposure to the CXCR4 antagonist AMD3100.

FIG. 11A-11E. Single cell gene expression in Dlxi1/2b::eGFP+ cells before and after migration (Smart-seq2). (FIG. 11A) Scheme showing the isolation by dissociation and FACS of Dlxi1/2b::eGFP+ cells from hSS or hCS for single cell transcriptional analysis. (FIG. 11B) Violin plots showing expression (normalized log 2 transformed) in Dlxi1/2b::eGFP+ cells of selected genes associated with cortical, striatal and olfactory interneurons in hSS (light green, n=123 cells) or hCS (dark green; n=106 cells) 2 weeks after assembly of hSS-hCS. (FIG. 11C) Violin plots showing expression (normalized log 2 transformed) in Dlxi1/2b::eGFP+ cells (after 4 weeks of migration) in clusters A, B, and C (likelihood ratio test; GAD1, CELF4: $P>0.05$; PBX3: $P<e^{-7}$ for A versus B & C; NNAT:$P<e^{-16}$ for C versus A & B, $P<e^{-18}$ for B versus A & C; MALAT1: $P<e^{-9}$ for C versus A & B; SOX/1: $P<e^{-16}$ for B versus A & C, $P<e^{-9}$ for A versus B & C; GRIP2: $P<e^{-8}$ for B versus A & C). (FIG. 11D) Scatter plot showing the number of genes detected (≥10 reads cutoff) versus the number of reads (n=410 cells from combined single cell RNA-seq experiments after 2 weeks or 4 weeks of assembly in hSS-hCS). (FIG. 11E) Graph illustrating biologically variable transcripts (red circles) and non-variable transcripts (black circles) along with the technical noise from the ERCC spike in RNAs (blue dots). Green line shows the technical noise fit.

(FIG. 12A) (FIG. 12B) (FIG. 12C) Representative images of human fetal cortex at GW20 showing immunostaining with antibodies against GFAP, CTIP2 and GABA. (FIG. 12D) Representative image showing cell labeling with the Dlx2i1/2b::eGFP reporter in fetal human forebrain at GW18 (6 days after lentivirus infection) (FIG. 12E, FIG. 12F) Representative immunostainings in cryosections of human forebrain tissue at GW18 showing co-localization of Dlx2i1/2b::eGFP with NKX2-1 and GABA. (FIG. 12G) Representative images showing cell labeling with the Dlx2i1/2b::eGFP reporter in hSS-hCS (9 daf), in fetal human forebrain (GW18) and in mouse slice cultures (E18). (FIG. 12H, FIG. 12I) Comparison of Dlx2i1/2b::eGFP+ cell size and quantification of the ratio of soma diameter to the length of the leading process in fused hSS-hCS (n=25 cells from 4 hiPSC lines), human fetal forebrain at GW18 (n=19 cells; black dots) and GW20 (n=15 cells; gray dots), hSS-derived cultured on E14 mouse forebrain slices (n=14 cells), and E18 mouse forebrain slices (n=30 cells from 2 litters) (one-way ANOVA, interaction $F(3, 97)=11.61$, $P=0.001$, Bonferroni post-hoc *$P<0.001$, $P<0.05$). (FIG. 12J, 12K, 12L) Comparison of the number of saltations (one-way ANOVA, interaction $F(2, 103)=29.27$, $P=0.001$, Bonferroni post-hoc *$P<0.001$), saltation length (one-way ANOVA, interaction $F(2, 91)=3.0$, $P=0.50$), speed when mobile (one-way ANOVA, interaction $F(2, 83)=11.38$, $P=0.001$, Bonferroni post-hoc *$P<0.001$) for Dlx2i1/2b::eGFP+ in fused hSS-hCS (n=38-56 cells from 2-3 hiPSC lines), human fetal forebrain (GW18: n=19 cells; GW20: n=15 cells), and E18 mouse forebrain slices (n=14-16 cells from 2 litters).

FIG. 13A-13U. Derivation of TS hSS, migration and electroporation (FIG. 13A) Sequencing of PCR-amplified DNA showing the p.G406R mutation in exon 8a of CACNA1C in TS (subject 8303). (FIG. 13B) Representative pictures of iPSC colonies expressing pluripotency markers (OCT4, SSEA4) in one TS subject (FIG. 13C) Level of expression (RT-qPCR, normalized to GAPDH) for NKX2-1 showing no major defects in ventral forebrain induction in TS (two-way ANOVA; interaction $F(2,15)=0.20$, $P=0.81$; TS vs Ctrl $F(1,15)=0.16$, $P=0.68$). (FIG. 13D-13F) Representative immunostainings in cryosections of TS hSS (day 60 of differentiation) showing expression of NKX2-1, GABA, MAP2, GAD67, SST and CR. (FIG. 13G) Calcium imaging (Fura-2) in dissociated hCS derived from TS subjects and controls (Ctrl: n=81 cells from 2 subjects; TS: n=147 cells from 2 subjects). (FIG. 13H, 13I) Quantification of residual intracellular calcium ([Ca2+]i) following 67 mM KCl depolarization of Ctrl and TS cells in hSS cells. Residual intracellular calcium was calculated by dividing the plateau calcium (C−A) level by the peak calcium elevation (B−A); (t-test, *$P<0.0001$). (FIG. 13J) Representative image of fused TS hSS-hCS showing Dlxi1/2b::eGFP expression and migration. (FIG. 13K, 13L) Quantification of the number of saltations and saltation length of Dlx2i1/2b::eGFP cells in fused hSS-hCS across multiple Ctrl and TS lines (related to FIG. 3e, f). (FIG. 13M) Quantification of the speed when mobile of Dlxi1/2b::eGFP cells in fused hSS-hCS in TS and Ctrl (Ctrl: n=21 cells from 3 hiPSC lines from 3 subjects; TS: n=29 cells from 3 hiPSC lines from 3 subjects; TS-Ctrl hybrid: n=12 from 3 hiPSC line combinations; one-way ANOVA with Dunnett's multiple comparison test; *$P<0.001$). (FIG. 13N) Electroporation of the TS- and WT-CaV1.2 channels into slices of mouse E14 ganglionic eminences (GE). (FIG. 13O) Representative example of time-lapse live imaging depicting the saltatory migration of GFP+ cells in slices electroporated with CAG::GFP and either the WT- or the TS-CACNA1C. (FIG. 13P, 13Q) Quantification of the number of saltations (t-test; P<0.01) and saltation length (t-test; *P<0.0001) of GFP+ cells in electroporated mouse forebrain slices (n=33 cells for WT, n=23 cells for TS; from 3 litters). (FIG. 13R) Scheme illustrating pharmacological manipulation of LTCC during live imaging of fused hSS-hCS in TS versus Ctrl. (FIG. 13S) Quantification of speed when mobile following exposure to the LTCC antagonist nimodipine (5 µM) in TS versus control (paired t-tests; Ctrl: n=13 cells from 3 hiPSC lines from 3 subjects, *P<0.001; TS: n=12 cells from 2 hiPSC lines from 2 subjects, P<0.005). (FIG. 13T) Quantification of saltation length following exposure to roscovitine (15 µM) in TS versus Ctrl (paired t-tests; Ctrl: n=7 cells from 2 hiPSC lines from 2 subject, P<0.005; TS: n=12 cells from 2 hiPSC lines from 2 subjects; *P<0.001). (FIG. 13U) Quantification of speed when mobile following exposure to roscovitine (15 µM) in TS versus control (paired t-tests; Ctrl: n=9 cells from 2 hiPSC lines from 2 subject, ***P<0.001; TS: n=12 cells from 2 hiPSC lines from 2 subjects; P=0.05).

(FIG. 14B) Representative examples of action potentials (slice recordings) in Dlxi1/2b::eGFP$^+$ cells in unfused hSS, in hSS of fused hSS-hCS and in hCS after migration in fused hSS-hCS. (FIG. 14C) Array tomography (AT) showing expression of the GABAergic synapse marker GPHN colocalized with SYN1 in hCS of fused hSS-hCS but not in unfused hCS, while the glutamatergic marker PSD95 colocalized with SYN1 is found in both fused and unfused hCS (equal volumes 1.2 µm deep). (FIG. 14D) Representative examples of whole-cell voltage clamp recordings of IPSCs and EPSCs from Dlxi1/2b::eGFP$^+$ cells in unfused hSS, in fused hCS-hSS, or after migration in hCS (FIG. 14E) Representative examples of whole-cell voltage clamp recordings of IPSCs and EPSCs in cells recorded from unfused hCS cells and fused hCS cells. (FIG. 14F) Average peri-stimulus synaptic events (IPSCs and EPSCs) in Dlxi1/2::eGFP$^+$ cells recorded in the hCS side of fused hSS-hCS before and after electrical stimulation (paired t-test, *P<0.05).

DETAILED DESCRIPTION OF THE INVENTION

Figure 5:
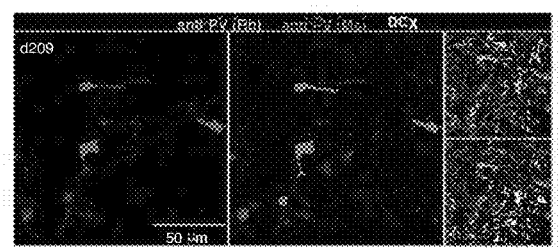
FIG. 5. Immunostaining of hSS in cryosections showing Parvalbumin (PV) neurons. Two anti-PV antibodies have been used for validation of specificity; co-localization with the neuronal marker DCX (day 209).

Before the present compositions and methods are described, it is to be understood that this invention is not limited to particular compositions and methods described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a reprogramming factor polypeptide" includes a plurality of such polypeptides, and reference to "the induced pluripotent stem cells" includes reference to one or more induced pluripotent stem cells and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

By "pluripotency" and pluripotent stem cells it is meant that such cells have the ability to differentiate into all types of cells in an organism. The term "induced pluripotent stem cell" encompasses pluripotent cells, that, like embryonic stem cells (hESC), can be cultured over a long period of time while maintaining the ability to differentiate into all types of cells in an organism. hiPSC have a human hESC-like morphology, growing as flat colonies containing cells with large nucleo-cytoplasmic ratios, defined borders and prominent nuclei. In addition, hiPSC express pluripotency markers known by one of ordinary skill in the art, including but not limited to alkaline phosphatase, SSEA3, SSEA4, SOX2, OCT3/4, NANOG, TRA-1-60, TRA-1-81, etc. In addition, the hiPSC are capable of forming teratomas and are capable of forming or contributing to ectoderm, mesoderm, or endoderm tissues in a living organism.

As used herein, "reprogramming factors" refers to one or more, i.e. a cocktail, of biologically active factors that act on a cell, thereby reprogramming a cell to multipotency or to pluripotency. Reprogramming factors may be provided to the cells, e.g. cells from an individual with a family history or genetic make-up of interest for heart disease such as fibroblasts, adipocytes, etc.; individually or as a single composition, that is, as a premixed composition, of reprogramming factors. The factors may be provided at the same molar ratio or at different molar ratios. The factors may be provided once or multiple times in the course of culturing the cells of the subject invention. In some embodiments the reprogramming factor is a transcription factor, including without limitation, OCT3/4; SOX2; KLF4; c-MYC; NANOG; and LIN-28.

Somatic cells are contacted with reprogramming factors, as defined above, in a combination and quantity sufficient to reprogram the cell to pluripotency. Reprogramming factors may be provided to the somatic cells individually or as a single composition, that is, as a premixed composition, of reprogramming factors. In some embodiments the reprogramming factors are provided as a plurality of coding sequences on a vector. The somatic cells may be fibroblasts, adipocytes, stromal cells, and the like, as known in the art. Somatic cells or hiPSC can be obtained from cell banks, from normal donors, from individuals having a neurologic or psychiatric disease of interest, etc.

Following induction of pluripotency, hiPSC are cultured according to any convenient method, e.g. on irradiated feeder cells and commercially available medium. The hiPSC can be dissociated from feeders by digesting with protease, e.g. dispase, preferably at a concentration and for a period of time sufficient to detach intact colonies of pluripotent stem cells from the layer of feeders. The spheroids can also be generated from hiPSC grown in feeder-free conditions, by dissociation into a single cell suspension and aggregation using various approaches, including centrifugation in plates, etc.

Genes may be introduced into the somatic cells or the hiPSC derived therefrom for a variety of purposes, e.g. to replace genes having a loss of function mutation, provide marker genes, etc. Alternatively, vectors are introduced that express antisense mRNA, siRNA, ribozymes, etc. thereby blocking expression of an undesired gene. Other methods of gene therapy are the introduction of drug resistance genes to enable normal progenitor cells to have an advantage and be subject to selective pressure, for example the multiple drug resistance gene (MDR), or anti-apoptosis genes, such as BCL-2. Various techniques known in the art may be used to introduce nucleic acids into the target cells, e.g. electroporation, calcium precipitated DNA, fusion, transfection, lipofection, infection and the like, as discussed above. The particular manner in which the DNA is introduced is not critical to the practice of the invention. Disease-associated or disease-causing genotypes can be generated in healthy hiPSC through targeted genetic manipulation (CRISPR/CAS9, etc) or hIPSC can be derived from individual patients that carry a disease-related genotype or are diagnosed with a disease, e.g. Timothy Syndrome cells exemplified herein. Moreover, neural diseases with less defined or without genetic components can be studied within the model system. Conditions of neurodevelopmental and neuropsychiatric disorders and neural diseases that have strong genetic components or are directly caused by genetic or genomic alterations can be modeled with the systems of the invention. Genetic alterations include for example point mutations in genes such as NLGN1/3/4, NRXN1/4, SHANK1/2/3, GRIN2B/A, FMR1, or CHD8 that represent risk alleles for autism spectrum disorders, point mutations in or deletions of genes such as CACNA1C, CACNB2, NLGN4X, LAMA2, DPYD, TRRAP, MMP16, NRXN1 or NIPAL3 that are associated with schizophrenia or autism spectrum disorders (ASD), etc, a triplet expansion in the HIT gene that cause to Huntington's disease (HD), monoallelic mutations in genes such as SNCA, LRRK2 and biallelic mutations in genes such as PINK1, DJ-1, or ATP13A2 that predispose to Parkinson disease (PD), single nucleotide polymorphisms (SNPs) in genes such as ApoE, APP, and PSEN1/2 that confer risks for developing Alzheimer's disease (AD) and other forms of dementia, as well as SNPs in genes such as CACNA1C, CACNB3, ODZ4, ANK3 that are associated with bipolar disease (BP); Angelman (UBE3A), Rett (MEPC2), Tuberous sclerosis (TSC1/2). Genomic alterations include copy number variations (CNVs) such as deletions or duplications of 1q21.1, 7q11.23, 15q11.2, 15q13.3, 22q11.2 or 16p11.2, 16p13.3 that are associated with ASD, schizophrenia, intellectual disability, epilepsy, etc; trisomy 21 and Down Syndrome, Fragile X syndrome caused by alteration of the FMR1 gene. Any number of neurodevelopment disorders with a defined genetic etiology can be additionally modeled by introducing mutations in or completely removing disease-relevant gene(s) in control hiPSC using genome editing, e.g. CRISPR. A particular advantage of this method is that fact that edited hiPSC lines share the same genetic background as their corresponding, non-edited hiPSC lines. This reduces variability associated with line-line differences in genetic background.

Disease relevance. The effect of drugs on neurons or glial cells (e.g, astrocytes) is of particular interest, where efficacy and toxicity may rest in sophisticated analysis of neuronal migratory and electrical interactions, or the ability of neurons to form functional networks, rather than on simple viability assays. The discrepancy between the number of lead compounds in clinical development and approved drugs may partially be a result of the methods used to generate the leads and highlights the need for new technology to obtain more detailed and physiologically relevant information on cellular processes in normal and diseased states.

A number of important clinical conditions are associated with altered neuronal or glial function, including neurodegenerative disorders (Alzheimer's disease (AD), Parkinson's disease (PD), Huntington's disease (HD), and amyotrophic lateral sclerosis (ALS), or psychiatric conditions such as schizophrenia and other psychoses, bipolar disorders, mood disorders, intellectual disability or autism spectrum disorders.

Genetic changes may include genotypes that affect migratory, or synaptic function in disorders such as schizophrenia, autism spectrum disorders, monogenic disorders such as Timothy Syndrome, etc. In other embodiments effects of genotypes and agents on neural development can be assessed using neural cultures of the invention during the process of differentiation and migration. Thus, neurodevelopmental effects can be tested that either immediately affect function, maturation, and viability of developing cells, or exhibit long-term effects emerging as phenotypes in mature neural cultures.

A number of neuropsychiatric disorders may arise from an alteration or disruption in the balance of excitation and inhibition in the cerebral cortical circuitry. Additionally, a number of studies have shown that the lack of proper cortical interneuron specification may play a significant role in the development of neuropsychiatric disorders (schizophrenia, autism spectrum disorders, epilepsy and other seizure disorders). This may entail a deviation from either the course of interneuron development, or aberrant transcriptional regulation in the cortical interneuron specification process. Understanding the effects of both GABAergic neurotransmission, alterations in inhibitory cortical circuits, and how they may be responsible for the clinical features observed in schizophrenia or autism are paramount to this field of research.

Conditions of interest may also include DISC1-related disorders, Rett syndrome, Fragile X, Alexander's disease, and others.

Autism spectrum disorders (ASDs) are neurodevelopmental disorders characterized by varying degrees of impaired social interaction and communication and the presence of repetitive and stereotypical behaviors. Some models of ASD emphasize the idea that abnormal synapse development underlies many features of the disease and postulate abnormalities in excitatory-inhibitory balance (E/I ratio). A better understanding of neuronal interactions in ASDs will shed light on pathogenesis and the development of new treatment strategies.

The terms "treatment", "treating", "treat" and the like are used herein to generally refer to obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a mammal, particularly a human, and includes: (a) preventing the disease or symptom from occurring in a subject which may be predisposed to the disease or symptom but has not yet been diagnosed as having it; (b) inhibiting the disease symptom, i.e., arresting its development; or (c) relieving the disease symptom, i.e., causing regression of the disease or symptom.

The terms "individual," "subject," "host," and "patient," are used interchangeably herein and refer to any mammalian subject for whom diagnosis, treatment, or therapy is desired, particularly humans.

Neuronal migration is one of the fundamental mechanisms underlying the wiring of the brain. The nervous system grows both in size and complexity by using migration as a strategy to position cell types from different origins into specific coordinates, allowing for the generation of neural circuits. The migration of newly born neurons is a precisely regulated process that is critical for the development of brain architecture. Neurons arise from the proliferative epithelium that covers the ventricular space throughout the neural tube (VZ, SVZ, oSVZ). During radial migration, neurons follow a trajectory that is perpendicular to the ventricular surface, moving alongside radial glial fibers expanding the thickness of the neural tube. In contrast, tangentially migrating neurons, often born in other ventricular regions of the CNS (e.g, subpallium/ventral forebrain) move in trajectories that are parallel to the ventricular surface and orthogonal radial glia.

The adult cerebral cortex contains two main classes of neurons: glutamatergic cortical neurons (also known as pyramidal cells) and GABAergic interneurons. Pyramidal cells are generated in the pallium—the roof of the telencephalon (dorsal forebrain)—and reach their final position by radial migration. In contrast, cortical interneurons are born in the subpallium—the base of telencephalon (ventral forebrain)—and reach the cerebral cortex through a long tangential migration.

The layers of the cerebral cortex are generated in an "inside-out" sequence, with deep layers being generated first and superficial layer neurons being generated last. In parallel to this process, GABAergic interneurons migrate to the cortical plate, where they disperse tangentially via highly stereotyped routes in the MZ, SP, and lower intermediate zone/subventricular zone (IZ/SVZ). Interneurons then switch from tangential to radial migration to adopt their final laminar position in the cerebral cortex.

The movement of cortical interneurons is saltatory. First, the cell extends a leading process. Second, the nucleus translocates towards the leading process, a step referred to as nucleokinesis and leads to the net movement of the cell.

The translocation of the nucleus into the leading process is the mechanism that best defines this type of saltatory neuronal migration. First, a cytoplasmic swelling forms in the leading process, immediately proximal to the nucleus. The centrosome, which is normally positioned in front of the nucleus, moves into this swelling. The centrosome is accompanied by additional organelles, including the Golgi apparatus, mitochondria, and the rough endoplasmic reticulum. Second, the nucleus follows the centrosome. These two steps are repeated producing the typical saltatory movement of migrating neurons.

Tangentially migrating neurons do not always follow radial glial fibers. In general, tangentially migrating cells can move in clusters or individually. Cellular interactions also differ depending on the nature of the substrate. They can be homotypic, when interactions occur between cells of the same class, or heterotypic, when migrating cells rely on the contact with other cell types for their migration or their substrates. In the most common scenario, neurons respond to cues present in the extracellular matrix or in the surface of other cells to achieve directional migration.

GABAergic interneurons are inhibitory neurons of the nervous system that play a vital role in neural circuitry and activity. They are so named due to their release of the neurotransmitter gamma-aminobutyric acid (GABA). An interneuron is a specialized type of neuron whose primary role is to modulate the activity of other neurons in a neural network. Cortical interneurons are so named for their localization in the cerebral cortex.

There are interneuron subtypes categorized based on the surface markers they express, including parvalbumin (PV)-expressing interneurons, somatostatin (SST)-expressing interneurons, VIP-expressing, serotonin receptor 5HT3a (5HT3aR)-expressing interneurons, etc. Although these interneurons are localized in their respective layers of the cerebral cortex, they are generated in various subpallial locations.

Morphologically speaking, cortical interneurons may be described with regard to their soma, dendrites, axons, and the synaptic connections they make. Molecular features include transcription factors, neuropeptides, calcium-binding proteins, and receptors these interneurons express, among many others. Physiological characteristics include firing pattern, action potential measurements, passive or subthreshold parameters, and postsynaptic responses, to name a few.

The PV interneuron group represents approximately 40% of the GABAergic cortical interneuron population. This population of interneurons possesses a fast-spiking pattern, and fire sustained high-frequency trains of brief action potentials. Additionally, these interneurons possess the lowest input resistance and the fastest membrane time constant of all interneurons. Two types of PV-interneurons make up the PV interneuron group: basket cells, which make synapses at the soma and proximal dendrite of target neurons, and usually have multipolar morphology and chandelier cells, which target the axon initial segment of pyramidal neurons.

The SST-expressing interneuron group is the second-largest interneuron group. SST-positive interneurons are known as Martinotti cells, and possess ascending axons that arborize layer I and establish synapses onto the dendritic tufts of pyramidal neurons. Martinotti cells are found throughout cortical layers II-VI, but are most abundant in layer V. These interneurons function by exhibiting a regular adapting firing pattern but also may initially fire bursts of two or more spikes on slow depolarizing humps when depolarized from hyperpolarized potentials. In contrast to PV-positive interneurons, excitatory inputs onto Martinotti cells are strongly facilitating.

The third group of GABAergic cortical interneurons is designated as the 5HT3aR interneuron group. VIP-expressing interneurons are localized in cortical layers II and III. VIP interneurons generally make synapses onto dendrites, and some have been observed to target other interneurons. Relative to all cortical interneurons, VIP interneurons possess a very high input resistance. In general they possess a bipolar, bitufted and multipolar morphology. Irregular spiking interneurons possess a vertically oriented, descending axon that extends to deeper cortical layers, and have an irregular firing pattern that is characterized by action potentials occurring irregularly during depolarizations near threshold, and express the calcium-binding protein calretinin (CR). Other subtypes include rapid-adapting, fast-adapting neurons IS2, as well as a minor population of VIP-positive basket cells with regular, bursting, or irregular-spiking firing patterns. Of the VIP-negative 5HT3aR group, nearly 80% express the interneuron marker Reelin. Neurogliaform cells are a type of cortical interneuron that belongs to this category: they are also known as spiderweb cells and express neuropeptide Y (NPY), with multiple dendrites radiating from a round soma.

A transcriptional network plays a role in regulating proper development and specification of GABAergic cortical interneurons, including DLX homeobox genes, LHX6, SOX6 and NKX2-1, LHX8, GSX1, GSX2. The DLX family of homeobox genes, specifically DLX1, DLX2, DLX5, and DLX6, also play a role in the specification of interneuron progenitors, and are expressed in most subpallial neural progenitor cells.

Glutamatergic neurons. The mature cerebral cortex harbors a heterogeneous population of glutamatergic neurons, organized into a highly intricate histological architecture. So-called excitatory neurons are usually classified according to the lamina where their soma is located, specific combinations of gene expression, by dendritic morphologies, electrophysiological properties, etc.

Based on the differences in connections, pyramidal neurons are classified as projection neurons with long axons that connect different cortical regions or project to subcortical targets. Cortical projection neurons can be further classified by hodology in associative, commissural and corticofugal subtypes. Associative projection neurons extend axons within a single hemisphere, whereas commissural projection neurons connect neurons in the two cortical hemispheres either through the corpus callosum or the anterior commissure. Cortifugal projection neurons send axons to target areas outside the cerebral cortex, such as the thalamus (corticothalamic neurons), pons (corticopontine neurons (CPN), spinal cord (costicospinal neurons), superior colliculus (corticotectal neurons) and striatum (corticostriatal neurons).

The terms "astrocytic cell," "astrocyte," etc. encompass cells of the astrocyte lineage, i.e. glial progenitor cells, astrocyte precursor cells, and mature astrocytes, which for the purposes of the present invention arise from a non-astrocytic cell by experimental manipulation. Astrocytes can be identified by markers specific for cells of the astrocyte lineage, e.g. GFAP, ALDH1L1, AQP4, EAAT1 and EAAT2, etc. Markers of reactive astrocytes include S100, VIM, LCN2, FGFR3 and the like. Astrocytes may have characteristics of functional astrocytes, that is, they may have the capacity of promoting synaptogenesis in primary neuronal cultures; of accumulating glycogen granules in processes; of phagocytosing synapses; and the like. A "astrocyte precursor" is defined as a cell that is capable of giving rise to progeny that include astrocytes.

Astrocytes are the most numerous and diverse neuroglial cells in the CNS. An archetypal morphological feature of astrocytes is their expression of intermediate filaments, which form the cytoskeleton. The main types of astroglial intermediate filament proteins are glial fibrillary acidic protein (GFAP) and vimentin; expression of GFAP, ALDH1L1 and/or AQP4P are commonly used as a specific marker for the identification of astrocytes.

The functions of astroglial cells are many: astrocytes create the brain environment, build up the micro-architecture of the brain parenchyma, integrate neural circuitry with local blood flow and metabolic support, maintain brain homeostasis, store and distribute energy substrates, control the development of neural cells, synaptogenesis and synaptic maintenance and provide for brain defense. As such, there is considerable interest in studying the effects of drugs and other therapeutic regimens on astrocytic cells.

Astroglia regulate formation, maturation, maintenance, and stability of synapses, thus controlling the connectivity of neuronal circuits. Astrocytes secrete numerous factors required for synaptogenesis. Synaptic formation depends on cholesterol produced and secreted by astrocytes. Glial cells also affect synaptogenesis through signals influencing the expression of agrin and thrombin. Subsequently, astrocytes control maturation of synapses through several signaling systems, which affect the postsynaptic density, for example by controlling the density of postsynaptic receptors. Astroglia factors that affect synapse maturation include TNF and activity-dependent neurotrophic factor (ADNF). Astrocytes may also limit the number of synapses.

Astrocytes and other glial cells can release a variety of transmitters into the extracellular space, including glutamate, ATP, GABA and D-serine.

Astrocytes are involved in all types of brain pathologies from acute lesions (trauma or stroke) to chronic neurodegenerative processes (such as Alexander's disease, Alzheimer's disease, Parkinson's disease, multiple sclerosis and many others) and psychiatric diseases (schizophrenia, autism spectrum disorders, etc). Pathologically relevant neuroglial processes include various programs of activation, which are essential for limiting the areas of damage, producing neuro-immune responses and for the post-insult remodeling and recovery of neural function. Astroglial degeneration and atrophy in the early stages of various neurodegenerative disorders may be important for cognitive impairments.

METHODS OF THE INVENTION

Methods are provided for the obtention and use of in vitro integrated forebrain systems, which comprise interacting cells of at least two forebrain subdomains, including the dorsal pallium and ventral subpallium. The methods comprise an initial step of differentiating pluripotent cells, including without limitation induced human pluripotent stem cells (hiPSC), into the forebrain subdomains of (i) a ventral forebrain structure, referred to herein as a subpallial spheroid (hSS) comprising GABAergic interneurons; and (ii) a cerebral cortical, or dorsal pallium structure (hCS) comprising gluamatergic neurons. The spheroids may also comprise neural progenitor cells, astrocytes, and the like. Following this differentiation step, subpallial spheroid(s)

(hSS) and cortical spheroid(s) (hCS) are placed adjacent to teach other in culture under conditions permissive for fusion or assembly of the two spheroids and generation of the integrated brain system with new properties. In this case, the fused forebrain comprises functionally integrated neurons of excitatory and inhibitory types, which provides a platform for analysis of the effect of agents on brain structure and function.

In some embodiments the neural cells are differentiated from induced human pluripotent stem cells (hiPSC). In some embodiments the hiPSC are derived from somatic cells obtained from neurologically normal individuals. In other embodiments the hiPSC are derived from somatic cells obtained from an individual comprising at least one allele encoding a mutation associated with a neural disease.

Methods are also provided for determining the activity of a candidate agent on a disease-relevant integrated forebrain structure, the method comprising contacting the candidate agent with one or a panel of cells or cell systems differentiated from human pluripotent stem cells, e.g. differentiated from hESC or from hiPSC, where the pluripotent stem cells optionally comprise at least one allele encoding a mutation associated with a neural disease; and determining the effect of the agent on morphologic, genetic or functional parameters, including without limitation formation of synapses, interneuron migration, and the like.

Generation of the subdomain spheroids and cells comprised therein utilizes a multi-step process. Initially, hiPSC can be obtained from any convenient source, or can be generated from somatic cells using art-recognized methods. The hiPSC are dissociated from feeders (or if grown in feeder free, aggregated in spheroids of specific sizes) and grown in suspension culture in the absence of FGF2, preferably when dissociated as intact colonies. In certain embodiments the culture are feeder layer free, e.g. when grown on vitronectin coated vessels. The culture may further be free on non-human protein components, i.e. xeno-free, where the term has its usual art-recognized definition, for example referring to culture medium that is free of non-human serum. Suspension growth optionally includes in the culture medium an effective dose of a selective Rho-associated kinase (ROCK) inhibitor for the initial period of culture, for up to about 6 hours, about 12 hours, about 18 hours, about 24 hours, about 36 hours, about 48 hours, (see, for example, Watanabe et al. (2007) Nature Biotechnology 25:681 686). Inhibitors useful for such purpose include, without limitation, Y-27632; Thiazovivin (Cell Res, 2013, 23(10):1187-200; Fasudil (HA-1077) HCl (J Clin Invest, 2014, 124(9):3757-66); GSK429286A (Proc Natl Acad Sci USA, 2014, 111(12):E1140-8); RKI-1447; AT13148; etc.

The suspension culture of hiPSC is then induced to a neural fate. This culture may be feeder-free and xeno-free. For hCS neural induction, an effective dose of an inhibitor of BMP, and of TGFβ pathways is added to the medium, for a period at least about 2 days, at least about 3 days, at least about 4 days, at least about 5 days, and up to about 10 days, up to about 9 days, up to about 8 days, up to about 7 days, up to about 6 days, up to about 5 days. For example, dorsomorphin (DM) can be added at an effective dose of at least about 0.1 µM, at least about 1 µM, at least about 5 µM, at least about 10 µM, at least about 50 µM, up to about 100 µM concentration, which inhibits bone morphogenetic protein (BMP) type I receptors (ALK2, ALK3 and ALK6). Other useful BMP inhibitors include, without limitation, A 83-01; DMH-1; K 02288; ML 347; SB 505124; etc. SB-431542 can be added at an effective dose of at least about 0.1 µM, at least about 1 µM, at least about 5 µM, at least about 10 µM, at least about 50 µM, up to about 100 µM concentration, which inhibits TGF signaling but has no effect on BMP signaling. Other useful inhibitors of TGF include, without limitation, LDN-193189 (J Clin Invest, 2015, 125(2):796-808); Galunisertib (LY2157299) (Cancer Res, 2014, 74(21):5963-77); LY2109761 (Toxicology, 2014, 326C:9-17); SB525334 (Cell Signal, 2014, 26(12):3027-35); SD-208; EW-7197; Kartogenin; DMH1; LDN-212854; ML347; LDN-193189 HCl (Proc Natl Acad Sci USA, 2013, 110(52):E5039-48); SB505124; Pirfenidone (Histochem Cell Biol, 2014, 10.1007/s00418-014-1223-0); RepSox; K02288; Hesperetin; GW788388; LY364947, etc.

Generation of human sub-pallial spheroids (hSS) and cells comprised therein, including, for example neural progenitors, GABAergic interneurons, astocytes etc. from somatic cells utilizes a similar multi-step process with the inclusion of additional agents to promote ventral forebrain differentiation. Early spheroids patterned by SMAD inhibition, e.g. at the time of transfer to the SMAD inhibitory medium, after about 12 hours, after about 24 hours, after about 1 day, after about 2 days, after about 3 days, after about 4 days, are cultured in the presence of an effective dose of a Wnt inhibitor and an SHH inhibitor in the culture medium. The Wnt and SHH inhibitors are maintained for a period of about 7 days, about 10 days, about 14 days, about 18 days, about 21 days, about 24 days, for example at a concentration of from about 0.1 µM to about 100 µM, and may be from about 1 µM to about 50 µM, from about 5 µM to about 25 µM, etc. depending on the activity of the inhibitor that is selected.

Exemplary WNT inhibitors include, without limitation, XAV-939 selectively inhibits Wnt/β-catenin-mediated transcription through tankyrase1/2 inhibition with IC50 of 11 nM/4 nM in cell-free assays; ICG-001 antagonizes Wnt/β-catenin/TCF-mediated transcription and specifically binds to element-binding protein (CBP) with IC50 of 3 µM; IWR-1-endo is a Wnt pathway inhibitor with IC50 of 180 nM in L-cells expressing Wnt3A, induces Axin2 protein levels and promotes β-catenin phosphorylation by stabilizing Axin-scaffolded destruction complexes; Wnt-059 (C59) is a PORCN inhibitor for Wnt3A-mediated activation of a multimerized TCF-binding site driving luciferase with IC50 of 74 pM in HEK293 cells; LGK-974 is a potent and specific PORCN inhibitor, and inhibits Wnt signaling with IC50 of 0.4 nM in TM3 cells; KY02111 promotes differentiation of hPSCs to cardiomyocytes by inhibiting Wnt signaling, may act downstream of APC and GSK3β; IWP-2 is an inhibitor of Wnt processing and secretion with IC50 of 27 nM in a cell-free assay, selective blockage of Porcn-mediated Wnt palmitoylation, does not affect Wnt/β-catenin in general and displays no effect against Wnt-stimulated cellular responses; IWP-L6 is a highly potent Porcn inhibitor with EC50 of 0.5 nM; WIKI4 is a novel Tankyrase inhibitor with IC50 of 15 nM for TNKS2, and leads to inhibition of Wnt/beta-catenin signaling; FH535 is a Wnt/β-catenin signaling inhibitor and also a dual PPARγ and PPARδ antagonist.

SHH agonists include smoothened agonist, SAG, CAS 364590-63-6, which modulates the coupling of Smo with its downstream effector by interacting with the Smo heptahelical domain ($K_D$=59 nM). SAG may be provided in the medium at a concentration of from about 10 nM to about 10 µM, from about 50 nM to about 1 µM, from about 75 nM to about 500 nM, and may be around about 100 nM.

Optionally the medium in this stage of the hSS culture process further comprises allopregnenolone from about day 10 to about day 23, e.g. from day 11, 12, 13, 14, 15, 16, 17, 18, 19, 20, 21, 22 until the conclusion of the stage; at a concentration of from about 10 nM to about 10 µM, from about 50 nM to about 1 µM, from about 75 nM to about 500 nM, and may be around about 100 nM.

Optionally the hSS cultures are transiently exposed to retinoic acid, e.g. for about 1 to about 4 days, which may be from about day 10 to about day 20, from about day 12 to about day 15, etc., at a concentration of from about 10 nM to about 10 µM, from about 50 nM to about 1 JIM, from about 75 nM to about 500 nM, and may be around about 100 nM.

For both hCS and hSS conditions, after about 5 days, about 6 days, about 7 days, about 8 days, about 9 days, about 10, after about 15 days, after about 20 days, after about 25 days, e.g. around about 23 days, in suspension culture, the floating spheroids are moved to neural media to differentiate neural progenitors. The media is supplemented with an effective dose of FGF2 and EGF. The growth factors can be provided at a concentration for each of at least about 0.5 ng/ml, at least about 1 ng/ml, at least about 5 ng/ml, at least about 10 ng/ml, at least about 20 ng/ml, up to about 500 ng/ml, up to about 250 ng/ml, up to about 100 ng/ml.

To promote differentiation of neural progenitors into neurons, after about 1 week, about 2 weeks, about 3 weeks, about 4 weeks after FGF2/EGF exposure the neural medium is changed to replace the FGF2 and EGF with an effective dose of BDNF and NT3. The growth factors can be provided at a concentration for each of at least about 0.5 ng/ml, at least about 1 ng/ml, at least about 5 ng/ml, at least about 10 ng/ml, at least about 20 ng/ml, up to about 500 ng/ml, up to about 250 ng/ml, up to about 100 ng/ml.

After about 4 weeks, about 5 weeks, about 6 weeks, about 7 weeks after FGF2/EGF exposure, the spheres can be maintained for extended periods of time in neural medium in the absence of growth factors, e.g. for periods of 1, 2, 3, 4, 5, 6, 7, 8, 9, 10, 11, 12 months or longer. The number of astrocytes in the cultures are initially low for the first month, and increase in number after that, up to from about 5%, about 10%, about 15%, about 20%, about 25%, to about 30% or more of the cells in the spheroids.

To fuse or assemble the two subdomain spheroids into an integrated forebrain structure, one or more of each hCS and hSS spheroids are brought into close physical proximity, e.g. resting in a conical tube. The two spheroids may be combined in a 1:1 ratio, 1:2, 2:1, 1:3, 3:1, etc. ratio of hCS to hSS for the desired outcome. The integrated structure is maintained in culture for extended periods of time, e.g. for up to about 30 days, up to about 40 days, up to about 50 days, up to about 60 days, up to about 70 days, up to about 80 days, up to about 90 days, or more. Other region-specific brain spheroids can be specified from hPSC in vitro and assembled using a similar approach to generate multi-region brain 3D cultures that communicate and exhibit novel (emergent) features and capabilities versus conventional culture approaches or versus the same spheroids cultured in isolation.

Populations of cells can be isolated from the forebrain structure by any convenient method, including flow cytometry, magnetic immunoselection, immunopanning, etc. The cells thus isolated can be resuspended in an acceptable medium and maintained in culture, frozen, analyzed for parameters of interest; transplanted into a human or animal model; and the like.

Screening Assays

In screening assays for the small molecules, the effect of adding a candidate agent to integrated forebrain system, to an hSS, to isolated cells, and including without limitation at the initiation of fusion between the hCS and the hSS subdomains to determine the effect on migration, synapse formation, etc. in culture is tested with one or a panel of cellular environments, where the cellular environment includes one or more of: electrical stimulation including alterations in ionicity, stimulation with a candidate agent of interest, contact with other cells including without limitation neurons and neural progenitors, contact with infectious agents, e.g. Zika virus, and the like, and where cells may vary in genotype, in prior exposure to an environment of interest, in the dose of agent that is provided, etc. Usually at least one control is included, for example a negative control and a positive control. Culture of cells is typically performed in a sterile environment, for example, at 37° C. in an incubator containing a humidified 92-95% air/5-8% $CO_2$ atmosphere. Cell culture may be carried out in nutrient mixtures containing undefined biological fluids such as fetal calf serum, or media which is fully defined and serum free. The effect of the altering of the environment is assessed by monitoring multiple output parameters, including morphological, functional and genetic changes.

Examples of analytic methods comprise, for example, assessing the synaptic integration of migrated neurons by using array tomography to detect pre- and post-synaptic proteins in hCS before and after fusion to hSS, such as the presence of gephyrin (GPHN), a postsynaptic protein localized to GABAergic synapses. To further examine these synaptic puncta 'synaptograms' consisting of a series of high-resolution sections through a single synapse may be obtained. Whole-cell voltage clamp recordings of synaptic responses can be performed on slices on the forebrain system, and to distinguish between excitatory postsynaptic currents (EPSCs, downward deflecting) and IPSCs (upward deflecting), a low Cl⁻ solution may be used in the patch pipette with cells held at −40 mV.

Live imaging of cells, including during cell migration, may be performed and cells modified to express a detectable marker. Calcium sensitive dyes can be used, e.g. Fura-2 calcium imaging; Fluo-4 calcium imaging, GCaMP6 calcium imaging, voltage imaging using voltage indicators such as voltage-sensitive dyes (e.g. di-4-ANEPPS, di-8-ANEPPS, and RH237) and/or genetically-encoded voltage indicators (e.g. ASAP1, Archer) can be used on the intact spheroids, or on cells isolated therefrom.

Methods of analysis at the single cell level are also of interest, e.g. as described above: live imaging (including confocal or light-sheet microscopy), single cell gene expression or single cell RNA sequencing, calcium imaging, immunocytochemistry, patch-clamping, flow cytometry and the like. Various parameters can be measured to determine the effect of a drug or treatment on the forebrain system or cells derived therefrom.

Parameters are quantifiable components of cells, particularly components that can be accurately measured, desirably in a high throughput system. A parameter can also be any cell component or cell product including cell surface determinant, receptor, protein or conformational or posttranslational modification thereof, lipid, carbohydrate, organic or inorganic molecule, nucleic acid, e.g. mRNA, DNA, etc. or a portion derived from such a cell component or combinations thereof. While most parameters will provide a quantitative readout, in some instances a semi-quantitative or qualitative result will be acceptable. Readouts may include a single determined value, or may include mean, median value or the variance, etc. Variability is expected and a range of values for each of the set of test parameters will be obtained using standard statistical methods with a common statistical method used to provide single values.

Parameters of interest include detection of cytoplasmic, cell surface or secreted biomolecules, frequently biopolymers, e.g. polypeptides, polysaccharides, polynucleotides, lipids, etc. Cell surface and secreted molecules are a preferred parameter type as these mediate cell communication and cell effector responses and can be more readily assayed. In one embodiment, parameters include specific epitopes. Epitopes are frequently identified using specific monoclonal antibodies or receptor probes. In some cases the molecular entities comprising the epitope are from two or more substances and comprise a defined structure; examples include combinatorically determined epitopes associated with heterodimeric integrins. A parameter may be detection of a specifically modified protein or oligosaccharide. A parameter may be defined by a specific monoclonal antibody or a ligand or receptor binding determinant.

Candidate agents of interest are biologically active agents that encompass numerous chemical classes, primarily organic molecules, which may include organometallic molecules, inorganic molecules, genetic sequences, etc. An important aspect of the invention is to evaluate candidate drugs, select therapeutic antibodies and protein-based therapeutics, with preferred biological response functions. Candidate agents comprise functional groups necessary for structural interaction with proteins, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof.

Included are pharmacologically active drugs, genetically active molecules, etc. Compounds of interest include chemotherapeutic agents, anti-inflammatory agents, hormones or hormone antagonists, ion channel modifiers, and neuroactive agents. Exemplary of pharmaceutical agents suitable for this invention are those described in, "The Pharmacological Basis of Therapeutics," Goodman and Gilman, McGraw-Hill, New York, New York, (1996), Ninth edition, under the sections: Drugs Acting at Synaptic and Neuroeffector Junctional Sites; Cardiovascular Drugs; Vitamins, Dermatology; and Toxicology, all incorporated herein by reference.

Test compounds include all of the classes of molecules described above, and may further comprise samples of unknown content. Of interest are complex mixtures of naturally occurring compounds derived from natural sources such as plants. While many samples will comprise compounds in solution, solid samples that can be dissolved in a suitable solvent may also be assayed. Samples of interest include environmental samples, e.g. ground water, sea water, mining waste, etc.; biological samples, e.g. lysates prepared from crops, tissue samples, etc.; manufacturing samples, e.g. time course during preparation of pharmaceuticals; as well as libraries of compounds prepared for analysis; and the like. Samples of interest include compounds being assessed for potential therapeutic value, i.e. drug candidates.

The term samples also includes the fluids described above to which additional components have been added, for example components that affect the ionic strength, pH, total protein concentration, etc. In addition, the samples may be treated to achieve at least partial fractionation or concentration. Biological samples may be stored if care is taken to reduce degradation of the compound, e.g. under nitrogen, frozen, or a combination thereof. The volume of sample used is sufficient to allow for measurable detection, usually from about 0.1 to 1 ml of a biological sample is sufficient.

Compounds, including candidate agents, are obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

As used herein, the term "genetic agent" refers to polynucleotides and analogs thereof, which agents are tested in the screening assays of the invention by addition of the genetic agent to a cell. The introduction of the genetic agent results in an alteration of the total genetic composition of the cell. Genetic agents such as DNA can result in an experimentally introduced change in the genome of a cell, generally through the integration of the sequence into a chromosome, for example using CRISPR mediated genomic engineering (see for example Shmakov et al. (2017) Nature Reviews Microbiology 15:169). Genetic changes can also be transient, where the exogenous sequence is not integrated but is maintained as an episomal agents. Genetic agents, such as antisense oligonucleotides, can also affect the expression of proteins without changing the cell's genotype, by interfering with the transcription or translation of mRNA. The effect of a genetic agent is to increase or decrease expression of one or more gene products in the cell.

Introduction of an expression vector encoding a polypeptide can be used to express the encoded product in cells lacking the sequence, or to over-express the product. Various promoters can be used that are constitutive or subject to external regulation, where in the latter situation, one can turn on or off the transcription of a gene. These coding sequences may include full-length cDNA or genomic clones, fragments derived therefrom, or chimeras that combine a naturally occurring sequence with functional or structural domains of other coding sequences. Alternatively, the introduced sequence may encode an anti-sense sequence; be an anti-sense oligonucleotide; RNAi, encode a dominant negative mutation, or dominant or constitutively active mutations of native sequences; altered regulatory sequences, etc.

Antisense and RNAi oligonucleotides can be chemically synthesized by methods known in the art. Preferred oligonucleotides are chemically modified from the native phosphodiester structure, in order to increase their intracellular stability and binding affinity. A number of such modifications have been described in the literature, which alter the chemistry of the backbone, sugars or heterocyclic bases. Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH2-5'-O-phosphonate and 3'-NH-5'-O-phosphoroamidate. Peptide nucleic acids replace the entire ribose phosphodiester backbone with a peptide linkage. Sugar modifications are also used to enhance stability and affinity, e.g. morpholino oligonucleotide analogs.

Agents are screened for biological activity by adding the agent to at least one and usually a plurality of cells, in one or in a plurality of environmental conditions, e.g. following stimulation with an agonist, following electric or mechanical stimulation, etc. The change in parameter readout in response to the agent is measured, desirably normalized, and the resulting screening results may then be evaluated by comparison to reference screening results, e.g. with cells having other mutations of interest, normal astrocytes, astrocytes derived from other family members, and the like. The reference screening results may include readouts in the presence and absence of different environmental changes, screening results obtained with other agents, which may or may not include known drugs, etc.

The agents are conveniently added in solution, or readily soluble form, to the medium of cells in culture. The agents may be added in a flow-through system, as a stream, intermittent or continuous, or alternatively, adding a bolus of the compound, singly or incrementally, to an otherwise static solution. In a flow-through system, two fluids are used, where one is a physiologically neutral solution, and the other is the same solution with the test compound added. The first fluid is passed over the cells, followed by the second. In a single solution method, a bolus of the test compound is added to the volume of medium surrounding the cells. The overall concentrations of the components of the culture medium should not change significantly with the addition of the bolus, or between the two solutions in a flow through method.

Preferred agent formulations do not include additional components, such as preservatives, that may have a significant effect on the overall formulation. Thus preferred formulations consist essentially of a biologically active compound and a physiologically acceptable carrier, e.g. water, ethanol, DMSO, etc. However, if a compound is liquid without a solvent, the formulation may consist essentially of the compound itself.

A plurality of assays may be run in parallel with different agent concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in the phenotype.

Various methods can be utilized for quantifying the presence of selected parameters, in addition to the functional parameters described above. For measuring the amount of a molecule that is present, a convenient method is to label a molecule with a detectable moiety, which may be fluorescent, luminescent, radioactive, enzymatically active, etc., particularly a molecule specific for binding to the parameter with high affinity fluorescent moieties are readily available for labeling virtually any biomolecule, structure, or cell type. Immunofluorescent moieties can be directed to bind not only to specific proteins but also specific conformations, cleavage products, or site modifications like phosphorylation. Individual peptides and proteins can be engineered to fluoresce, e.g. by expressing them as green fluorescent protein chimeras inside cells (for a review see Jones et al. (1999) Trends Biotechnol. 17(12):477-81). Thus, antibodies can be genetically modified to provide a fluorescent dye as part of their structure Depending upon the label chosen, parameters may be measured using other than fluorescent labels, using such immunoassay techniques as radioimmunoassay (RIA) or enzyme linked immunosorbance assay (ELISA), homogeneous enzyme immunoassays, and related non-enzymatic techniques. These techniques utilize specific antibodies as reporter molecules, which are particularly useful due to their high degree of specificity for attaching to a single molecular target. U.S. Pat. No. 4,568,649 describes ligand detection systems, which employ scintillation counting. These techniques are particularly useful for protein or modified protein parameters or epitopes, or carbohydrate determinants. Cell readouts for proteins and other cell determinants can be obtained using fluorescent or otherwise tagged reporter molecules. Cell based ELISA or related non-enzymatic or fluorescence-based methods enable measurement of cell surface parameters and secreted parameters. Capture ELISA and related non-enzymatic methods usually employ two specific antibodies or reporter molecules and are useful for measuring parameters in solution. Flow cytometry methods are useful for measuring cell surface and intracellular parameters, as well as shape change and granularity and for analyses of beads used as antibody- or probe-linked reagents. Readouts from such assays may be the mean fluorescence associated with individual fluorescent antibody-detected cell surface molecules or cytokines, or the average fluorescence intensity, the median fluorescence intensity, the variance in fluorescence intensity, or some relationship among these.

Both single cell multiparameter and multicell multiparameter multiplex assays, where input cell types are identified and parameters are read by quantitative imaging and fluorescence and confocal microscopy are used in the art, see Confocal Microscopy Methods and Protocols (Methods in Molecular Biology Vol. 122.) Paddock, Ed., Humana Press, 1998. These methods are described in U.S. Pat. No. 5,989,833 issued Nov. 23, 1999.

Neuronal activity parameters. Of particular interest for the disclosed neuronal screening system are parameters related to the electrical properties of the cells and therefore directly informative about neuronal function and activity. Methods to measure neuronal activity may sense the occurrence of action potentials (spikes). The characteristics of the occurrence of a single spike or multiple spikes either in timely clustered groups (bursts) or distributed over longer time (spike train) of a single neuron or a group of neurons indicate neuronal activation patterns and thus reflect functional neuronal properties, which can be described my multiple parameters. Such parameters can be used to quantify and describe changes in neuronal activity in the systems of the invention.

Neuronal activity parameters include, without limitation, total number of spikes (per recording period); mean firing rate (of spikes); inter-spike interval (distance between sequential spikes); total number of bursts (per recording period); burst frequency; number of spikes per burst; burst duration (in milliseconds); inter-burst interval (distance between sequential bursts); burst percentage (the portion of spikes occurring within a burst); total number of network bursts (spontaneous synchronized network activity); network burst frequency; number of spikes per network burst; network burst duration; inter-network-burst interval; inter-spike interval within network bursts; network burst percentage (the portion of bursts occurring within a network burst); salutatory migration, etc.

Quantitative readouts of neuronal activity parameters may include baseline measurements in the absence of agents or a pre-defined genetic control condition and test measurements in the presence of a single or multiple agents or a genetic test condition. Furthermore, quantitative readouts of neuronal activity parameters may include long-term recordings and may therefore be used as a function of time (change of parameter value). Readouts may be acquired either spontaneously or in response to or presence of stimulation or perturbation of the complete neuronal network or selected components of the network. The quantitative readouts of neuronal activity parameters may further include a single determined value, the mean or median values of parallel, subsequent or replicate measurements, the variance of the measurements, various normalizations, the cross-correlation between parallel measurements, etc. and every statistic used to a calculate a meaningful and informative factor.

Comprehensive measurements of neuronal activity using electrical or optical recordings of the parameters described herein may include spontaneous activity and activity in response to targeted electrical or optical stimulation of all neuronal cells or a subpopulation of neuronal cells within the integrated forebrain. Furthermore, spontaneous or induced neuronal activity can be measured in the self-assembled functional environment and circuitry of the neural culture or under conditions of selective perturbation or excitation of specific subpopulations of neuronal cells as discussed above.

In the provided assays, comprehensive measurements of neuronal activity can be conducted at different time points along neuronal maturation and usually include a baseline measurement directly before contacting the neural culture with the agents of interest and a subsequent measurement under agent exposure. Moreover, long-term effects of agents on neural maturation and development can be assessed by contacting the immature neural culture at an early time point with agents of interest and acquiring measurements of the same cultures after further maturation at a later time point compared to control cultures without prior agent exposure.

In some embodiments, standard recordings of neuronal activity of mature neural cultures are conducted after about 2 weeks, after about 3 weeks, after about 4 weeks, after about 6 weeks, after about 8 weeks following fusion (i.e. after mixing the different subdomain components of the culture). Recordings of neuronal activity may encompass the measurement of additive, synergistic or opposing effects of agents that are successively applied to the cultures, therefore the duration recording periods can be adjusted according to the specific requirements of the assay. In some embodiments the measurement of neuronal activity is performed for a predetermined concentration of an agent of interest, whereas in other embodiments measurements of neuronal activity can be applied for a range of concentrations of an agent of interest.

In some embodiments the provided assays are used to assess maturation of the neural culture or single components including GABAergic interneurons, glutamatergic neurons, astrocytes, etc. Maturation of neuronal cells can be measured based on morphology by optically assessing parameters such as dendritic arborization, axon elongation, total area of neuronal cell bodies, number of primary processes per neuron, total length of processes per neuron, number of branching points per primary process as well as density and size of synaptic puncta stained by synaptic markers such as synapsin-1, synaptophysin, bassoon, PSD95, and Homer. Moreover, general neuronal maturation and differentiation can be assessed by measuring expression of marker proteins such as MAP2, TUJ-1, NeuN, Tau, PSA-NCAM, and SYN-1 alone or in combination using FACS analysis, immunoblotting, or fluorescence microscopy imaging, patch clamping. Maturation and differentiation of neuronal subtypes can further be tested by measuring expression of specific proteins. For excitatory neuronal cells this includes staining for e.g. VGLUT1/2, GRIA1/2/3/4, GRIN1, GRIN2A/B, GPHN etc. For inhibitory neuronal cells this includes staining for e.g. GABRA2, GABRB1, VGAT, and GAD67.

The results of an assay can be entered into a data processor to provide a dataset. Algorithms are used for the comparison and analysis of data obtained under different conditions. The effect of factors and agents is read out by determining changes in multiple parameters. The data will include the results from assay combinations with the agent(s), and may also include one or more of the control state, the simulated state, and the results from other assay combinations using other agents or performed under other conditions. For rapid and easy comparisons, the results may be presented visually in a graph, and can include numbers, graphs, color representations, etc.

The dataset is prepared from values obtained by measuring parameters in the presence and absence of different cells, e.g. genetically modified cells, cells cultured in the presence of specific factors or agents that affect neuronal function, as well as comparing the presence of the agent of interest and at least one other state, usually the control state, which may include the state without agent or with a different agent. The parameters include functional states such as synapse formation and calcium ions in response to stimulation, whose levels vary in the presence of the factors. Desirably, the results are normalized against a standard, usually a "control value or state," to provide a normalized data set. Values obtained from test conditions can be normalized by subtracting the unstimulated control values from the test values, and dividing the corrected test value by the corrected stimulated control value. Other methods of normalization can also be used; and the logarithm or other derivative of measured values or ratio of test to stimulated or other control values may be used. Data is normalized to control data on the same cell type under control conditions, but a dataset may comprise normalized data from one, two or multiple cell types and assay conditions.

The dataset can comprise values of the levels of sets of parameters obtained under different assay combinations. Compilations are developed that provide the values for a sufficient number of alternative assay combinations to allow comparison of values.

A database can be compiled from sets of experiments, for example, a database can contain data obtained from a panel of assay combinations, with multiple different environmental changes, where each change can be a series of related compounds, or compounds representing different classes of molecules.

Mathematical systems can be used to compare datasets, and to provide quantitative measures of similarities and differences between them. For example, the datasets can be analyzed by pattern recognition algorithms or clustering methods (e.g. hierarchical or k-means clustering, etc.) that use statistical analysis (correlation coefficients, etc.) to quantify relatedness. These methods can be modified (by weighting, employing classification strategies, etc.) to optimize the ability of a dataset to discriminate different functional effects. For example, individual parameters can be given more or less weight when analyzing the dataset, in order to enhance the discriminatory ability of the analysis. The effect of altering the weights assigned each parameter is assessed, and an iterative process is used to optimize pathway or cellular function discrimination.

The comparison of a dataset obtained from a test compound, and a reference dataset(s) is accomplished by the use of suitable deduction protocols, AI systems, statistical comparisons, etc. Preferably, the dataset is compared with a database of reference data. Similarity to reference data involving known pathway stimuli or inhibitors can provide an initial indication of the cellular pathways targeted or altered by the test stimulus or agent.

A reference database can be compiled. These databases may include reference data from panels that include known agents or combinations of agents that target specific pathways, as well as references from the analysis of cells treated under environmental conditions in which single or multiple environmental conditions or parameters are removed or specifically altered. Reference data may also be generated from panels containing cells with genetic constructs that selectively target or modulate specific cellular pathways. In this way, a database is developed that can reveal the contributions of individual pathways to a complex response.

The effectiveness of pattern search algorithms in classification can involve the optimization of the number of parameters and assay combinations. The disclosed techniques for selection of parameters provide for computational requirements resulting in physiologically relevant outputs. Moreover, these techniques for pre-filtering data sets (or potential data sets) using cell activity and disease-relevant biological information improve the likelihood that the outputs returned from database searches will be relevant to predicting agent mechanisms and in vivo agent effects.

For the development of an expert system for selection and classification of biologically active drug compounds or other interventions, the following procedures are employed. For every reference and test pattern, typically a data matrix is generated, where each point of the data matrix corresponds to a readout from a parameter, where data for each parameter may come from replicate determinations, e.g. multiple individual cells of the same type. As previously described, a data point may be quantitative, semi-quantitative, or qualitative, depending on the nature of the parameter.

The readout may be a mean, average, median or the variance or other statistically or mathematically derived value associated with the measurement. The parameter readout information may be further refined by direct comparison with the corresponding reference readout. The absolute values obtained for each parameter under identical conditions will display a variability that is inherent in live biological systems and also reflects individual cellular variability as well as the variability inherent between individuals.

Classification rules are constructed from sets of training data (i.e. data matrices) obtained from multiple repeated experiments. Classification rules are selected as correctly identifying repeated reference patterns and successfully distinguishing distinct reference patterns. Classification rule-learning algorithms may include decision tree methods, statistical methods, naive Bayesian algorithms, and the like.

A knowledge database will be of sufficient complexity to permit novel test data to be effectively identified and classified. Several approaches for generating a sufficiently encompassing set of classification patterns, and sufficiently powerful mathematical/statistical methods for discriminating between them can accomplish this.

The data from cells treated with specific drugs known to interact with particular targets or pathways provide a more detailed set of classification readouts. Data generated from cells that are genetically modified using over-expression techniques and anti-sense techniques, permit testing the influence of individual genes on the phenotype.

A preferred knowledge database contains reference data from optimized panels of cells, environments and parameters. For complex environments, data reflecting small variations in the environment may also be included in the knowledge database, e.g. environments where one or more factors or cell types of interest are excluded or included or quantitatively altered in, for example, concentration or time of exposure, etc.

For further elaboration of general techniques useful in the practice of this invention, the practitioner can refer to standard textbooks and reviews in cell biology, tissue culture, embryology, stem cell biology, human development and neurobiology. With respect to tissue culture and embryonic stem cells, the reader may wish to refer to Teratocarcinomas and embryonic stem cells: A practical approach (E. J. Robertson, ed., IRL Press Ltd. 1987); Guide to Techniques in Mouse Development (P. M. Wasserman et al. eds., Academic Press 1993); Embryonic Stem Cell Differentiation in Vitro (M. V. Wiles, Meth. Enzymol. 225:900, 1993); Properties and uses of Embryonic Stem Cells: Prospects for Application to Human Biology and Gene Therapy (P. D. Rathjen et al., Reprod. Fertil. Dev. 10:31, 1998).

General methods in molecular and cellular biochemistry can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998). Reagents, cloning vectors, and kits for genetic manipulation referred to in this disclosure are available from commercial vendors such as BioRad, Stratagene, Invitrogen, Sigma-Aldrich, and Clon-Tech.

Each publication cited in this specification is hereby incorporated by reference in its entirety for all purposes.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention, which will be limited only by the appended claims.

As used herein the singular forms "a", "and", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXPERIMENTAL

Example 1

Assembly of Functionally-Integrated Forebrain Spheroids from Human Pluripotent Cells to Study Development and Disease The development of the central nervous system involves a coordinated succession of events including the long-distance migration of GABAergic neurons from the ventral to the dorsal forebrain and their integration into cortical circuits. Defects in these processes have been associated with brain disorders and pluripotent stem cells (hPSC) hold promise in dissecting the underlying pathophysiology in humans. However, these interregional interactions have not yet been modeled with human cells. Here, we describe an approach for generating from hPSCs neural 3D spheroids resembling either the ventral forebrain and containing GABAergic interneurons-subpallial spheroids (hSS), or the dorsal pallium and containing glutamatergic neurons-cerebral cortical spheroids (hCS). We show that these subdomain-specific forebrain spheroids can be assembled in 3D in vitro to recapitulate the saltatory migration of human interneurons into the cortex similar to migration in the mid-gestation human fetal forebrain and to study interneuron dysfunction in the context of human disease. Specifically, we found that interneurons derived from patients with Timothy syndrome—a severe neurodevelopmental disorder caused by a mutation in an L-type calcium channel (LTCC), display more frequent but less efficient migratory saltations, and that this deficit can be rescued pharmacologically in vitro. Lastly, we demonstrate that after migration into hCS, human GABAergic interneurons integrate synaptically with glutamatergic neurons forming a 3D cortical microphysiological system (MPS) that exhibits excitatory and inhibitory synaptic activity. We anticipate that this approach will be useful for studying human development and the mechanisms leading to neurodevelopmental disease, as well as for deriving spheroids resembling other human brain regions to ultimately assemble neural microcircuits in vitro.

The formation and function of the human cerebral cortex involves the assembly of circuits composed of glutamatergic excitatory neurons, which are generated in the dorsal forebrain (pallium), and GABAergic inhibitory interneurons, which are born in the ventral forebrain (subpallium). After specification, interneurons migrate long distances over several months during human fetal development and subsequently undergo activity-dependent maturation and integration into cortical circuits. Genetic or environmental perturbations of this elaborate process can lead to an imbalance of cortical excitation and inhibition and are thought to contribute to the pathophysiology of neuropsychiatric disorders, including epilepsy and autism. These key developmental processes, which occur mostly in mid to late gestation, have been largely inaccessible for functional studies in humans. Moreover, the directed differentiation, and particularly the functional maturation of human cortical interneurons from human pluripotent stem cells (induced pluripotent stem cells, hiPSC, or embryonic stem cells, hESCs) has been. To date, no reliable, personalized models exist to study the migration of human interneurons and their functional integration into cortical ensembles.

Here, we leverage a 3D differentiation approach using hPSCs to specify neural spheroids resembling the pallium (hCS) or the subpallium (hSS), and we subsequently assemble them in vitro to model for the first time the saltatory migration of human interneurons towards the cortex. We use live imaging to show that this pattern of migration is similar to interneuron migration in the mid-gestation human fetal forebrain. As a proof of principle, we examine patient-derived cells bearing a gain of function mutation in CACNA1C, encoding the voltage gated L-type calcium channel (LTCC) $Ca_V1.2$, and using a combination of live imaging and pharmacology in fused hSS-hCS, we find that interneuron migration is impaired in spheroids from these patients. Lastly, we demonstrate that hiPSC-derived GABAergic interneurons migrating from hSS into hCS form a complex functional network with cortical glutamatergic neurons, which includes both excitation and inhibition.

TABLE 1

| | SUPPLEMENTARY TABLE 1 | | | | | | | | | | | | | |
|---|---|---|---|---|---|---|---|---|---|---|---|---|---|---|
| INDIVIDUAL/ | Ctrl hiPSC (5 subjects, 6 lines) | | | | | | TS hiPSC (3 subjects, 7 lines) | | | | | | | hESC |
| EXPERIMENT | 2242-1 | 8858-1 | 8858-3 | 1205-4 | 6593-8 | H20961 | 8303-1 | 8303-2 | 7643-1 | 7643-5 | 7643-32 | 9862-2 | 9862-61 | H9 |
| hSS qPCR characterization | ✓ | ✓ | ✓ | ✓ | ✓ | ✓ | ✓ | ✓ | ✓ | ✓ | ✓ | ✓ | | ✓ |
| hSS ICC characterization | ✓ | ✓ | | ✓ | | | | | | | | | | ✓ |
| hSS IHC characterization | ✓ | ✓ | | ✓ | | | | | | ✓ | | ✓ | | ✓ |
| Single-cell analysis | ✓ | ✓ | | | | | | | | | | | | |
| Calcium Imaging - Fura-2 | ✓ | ✓ | | ✓ | | | | | | ✓ | ✓ | | ✓ | ✓ |
| Calcium Imaging - Fluo-4 | ✓ | | | ✓ | ✓ | | | | | | | | | ✓ |
| Dlxi1/2b::eGFP reporter characterization | ✓ | ✓ | | | | ✓ | | | | | | | | |

TABLE 1-continued

SUPPLEMENTARY TABLE 1

| INDIVIDUAL/ EXPERIMENT | Ctrl hiPSC (5 subjects, 6 lines) | | | | | | TS hiPSC (3 subjects, 7 lines) | | | | | | | hESC |
|---|---|---|---|---|---|---|---|---|---|---|---|---|---|---|
| | 2242-1 | 8858-1 | 8858-3 | 1205-4 | 6593-8 | H20961 | 8303-1 | 8303-2 | 7643-1 | 7643-5 | 7643-32 | 9862-2 | 9862-61 | H9 |
| hSS-hCS migration assays and pharmacology | ✓ | ✓ | | ✓ | | ✓ | ✓ | ✓ | ✓ | ✓ | | ✓ | ✓ | |
| Dendritic branching | ✓ | ✓ | | ✓ | | | | | | | | | | |
| Array Tomography | ✓ | ✓ | | | | | | | | | | | | |
| Slice physiology | ✓ | ✓ | ✓ | ✓ | ✓ | | | | | | | | | ✓ |
| hSS culture on mouse forebrain slices | | ✓ | | | ✓ | | | | | | | | | |

We have previously described the generation of floating, 3D neural cultures from hPSCs resembling the dorsal pallium (hCS) that contain both deep and superficial layer cortical glutamatergic neurons, as well as astrocytes. To specify spheroids resembling the ventral forebrain or the subpallium (hSS), we exposed early spheroids patterned by double SMAD inhibition to small molecules modulating the WNT pathway (inhibitor of WNT production-2, IWP-2; 5 µM) and the SHH pathway (smoothened agonist, SAG; 100 nM) in the presence of the growth factors FGF2 and EGF2 (20 µM) (hSS; FIG. 1a; the 6 hiPSCs and 1 hESC line used in each assay are shown in Table 1). At day 25 of hSS in vitro differentiation, we observed a strong induction of the transcription factor NKX2-1 accompanied by high levels of FOXG1 expression and down-regulation of the dorsal pallial marker EMX1, suggestive of a ventral forebrain fate (FIG. 1b). We next examined the cytoarchitecture in hSS cryosections and noticed that NKX2-1 was expressed in ventricular zone (VZ)-like structures at day 25 (FIG. 1c) but was distributed more broadly at later stages (FIG. 1d). At day 60, we observed strong expression by immunocytochemistry of GABA and the GABA-synthesizing enzyme GAD67 in MAP2$^+$ neurons (FIG. 1e, f). Of the known markers of GABAergic subtype identity, somatostatin (SST), calretinin (CR) and calbindin (CB) were the most strongly expressed, while at later stages (>200 days in vitro) and consistent with its later in vivo expression in development, parvalbumin (PV) was also present (FIG. 1g, h; FIG. 5).

Figure 6A:
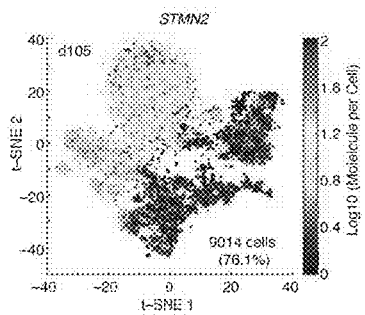
FIG. 6A-6L. t-SNE visualization of single cell gene expression of hCS and hSS at day 105 of differentiation (n=11,838 cells; BD Resolve system) (FIG. 6A) Distribution of expression of the neuronal marker STMN2, (FIG. 6B) the progenitor marker VIM and of (FIG. 6C) a set of genes associated with the M cell cycle phase (AURKB, TPX2, UBE2C, HMMR, TOP2A, CCNB1, NUSAP1, NUF2, CDCl$_6$, HIST1H4C, BIRC5, CKS2).
Figure 6B:
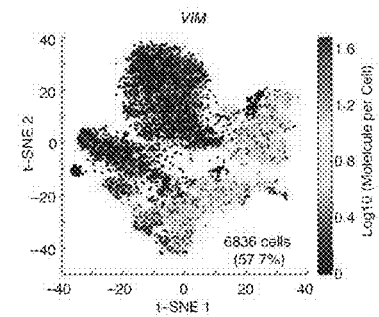
Figure 6C:
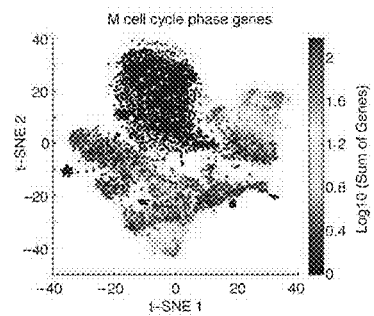
Figure 6D:
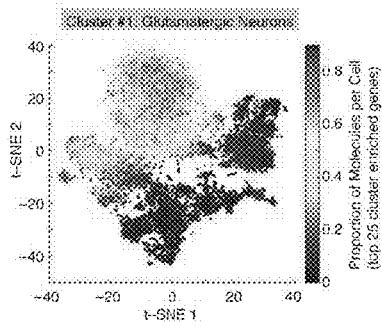
Figure 6E:
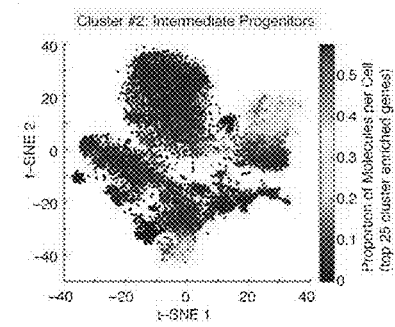
Figure 6F:
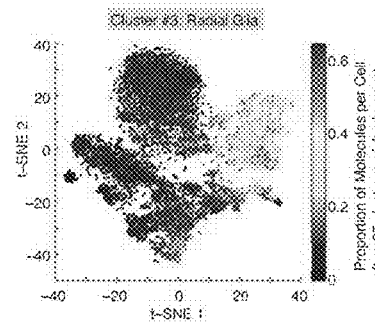
Figure 6G:
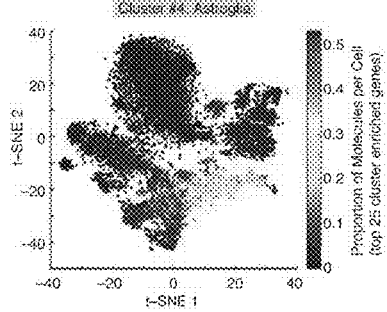
Figure 6H:
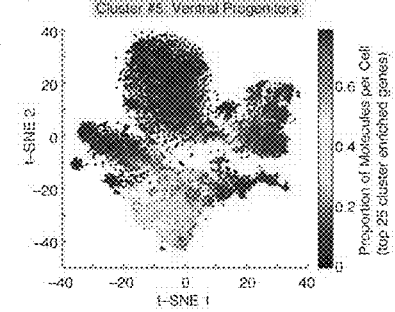
Figure 6I:
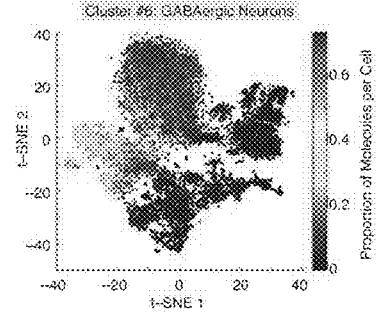
Figure 6J:
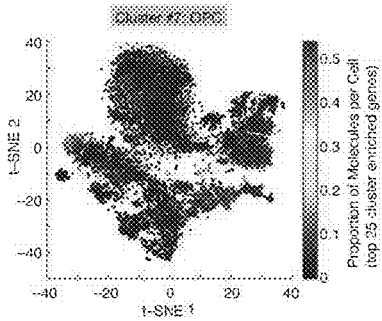
Figure 6K:
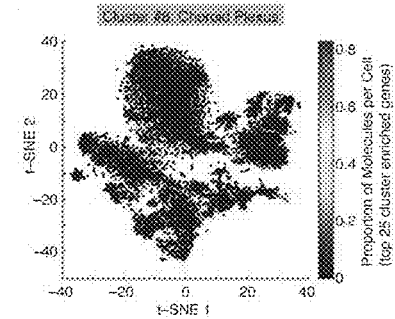
Figure 6L:
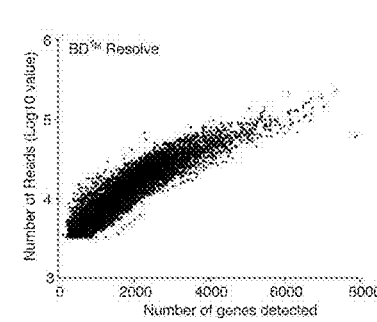

To more comprehensively characterize the population of cells in our 3D cultures, we performed highly-parallel, genome-wide single cell transcriptional profiling at day 105 of in vitro differentiation using next-generation sequencing with stochastic barcoding 18 (n=11,838 cells from hCS and hSS; BD Resolve system; FIG. 1i). Clustering and visualization using the t-Distributed Stochastic Neighbor Embedding (t-SNE)19 projection of cells isolated from either hCS or hSS, showed a clear separation of the two conditions. Neurons expressing STMN2 were localized on the upper left side of the t-SNE space while progenitors and mitotically active cells were distributed on the lower right side (FIG. 6a-c). Close examination of the single cell data indicated the presence of several subdomains in hCS (FIG. 1j, k), including a group of glutamatergic neurons (VGLUT1+) expressing the cortical layer markers TBR1, FEZF2, CTIP2; two groups of intermediate progenitors expressing TBR2, INSM1 and HES6; and a group of dorsal progenitors expressing LHX2, PAX6 and GLAST1 that also encompass HOPX+ outer radial glia-like cells (oRG). In contrast, hSS included a small group of oligodendrocyte progenitors (OLIG2, SOX10) and a cluster of ventral neural progenitors, as well as a group of GABAergic postmitotic cells expressing DLX1, GAD1, SLC32A1, SCG2, SST STMN2 (Table 2 lists the genes in each cluster; patterns of expression for the top 25 genes in each cluster are shown in FIG. 6d-k). Interestingly, astroglia from both hCS and hSS clustered together and close to a small group of cells resembling the choroid plexus and expressing TTR and SLC13A4. Moreover, a very small group of hCS-derived cells clustered with the GABAergic interneuron subdomain, and differential gene expression indicated that these cells expressed TBR1, RELN, PAX6 and CALB2. No cells of mesodermal or endodermal origin were found.

TABLE 2

SUPPLEMENTARY TABLE 2

| Gene | Forward primer | Reverse primer |
|---|---|---|
| ASCL1 | TCTTCGCCCGAACTGATGC | CAAAGCCCAGGTTGACCAACT |
| BRACH | TATGAGCCTCGAATCCACATAGT | CCTCGTTCTGATAAGCAGTCAC |
| CALB1 | AGGGAATCAAAATGTGTGGGAAA | TCCTTCAGTAAAGCATCCAGTTC |
| CALB2 | TTTGCAGACAAGCCAGGATG | TGTTTCACCGTGAACTGCAC |
| CHAT | ACATGATTGAGCGCTGCATC | ACTTGTCGTACCAGCGATTG |
| CXCR4 | TGTTGGCTGAAAAGGTGGTC | AACACAACCACCCACAAGTC |
| CXCR7 | ATCTTGAACCTGGCCATTGC | TGTGTGACTTTGCACGTGAG |
| DARPP32 | ATCCTCACCCTGTTTTGTGC | AGGTGGGCAAACAAGCAAAC |
| DLX1 | ATGCACTGTTTACACTCGGC | GACTGCACCGAACTGATGTAG |
| DLX2 | ACGGGAAGCCAAAGAAAGTC | TTTTGGAAACGCCGCTGAAG |
| DLX5 | TTCCAAGCTCCGTTCCAGAC | GAATCGGTAGCTGAAGACTCG |

TABLE 2-continued

SUPPLEMENTARY TABLE 2

| Gene | Forward primer | Reverse primer |
|---|---|---|
| EMX1 | CGCAGGTGAAGGTGTGGTT | TCCAGCTTCTGCCGTTTGT |
| ERBB4 | AACAATGTGACGGCAGATGC | TTCATGCAGGCAAAGCAGTC |
| FOXG1 | AACCTGTGTTGCGCAAATGC | AAACACGGGCATATGACCAC |
| GAD1 | ATGCAACCAGATGTGTGCAG | TGCCCTTTGCTTTCCACATC |
| GAPDH | CATGAGAAGTATGACAACAGCCT | AGTCCTTCCACGATACCAAAGT |
| GLI1 | ATGAAACTGACTGCCGTTGG | ATGTGCTCGCTGTTGATGTG |
| HOXB4 | TCCTCGTTTTCAGCTTTGGC | TCATTTGTTAGCGGGTGTCG |
| LHX6 | TGAGAGTCAGGTACAGTGCG | GCCCATCCATATCGGCTTTGA |
| LMX1B | AAACCCACGCAAACACACAC | TCTCTTTCTGACAAGGCAGGAC |
| MAFB | TGGCCGGATGCATTTTTGAG | AAGCACCATGCGGTTCATAC |
| MEIS2 | ACAGCTGGAGTGGCAAAAAG | AAATTGTCAAGCCCCCGAAC |
| MKX2-1 | AGCACACGACTCCGTTCTC | GCCCACTTTCTTGTAGCTTTCC |
| MKX6-2 | AGCACAAACCCTCGAACTTG | CCCCCGGATTCTGCAAAAATAG |
| NPY | CGCTGCGACACTACATCAAC | CAGGGTCTTCAAGCCGAGTT |
| OCT3/4 | CCCCAGGGCCCCATTTTGGTACC | ACCTCAGTTTGAATGCATGGGAGAGC |
| OLIG2 | GGACAAGCTAGGAGGCAGTG | ATGGCGATGTTGAGGTCGTG |
| PVALB | GGACAAAAGTGGCTTCATCGAG | TCGTCAACCCCAATTTTGCC |
| RAX1 | GGCCATCCTGGGGTTTACC | GGTCGAGGGGCTTCGTACT |
| RELN | TTTTTGACGGCTTGCTGGTG | TCCCAAATCCGAAAGCACTG |
| SIX3 | AGCAGAAGACGCATTGCTTG | ACCAGTTGCCTACTTGTGTG |
| SLC17A7 | TGCGCAAGTTGATGAACTGC | TCACGTTGAACCCAGAGATGG |
| SOX17 | GTGGACCGCACGGAATTTG | GGAGATTCACACCGGAGTCA |
| SOX2 | TTCACATGTCCCAGCACTACCAGA | TCACATGTGTGAGAGGGGCAGTGTGC |

The sequences in the left column (forward primers) from top to bottom are set forth in SEQ ID NOs: 1-34. The sequences in the right column (reverse primers) from top to bottom are set forth in SEQ ID NOs: 35-68.

TABLE 3

| Cluster | Gene |
|---|---|
| #1 | Glutamatergic Neurons |
| #1 | BCL11B (CTIP2) |
| #1 | BHLHE22 |
| #1 | CALB2 |
| #1 | CNTNAP2 |
| #1 | CRYM |
| #1 | FEZF2 |
| #1 | GAP43 |
| #1 | LMO3 |
| #1 | LMO7 |
| #1 | LPL |
| #1 | MAP1B |
| #1 | MAPT |
| #1 | MEF2C |
| #1 | NEUROD2 |
| #1 | NEUROD6 |
| #1 | NFIB |
| #1 | NRN1 |
| #1 | NSG2 |
| #1 | NTS |
| #1 | RTN1 |
| #1 | RUNX1T1 |
| #1 | SEZ6 |
| #1 | SLA |
| #1 | SLC17A7 (VGLUT1) |
| #1 | SPHKAP |
| #1 | STMN2 |
| #1 | SYT1 |
| #1 | TBR1 |
| #1 | THSD7A |
| #2 | Intermediate Progenitors |
| #2 | ASPM |
| #2 | CENPE |
| #2 | CENPF |
| #2 | EOMES (TBR2) |
| #2 | FAM64A |
| #2 | HES6 |
| #2 | HIST1H4C |
| #2 | HMGB2 |
| #2 | INSM1 |
| #2 | MKI67 |
| #2 | NHLH1 |
| #2 | PRC1 |
| #2 | RRM2 |
| #2 | SMC4 |
| #2 | TOP2A |
| #2 | TUBA1B |
| #2 | UBE2C |
| #3 | Radial Glia |
| #3 | AURKB |
| #3 | B3GAT2 |
| #3 | BIRC5 |
| #3 | C1orf61 |
| #3 | CDK1 |
| #3 | CENPF |
| #3 | COL11A1 |
| #3 | DMRTA2 |
| #3 | EMX2 |
| #3 | FABP7 |
| #3 | FAM107A |
| #3 | FAM64A |
| #3 | FZD8 |
| #3 | GINS2 |
| #3 | HIST1H4C |
| #3 | HOPX |
| #3 | ID4 |
| #3 | KIAA0101 |
| #3 | KIF15 |
| #3 | LHX2 |
| #3 | MCM4 |
| #3 | MKI67 |
| #3 | NUSAP1 |
| #3 | PAX6 |
| #3 | PRC1 |
| #3 | PTN |
| #3 | SFRP1 |
| #3 | SLC1A3 (GLAST-1) |
| #3 | SMC4 |

TABLE 3-continued

| Cluster | Gene |
| --- | --- |
| #3 | TOP2A |
| #3 | TPX2 |
| #3 | TUBA1B |
| #3 | VIM |
| #4 | Astroglia |
| #4 | ANXA2 |
| #4 | AQP4 |
| #4 | ATP1A2 |
| #4 | B2M |
| #4 | BCAN |
| #4 | CLU |
| #4 | CRISPLD1 |
| #4 | CRYAB |
| #4 | EDNRB |
| #4 | GPM6B |
| #4 | MLC1 |
| #4 | MT3 |
| #4 | NTN1 |
| #4 | NTRK2 |
| #4 | PI15 |
| #4 | PLTP |
| #4 | PMP2 |
| #4 | PTGDS |
| #4 | RAB31 |
| #4 | RSPO3 |
| #4 | SPARC |
| #4 | SPARCL1 |
| #4 | SPON1 |
| #4 | TAGLN2 |
| #4 | TIMP3 |
| #4 | TTYH1 |
| #4 | VCAM1 |
| #4 | VIM |
| #5 | Ventral Progenitors |
| #5 | BST2 |
| #5 | CRABP1 |
| #5 | CRABP2 |
| #5 | DDIT4 |
| #5 | DPPA4 |
| #5 | ENO1 |
| #5 | FAM60A |
| #5 | FTL |
| #5 | HMGA2 |
| #5 | HMGB2 |
| #5 | IGDCC3 |
| #5 | IRX2 |
| #5 | L1TD1 |
| #5 | LIN28A |
| #5 | LITAF |
| #5 | MDK |
| #5 | MIR302B |
| #5 | NMU |
| #5 | NR6A1 |
| #5 | PNP |
| #5 | PODXL |
| #5 | POU4F1 |
| #5 | PRDX6 |
| #5 | PRTG |
| #5 | QPRT |
| #5 | RPS6 |
| #5 | TPM2 |
| #5 | TRIM71 |
| #5 | TUBA1C |
| #6 | GABAergic Neurons |
| #6 | BEX5 |
| #6 | C22orf42 |
| #6 | CELF4 |
| #6 | CHGB |
| #6 | DIRAS3 |
| #6 | DLX1 |
| #6 | DLX5 |
| #6 | DLX6-AS1 |
| #6 | FGF14 |
| #6 | GAD1 |
| #6 | GAP43 |
| #6 | ISL1 |
| #6 | LHX6 |
| #6 | LHX8 |
| #6 | MAPT |
| #6 | NEFL |
| #6 | NEFM |
| #6 | NEGRI |
| #6 | NHLH2 |
| #6 | NNAT |
| #6 | NPAS4 |
| #6 | NSG2 |
| #6 | ONECUT2 |
| #6 | ONECUT3 |
| #6 | PBX3 |
| #6 | PCDH17 |
| #6 | PCP4 |
| #6 | PGM2L1 |
| #6 | POU2F2 |
| #6 | RELN |
| #6 | SCG2 |
| #6 | SCG5 |
| #6 | SIX3 |
| #6 | SLC32A1 |
| #6 | SPOCK2 |
| #6 | SPOCK3 |
| #6 | SST |
| #6 | STMN2 |
| #6 | STMN4 |
| #6 | SYT4 |
| #6 | TENM2 |
| #6 | TSHZ2 |
| #6 | ZCCHC12 |
| #7 | OPC |
| #7 | BCAN |
| #7 | BCAS1 |
| #7 | COL20A1 |
| #7 | EGFR |
| #7 | GPR17 |
| #7 | LHFPL3 |
| #7 | MBP |
| #7 | NNAT |
| #7 | OLIG1 |
| #7 | OLIG2 |
| #7 | PDGFRA |
| #7 | PMP2 |
| #7 | RAB31 |
| #7 | S100B |
| #7 | SCRG1 |
| #7 | SMOC1 |
| #7 | SOX10 |
| #8 | Choroid Plexus |
| #8 | CXCL14 |
| #8 | FOLR1 |
| #8 | IGF1 |
| #8 | IGFBP7 |
| #8 | PCP4 |
| #8 | PMCH |
| #8 | RBM47 |
| #8 | RP11-395L14.4 |
| #8 | SLC13A4 |
| #8 | TRPM3 |
| #8 | TTR |

Figure 7A:
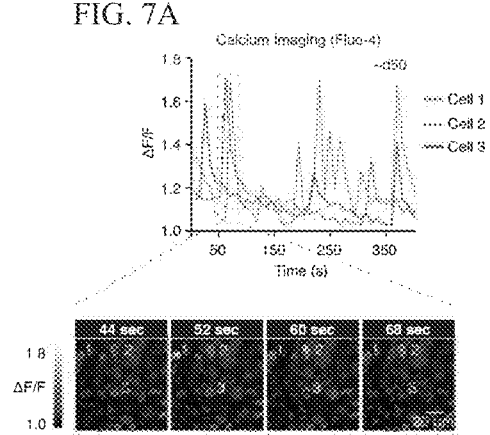
FIG. 7A-7B. Calcium imaging of intact hSS (Fluo-4).
Figure 7B:
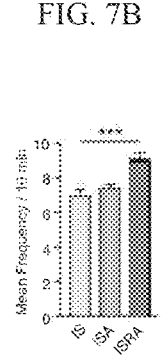
Figure 9A:
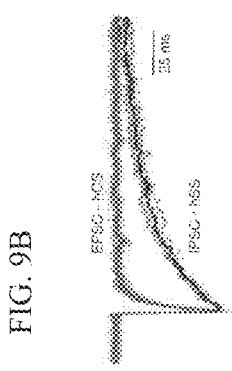
FIG. 9A-9B.
Figure 9B:
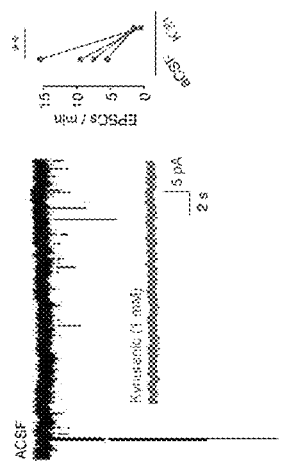

We next explored the functional properties of hSS using calcium imaging (Fluo-4) at approximately day 50 of differentiation. We found that 7 days of exposure to the neurosteroid and GABAA receptor agonist allopregnanolone (AlloP, 100 nM) combined with a short, 3-day exposure to retinoic acid (RA, 100 nM) (hSS-ISRA), significantly increased the frequency of spontaneous calcium spikes (P=0.006; FIG. 7a-b). Importantly, we found that exposure to AlloP with or without RA (hSS-ISA and hSS-ISRA, respectively) did not alter the subpallial fate, the neurotransmitter identity or the GABAergic subtypes in hSS (FIG. 8a-j). As a result, these two conditions were primarily used for subsequent experiments. In light of the observed spontaneous calcium activity and the presence of astrocytes in our spheroids (FIG. 1j), we investigated synaptogenesis in hSS using array tomography in 70 nm-thick sections. We found expression of the presynaptic protein synapsin-1 (SYN1) and the vesicular GABA transporter VGAT (FIG. 1*l*). Lastly, we used whole-cell patch clamping to record from neurons in 250 μm sections of hSS and found that ~75% of neurons generate action potentials in response to depolarization. At the same time, ~60% of neurons exhibit spontaneous inhibitory postsynaptic responses (sIPSCs) that reverse in direction around the chloride reversal potential and are abolished by the GABAA receptor antagonist gabazine (10 μM) (FIG. 1*m, n*; in contrast to synaptic currents in hCS as shown in FIG. 9*a*). Notably, the average shape of sIPSCs recorded in hSS displayed a prolonged decay as compared to the average EPSCs recorded from hCS, as is commonly observed in cortical neurons20 (FIG. 9*b*).

Figure 10A:
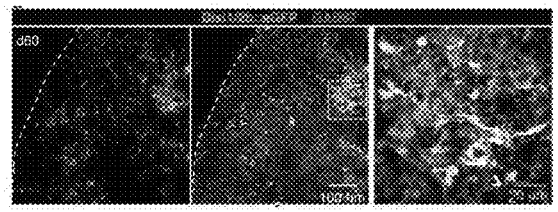
FIG. 10A-10T. Migration of Dlxi1/2::eGFP+ cells in fused hSS-hCS.
Figure 10B:
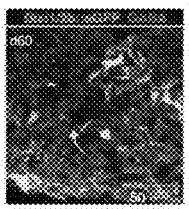
Figure 10C:
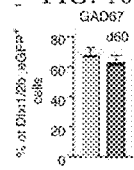
(FIG. 10C) Quantification by immunostaining of the proportion of Dlxi1/2::eGFP+ cells that co-express GAD67 in hSS derived using the ISA or ISRA condition (n=3 lines; t-test, $P=0.35$).
Figure 10D:
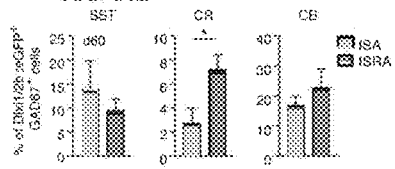
(FIG. 10D) Proportion of Dlxi1/2::eGFP+ cells in hSS derived using the ISA or ISRA condition that co-express somatostatin (SST, t-test, $P=0.48$), calretinin (CR, t-test, *$P=0.04$) or calbindin by immunostaining (CB, t-test, $P=0.43$); n=3 lines for SST, CR and CB quantifications.
Figure 10E:
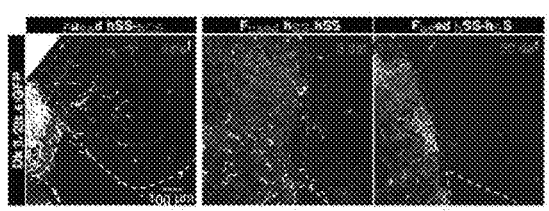
(FIG. 10E) Representative images of fused spheroids (at day 60) showing migration of Dlxi1/2b::eGFP+ cells (from labeled hSS) in fused hSS-hCS but not in hSS-hSS over time.
Figure 10F:
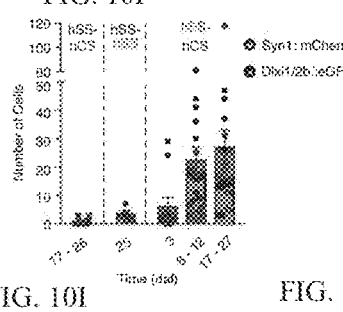
(FIG. 10F) The number of Dlxi1/2b::eGFP+(hSS-derived) or hSyn1::mCherry+ cells (hCS-derived) that moved in fused hSS-hCS or hSS-hSS was quantified in snapshots of live, intact spheroids at different time points (from day 3 to day 25). The values shown are absolute number of cells that migrated to the other side (approximately the same area and thickness was imaged in each session) (one-way ANOVA for cells at 17 days after fusion/assembly; $F(2, 32)=8.24$, $P=0.001$).
Figure 10G:
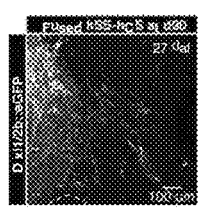
(FIG. 10G) Representative images of fused spheroids (at day 91) showing migration of Dlxi1/2b::eGFP+ cells (from labeled hSS) in fused hSS-hCS.
Figure 10H:
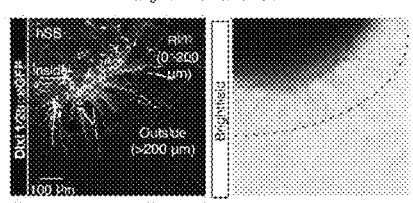
(FIG. 10H) Representative image of an hSS that was plated on a coverslip and cultured for ~7 days.
Figure 10I:
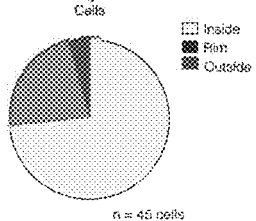
(FIG. 10I) Percentage of Dlxi1/2::eGFP inside the coverslip plated hSS and in the rim (0-200 μm) or beyond this region (>200 μm).
Figure 10J:
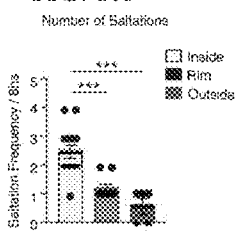
(FIG. 10J) Quantification of the number of saltations of Dlxi1/2b::eGFP+ cells (n=32) inside the one-week plated hSS, in the rim and outside this region (one-way ANOVA, interaction $F(2, 30)=22.12$, $P<0.001$; Bonferroni post-hoc ***$P<0.0001$).
Figure 10K:
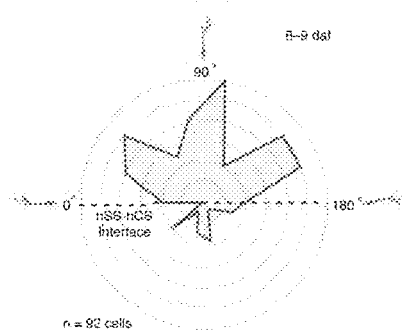
(FIG. 10K) Diagram showing the angle of movement of migrating Dlxi1/2b::eGFP+ cells at 8-9 days after fusion of hSS-hCS. The angle was calculated between the leading process of Dlxi1/2b::eGFP+ cells that have moved into hCS and the fusion interface (n=92 cells in 15 fused hSS-hCS from 5 hiPSC lines and 4 independent differentiations).
Figure 10L:
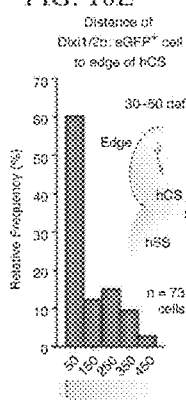
(FIG. 10L) Histogram showing the distribution of the distance of migrated Dlxi1/2b::eGFP+ cells relative to the edge of hCS in hSS-hCS at 30-50 days after fusion. The distance was measured in fixed 18 μm cryosections (n=73 cells from 11 fused hSS-hCS derived from 2 hiPSC lines in 2 independent differentiations).
Figure 10M:
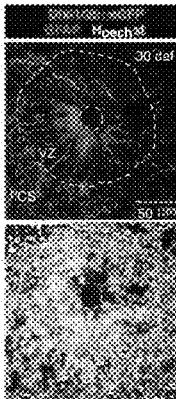
(FIG. 10M, 10N, 10O) Representative example of Dlxi1/2b::eGFP+ cells migrated in the hCS that moved within a ventricular zone-like (VZ) region. The VZ-like region shows GFAP-expressing cells, is surrounded by TBR1 expressing-cells and the migrated cells show GABA expression.
Figure 10N:
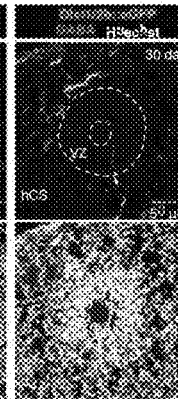
Figure 10O:
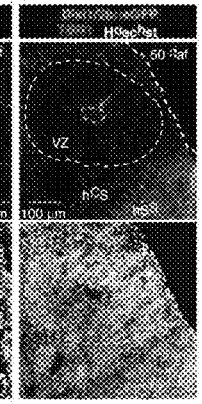
Figure 10P:
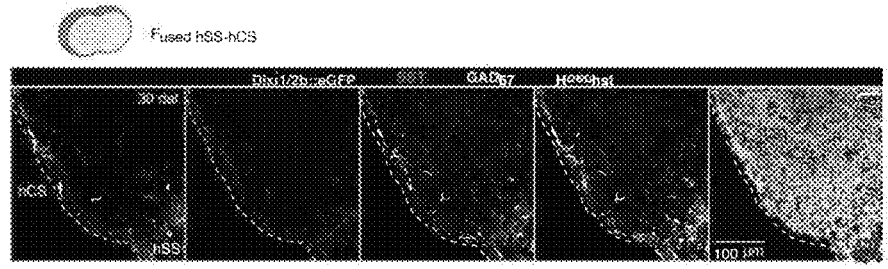
(FIG. 10P, 10Q, 10R, 10S) Representative images of immunostainings (SST, GAD67, GABA, CR, CB) of Dlxi1/2b::eGFP+ cells after migration in fused hSS-hCS.
Figure 10Q:
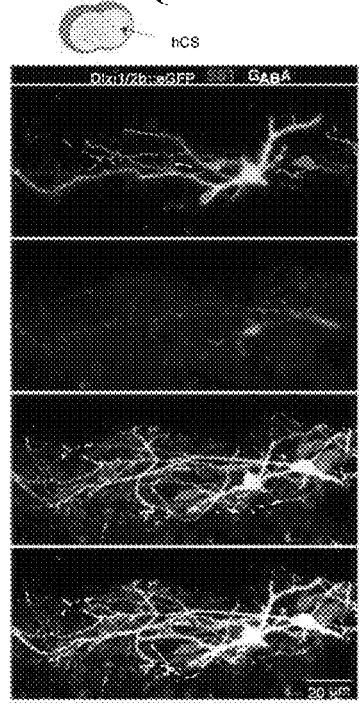
Figure 10R:
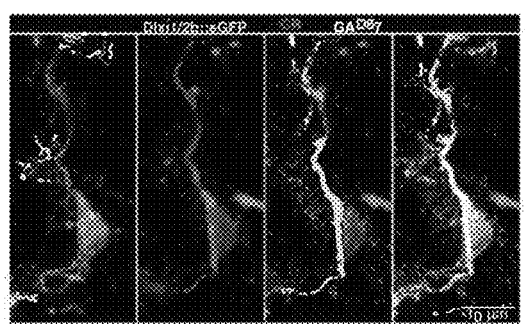
Figure 10S:
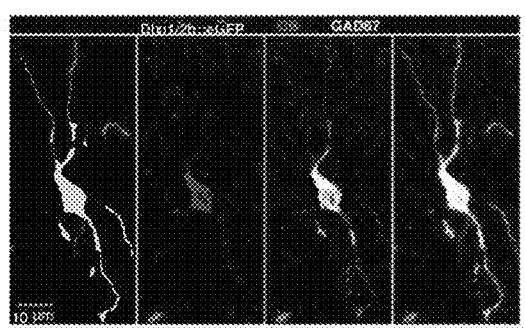

To develop a model for the migration of interneurons into the cerebral cortex, we placed one hCS and one hSS (~day 60) adjacent to each other into a 1.5 ml conical microcentrifuge tube (FIG. 2*a*). After 3 days the two spheroids fused (FIG. 2*b*). For these experiments, we used hCS at day 60 of differentiation resembling dorsal pallium at mid-gestation16, a developmental stage characterized by extensive migration of interneurons in vivo. Moreover, we employed viral labeling of spheroids before fusion to monitor cell migration; we used a previously described ultraconserved DNA element near the Dlx1 and Dlx2 locus (Dlxi1/2b) that labels the medial ganglionic eminences (MGE) and their derivatives21,22. Approximately 65% of Dlxi1/2b::eGFP cells in hSS expressed the GABA producing enzyme GAD67 and they contained GABA and markers for GABAergic neuron subtypes by immunocytochemistry (FIG. 10*a-d*). We then used live imaging under environmentally controlled conditions (37° C., 5% CO2) to monitor over several weeks the position of Dlxi1/2b::eGFP+ cells in fused hSS-hCS. We observed a progressive movement of eGFP+ cells from hSS into hCS over several weeks (FIG. 2*c*). This movement was specific to fused hSS-hCS and unidirectional: we observed minimal movement both from hCS into hSS in fused hSS-hCS and from hSS to hSS in fused hSS-hSS (FIG. 2*d*, FIG. 10*e, f*). The same pattern of fusion and migration could be observed for hSS-hCS assembled between day 60-90 of differentiation (FIG. 10*g*). Importantly, when hSS were plated on a coverslip the migration was inefficient or absent (FIG. 10*h-j*), similar to what has been reported in rodent cultures23. In the first 10 days after fusion, the vast majority of Dlxi1/2b::eGFP cells that migrated away from hSS had the leading process positioned towards hCS at either a 45° or 90° angle relative to the fusion interface (FIG. 10*k*). After 30-50 days post-fusion, 60% of the migrated cells were localized within the outer 100 μm of hCS (FIG. 10*l*), and overall, a large population of interneurons migrated into hCS as shown by optical clearing with iDISCO and reconstruction (FIG. 2*e*). Interestingly, we also observed processes of Dlxi1/2b::eGFP cells that briefly touched VZ-like regions containing progenitors in hCS, reminiscent of the ventricle-directed migration described in rodents (FIG. 10*m-o*). We next investigated the fate of Dlxi1/2b::eGFP cells in hSS and after 2 weeks of migration from hSS into hCS by isolating single cells from dissociated spheroids using Fluorescence Activated Cell Sorting (FACS) and Smart-seq2 for transcriptome analysis (FIG. 11*a*). We found that the majority of migrated cells expressed subpallial markers (DLX1, DLX2, DLX5, DLX6) and cortical interneuron markers (GAD1, GAD2, VGAT and CELF4) (FIG. 11*b*). We found few cells expressing PAX6 or TH, which are indicative of olfactory interneurons, or SP8, GSX2 or CHAT, which are indicative of striatal neurons, suggesting that the Dlxi1/2b reporter is primarily labeling cortical interneurons in hSS (FIG. 11*b*). Immunocytochemistry in fused hSS-hCS confirmed that the majority of migrated cells express SST (FIG. 10*p-s*).

We next used confocal imaging in 10-15 hrs long sessions to capture the movement of Dlxi1/2b::eGFP cells in fused hSS-hCS. Interneurons moved in a saltatory pattern followed by extensive pausing periods (FIG. 2*f*). This characteristic, cyclical movement involved an extension of the leading process in one direction followed by a transient swelling of the soma and nuclear translocation (FIG. 2*g, h*). This pattern of migration is similar to what has been observed in migrating interneurons in rodents25-27, although the ratio between the length of the leading process and the diameter of the soma in human hSS-derived interneurons is almost double the ratio in mouse interneurons, as quantified in mouse E18 slices imaged under similar conditions and using the same viral reporter (FIG. 12). To validate the pattern of interneuron migration observed in fused hSS-hCS, we performed live imaging of cells labeled with the Dlxi1/2b::eGFP reporter in human mid-gestation forebrain tissue (gestational weeks, GW18 and GW20; FIG. 2*i*). Dlxi1/2b::eGFP-labeled cells in fetal forebrain tissue co-expressed GABA and NKX2-1 (FIG. 12*a-f*) and we observed a similar cell morphology and cyclical pattern of migration that included long pausing periods and saltations following nucleokinesis (FIG. 2*j, k*; FIG. 12*g-l*).

Figure 10T:
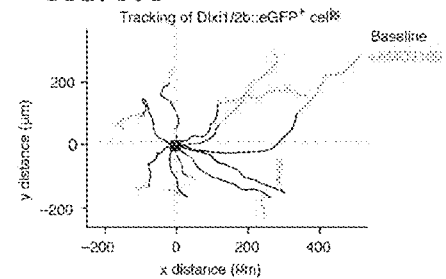
Figure 12A:
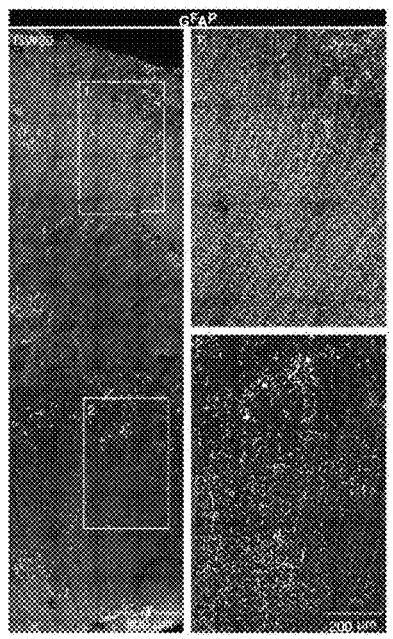
FIG. 12A-12L. Migration of Dlx2i1/2b::eGFP cells in mice brain slices and hSS-hCS.
Figure 12B:
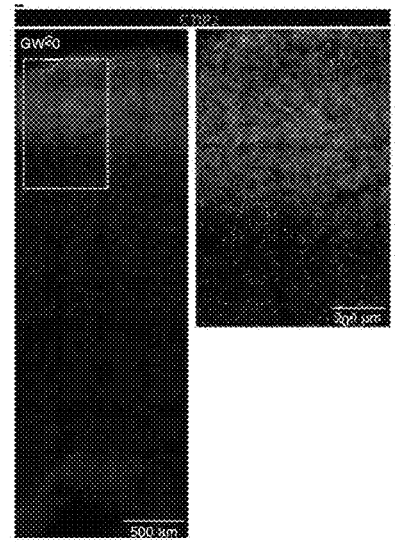
Figure 12C:
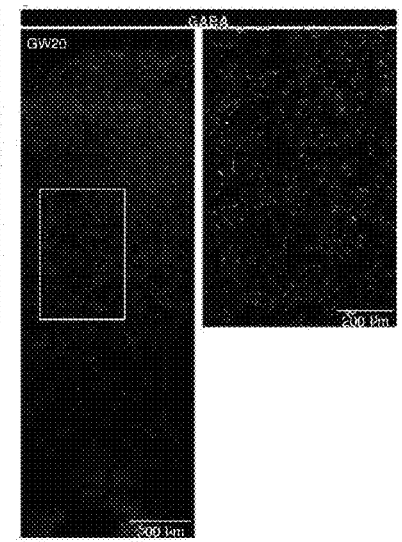
Figure 12D:
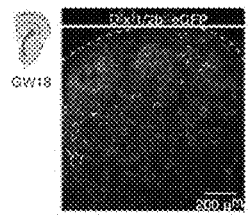
Figure 12E:
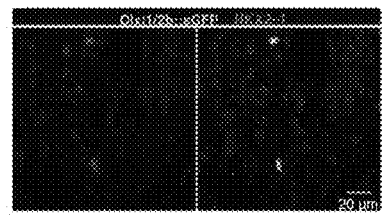
Figure 12F:
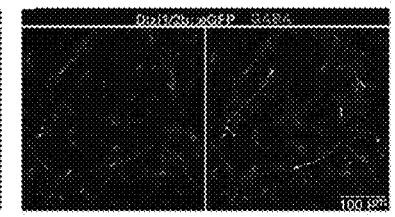
Figure 12G:
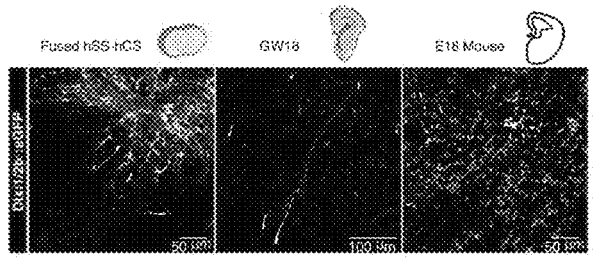
Figure 12H:
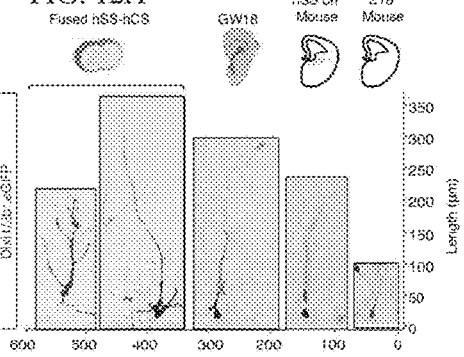
Figure 12I:
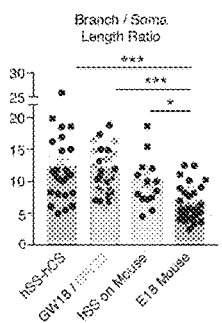
Figure 12J:
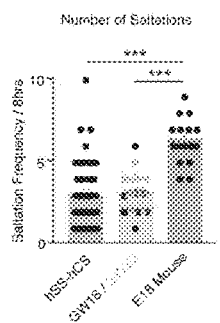
Figure 12K:
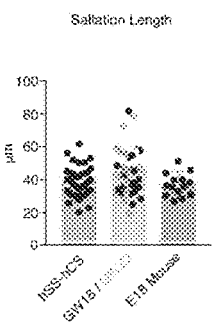
Figure 12L:
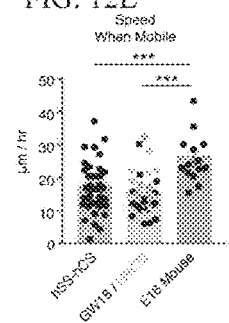

We tested whether we could pharmacologically manipulate interneuron migration in fused hSS-hCS (FIG. 2I). We imaged the movement of Dlxi1/2b::eGFP cells before and after exposure to a small molecule antagonist of the CXCR4 receptor (AMD3100, 100 nM). This receptor is expressed in hSS (FIG. 8*j*) as well as in migrating interneurons, and it has been shown to play a key role in the migration of cortical interneurons by binding to a ligand secreted in the dorsal pallium. Blocking the CXCR4 receptor resulted in a significant reduction in the frequency of saltations (FIG. 2*m*, P=0.03), the saltation length (FIG. 2*n*, P=0.006), the speed when mobile (FIG. 2*o*, P=0.006), and a change in the path directness (FIG. 2*p*, P=0.02; FIG. 10*t*).

We next investigated whether fused hSS-hCS could be used to model migration defects in neurodevelopmental disorders. Previous work in rodents has indicated that L-type voltage gated calcium channels (LTCC) play a critical role in interneuron migration by regulating the frequency of saltations and, ultimately, migration termination23. LTCC have been repeatedly associated with neuropsychiatric disease in genome-wide association studies31-33, and gain of function mutations in the LTC-encoding CACNA1C gene lead to Timothy syndrome (TS)—a severe neurodevelopmental disorder characterized by autism spectrum disorder and epilepsy9,10. We generated hSS and hCS from hiPSC from 3 patients with TS (7 hiPSC lines derived from 2 males and 1 female) carrying the same p.G406R point mutation (FIG. 3*a*) and compared them to 4 unaffected control subjects (4 hiPSC lines derived from 3 males and 1 female) (FIG. 13*a, b*; TS and control hiPSC lines used in various assays are shown in Table 1). We did not observe defects in the differentiation of TS hiPSC lines into hSS as assessed by gene expression and immunocytochemistry (FIG. 13*c-g*). Calcium imaging using the ratiometric dye Fura-2 showed increased residual calcium following depolarization in hSS-derived TS neurons versus control neurons (FIG. 3*b, c*; P<0.001), as well as in hCS-derived TS neurons compared to control cells (FIG. 13*h*; P<0.001), similar to what we have previously shown in TS hiPSC-derived glutamatergic neurons. We investigated the migration of Dlxi1/2b::eGFP cells in fused hSS-hCS (FIG. 3d; FIG. 13i) and found an increase in the frequency of saltations in neurons from all three TS patients (FIG. 3e; P<0.001; data by hiPSC lines shown FIG. 13j) in agreement with the role of calcium in promoting interneuron motility. Interestingly, the saltation length (FIG. 3f; P<0.001; data by hiPSC lines shown FIG. 13k) and the speed when mobile were reduced in TS as compared to controls (P<0.001; FIG. 13l) resulting in an overall less efficient migration (FIG. 3g; P<0.001). Moreover, this effect was cell-autonomous since migration of Dlxi1/2b::eGFP+ cells from TS-hSS into control-hCS did not influence the phenotype (FIG. 3e, f; FIG. 13j-1). To provide additional support for these results, we electroporated cDNA encoding TS- and WT-CaV1.2 into slices of mouse E14 ganglionic eminences and performed live imaging of GFP+ cells ~48 hrs later (FIG. 13m, n). Consistent with our findings in TS hSS-hCS, we observed a defect in mouse TS-CaV1.2 electroporated neurons displaying more frequent (FIG. 13o; P<0.01) but shorter saltations (FIG. 13p; P<0.001). To determine if the TS migratory phenotype was a result of LTCC activity and could be reversed, we treated fused hSS-hCS with LTCC blockers during imaging (FIG. 3h, i; FIG. 13q-t). Previous work in rodents has shown that pharmacological manipulation of LTCC influences interneuron migration23, and we found that application of the dihydropyridine LTCC blocker nimodipine (5 μM) significantly reduced saltation length and speed when mobile in control Dlxi1/2b::eGFP+ cells (P<0.001). However, the deficit in these parameters was rescued in TS Dlxi1/2b::eGFP+ cells following exposure to the LTCC antagonist (P<0.001). Moreover, roscovitine, a cyclin-dependent kinase inhibitor that increases voltage-dependent inactivation of CaV1.235,36 (15 μM), had a similar effect in rescuing saltation length in TS Dlxi1/2b::eGFP+ cells (P<0.001). These results indicate that the migration defect in interneurons carrying the TS gain-of-function mutation can be restored by reducing the activity of LTCC, which likely results in a higher probability and efficiency of Dlxi1/2b::eGFP saltations.

To investigate the hSS-derived neurons that migrated into the hCS network, we examined their single cell transcriptome at 4 weeks after hSS-hCS assembly using FACS and Smart-seq2 RNA-seq (n=181 single cells; FIG. 4a). t-SNE analysis indicated 3 main clusters (A-C; FIG. 4b), with Dlxi1/2b::eGFP+ cells in hSS distributed primarily in cluster A, while Dlxi1/2b::eGFP+ cells migrated into hCS primarily distributed in clusters B and C (FIG. 4c; χ2− test, χ2=43.39, P<0.0001). Cells in all clusters expressed similar levels of GAD1 and CELF4 (FIG. 11c), but cluster B and C down-regulated the subpallial marker PBX3. Migrated cells displayed expression changes in genes previously associated with interneuron migration such as ERBB4, NNAT, MALAT1, SOX11 and NXPH137,38 (FIG. 4d). Interestingly, migrated neurons also had higher levels of several activity dependent genes, including FOS, the AMPA-receptor trafficking regulator GRIP239 and the growth factor IGF140, as well as genes associated with neurodevelopmental disease (RASD141, TCF442) (FIG. 4d; FIG. 11c; Table 4).

TABLE 4

| A vs B and C | | B vs A and C | | C vs A and B | |
| --- | --- | --- | --- | --- | --- |
| Gene Name | P value | Gene Name | P value | Gene Name | P value |
| MEIS2 | 0 | SST | 0 | NNAT | 0 |
| NEFL | 0 | NNAT | 0 | UBB | 7.68E−14 |
| HSPA8 | 1.11E−16 | SOX11 | 0 | RP11-13811.4 | 2.97E−13 |
| MAB21L2 | 3.55E−15 | YWHAQ | 0 | NDUFA4 | 8.78E−13 |
| UCHL1 | 2.04E−14 | CPE | 0 | TMSB10 | 1.27E−12 |
| SOX4 | 3E−14 | MEIS2 | 0 | TINCR | 1.33E−12 |
| PGAM1 | 1.67E−13 | TCF4 | 1.44E−15 | LIN000689 | 1.25E−11 |
| CDC42 | 1.69E−13 | SOX4 | 3.66E−15 | CALM2 | 1.57E−11 |
| MAGED2 | 4.02E−13 | TMSB4XP8 | 5.33E−15 | A0017104.2 | 2.65E−11 |
| JAK3 | 4.49E−13 | TMSB4X | 5.88E−15 | RP5-1065J22.8 | 2.65E−11 |
| CHN1 | 1.47E−12 | VAT1L | 1.21E−14 | HSPA8 | 4.45E−11 |
| PLD3 | 2.27E−12 | ERBB4 | 1.17E−13 | DLX6 | 4.78E−11 |
| VDAC2 | 2.54E−12 | SLC26A11 | 1.46E−13 | STMN1 | 5.32E−11 |
| MDH1 | 2.68E−12 | PLCXD1 | 2.16E−13 | SAP30L-AS1 | 6.54E−11 |
| SORL1 | 2.82E−12 | SCG2 | 2.17E−13 | ATG2A | 1.12E−10 |
| CPE | 9.2E−12 | RP11-55K13.1 | 3.03E−13 | SIX6 | 1.82E−10 |
| COX5B | 1.05E−11 | NCALD | 3.14E−13 | SOX6 | 2.14E−10 |
| RP11-82023.2 | 1.36E−11 | ATPIF1 | 4.23E−13 | DOCK5 | 7.92E−10 |
| LRCH4 | 1.43E−11 | PLD3 | 2.5E−12 | RASD1 | 8.28E−10 |
| TCF4 | 1.65E−11 | AP000350.4 | 1.04E−11 | GHR | 9.24E−10 |
| MUC20 | 1.67E−11 | NEFL | 1.84E−11 | DLX6-AS2 | 1.35E−09 |
| DLX6-AS1 | 1.94E−11 | MTO1 | 2.04E−11 | ZFP64 | 1.97E−09 |
| PTPRB | 3.07E−11 | HAT1 | 2.08E−11 | TRABD2A | 2.41E−09 |
| PARK7 | 3.6E−11 | ZNF486 | 2.38E−11 | CHRNB1 | 2.49E−09 |
| YWHAZ | 6.62E−11 | PGAM1 | 5.55E−11 | NFIA | 2.63E−09 |
| SST | 9.22E−11 | BCAS4 | 5.97E−11 | FOS | 2.8E−09 |
| TTC39B | 1.2E−10 | PCDH9 | 9.26E−11 | LIPH | 3.05E−09 |
| DLX6 | 2.1E−10 | CEP41 | 1.18E−10 | RP11-814P5.1 | 3.32E−09 |
| ATP5O | 2.18E−10 | LHX6 | 1.33E−10 | MALAT1 | 3.72E−09 |
| RDH13 | 2.23E−10 | GNG3 | 1.59E−10 | RP11-379H18.1 | 5.15E−09 |
| SLC25A53 | 2.58E−10 | FAM189B | 5.7E−10 | MPP3 | 5.25E−09 |
| TMEM130 | 2.61E−10 | ZNF114 | 6.01E−10 | MAB21L2 | 5.97E−09 |
| DLX6-AS2 | 2.7E−10 | JUN | 7.41E−10 | NGRN | 1.14E−08 |
| CALM2 | 3.02E−10 | BSCL2 | 8.47E−10 | CTC-250I14.6 | 0.000000018 |
| SAP30L-AS1 | 4.29E−10 | GREB1 | 1.21E−09 | ZNF655 | 2.12E−08 |
| WDR31 | 5.26E−10 | MUC20 | 1.41E−09 | CTD-2293H3.1 | 2.46E−08 |
| PLA2G4C | 5.57E−10 | C16orf62 | 2.66E−09 | NDC80 | 2.55E−08 |
| PSMB5 | 6.99E−10 | TMSB4XP4 | 3.15E−09 | MRPS33 | 2.84E−08 |

TABLE 4-continued

| A vs B and C | | B vs A and C | | C vs A and B | |
|---|---|---|---|---|---|
| Gene Name | P value | Gene Name | P value | Gene Name | P value |
| GNG3 | 8.36E−10 | MIF | 3.31E−09 | RNF152 | 2.87E−08 |
| GATA3 | 8.59E−10 | HRK | 3.79E−09 | RBFOX2 | 3.43E−08 |
| DLX5 | 8.75E−10 | JDP2 | 3.98E−09 | SUOX | 3.52E−08 |
| RP11-128A17.1 | 8.95E−10 | AC009403.2 | 4.13E−09 | RORB | 4.28E−08 |
| CDH6 | 1.08E−09 | IGF1 | 5.7E−09 | GFRA1 | 4.67E−08 |
| PDE7B | 1.24E−09 | ATP1B1 | 6.48E−09 | SCG2 | 5.47E−08 |
| GTPBP2 | 1.4E−09 | TCTA | 6.93E−09 | RGS16 | 5.54E−08 |
| GOT1 | 1.46E−09 | SORL1 | 8.69E−09 | ROGDI | 0.000000067 |
| OPA3 | 1.61E−09 | TTC39B | 8.85E−09 | SOX4 | 0.000000103 |
| CISD2 | 2.05E−09 | EIF2AK2 | 9.74E−09 | HRK | 0.000000121 |
| GATM | 2.07E−09 | KB-1107E3.1 | 1.01E−08 | NMS | 0.000000125 |
| NUDC | 2.14E−09 | PLS3 | 1.06E−08 | EML6 | 0.00000015 |
| NFIB | 2.27E−09 | TSPAN3 | 1.11E−08 | YBX1 | 0.00000016 |
| CRABP1 | 2.34E−09 | ACBD4 | 1.11E−08 | SDCBP | 0.000000161 |
| RP11-977G19.11 | 2.82E−09 | PTPRG | 1.11E−08 | PPP1R17 | 0.000000212 |
| ZNF114 | 2.87E−09 | PKM | 1.17E−08 | ZNF225 | 0.00000024 |
| RP11-55K13.1 | 4.71E−09 | MTHFR | 1.21E−08 | EP400NL | 0.000000245 |
| MIEF2 | 4.97E−09 | ENO2 | 1.32E−08 | VPS29 | 0.000000277 |
| PRRT3 | 5.39E−09 | MYO15A | 1.43E−08 | TOX | 0.000000319 |
| GHR | 5.91E−09 | UCHL1 | 1.45E−08 | CYP20A1 | 0.000000364 |
| DTWD2 | 6.72E−09 | STPG1 | 1.47E−08 | FTH1 P16 | 0.000000403 |
| ANGPT2 | 7.1E−09 | GRIP2 | 1.59E−08 | BIRC5 | 0.000000414 |
| PLIN2 | 7.18E−09 | ZNF844 | 1.87E−08 | ACTB | 0.000000458 |
| ERBB4 | 7.32E−09 | CHN1 | 1.89E−08 | NETO2 | 0.000000521 |
| PDE4C | 8.23E−09 | STEAP4 | 3.19E−08 | TIPIN | 0.000000555 |
| DLX1 | 8.38E−09 | L1N000338 | 3.22E−08 | CRTC3 | 0.000000587 |
| AGT | 9.16E−09 | PDE7B | 3.46E−08 | EXOSC2 | 0.000000633 |
| C19orf40 | 9.41E−09 | TMEM130 | 3.49E−08 | CABP7 | 0.000000693 |
| RAB3B | 9.44E−09 | CALCOCO2 | 4.28E−08 | ATXN2 | 0.000000822 |
| TCTA | 1.01E−08 | JAK3 | 4.74E−08 | TMEFF2 | 0.000000886 |
| NACAD | 1.04E−08 | LGALS3BP | 0.000000054 | C8orf34 | 0.000000989 |
| TMSB4X | 1.19E−08 | DENND2A | 6.41E−08 | | |
| NGRN | 0.000000012 | CDH23 | 6.48E−08 | | |
| PCDH9 | 1.21E−08 | SLC22A17 | 6.59E−08 | | |
| HOTAIRM1 | 1.24E−08 | MLTK | 6.97E−08 | | |
| BSCL2 | 1.42E−08 | GFRA1 | 7.13E−08 | | |
| PPP1R13L | 1.45E−08 | TTL | 7.31E−08 | | |
| LHX5 | 1.47E−08 | CYCS | 7.32E−08 | | |
| TES | 1.69E−08 | AC104532.4 | 8.76E−08 | | |
| CADM2 | 1.83E−08 | FRMD4B | 9.97E−08 | | |
| TXNRD2 | 1.99E−08 | TMEM42 | 0.0000001 | | |
| STK17B | 2.29E−08 | AC137932.1 | 0.000000103 | | |
| DLX2 | 0.000000023 | VDAC2 | 0.000000106 | | |
| TMED3 | 2.43E−08 | STMN4 | 0.000000108 | | |
| SNAP25 | 2.49E−08 | RP11-82O23.2 | 0.000000108 | | |
| BTBD10 | 2.75E−08 | NXPH1 | 0.000000109 | | |
| NEFM | 2.78E−08 | CADM1 | 0.000000136 | | |
| PPP2R3B | 2.78E−08 | POC1B | 0.000000145 | | |
| RWDD2A | 2.89E−08 | LDHBP1 | 0.000000145 | | |
| WDR19 | 2.93E−08 | TACO1 | 0.000000151 | | |
| LIN000338 | 3.21E−08 | DUSP28 | 0.000000154 | | |
| ATG2A | 3.42E−08 | TSPYL2 | 0.000000155 | | |
| MTA3 | 3.45E−08 | CTC-359D24.3 | 0.000000162 | | |
| IFT20 | 3.55E−08 | FKBP2 | 0.000000169 | | |
| RWDD2B | 3.91E−08 | SLC16A3 | 0.000000176 | | |
| PSME2 | 0.000000042 | PCDH9-AS1 | 0.000000178 | | |
| AC040977.1 | 4.34E−08 | APLP1 | 0.000000187 | | |
| SOX11 | 4.36E−08 | CALY | 0.000000188 | | |
| RAB7L1 | 4.42E−08 | HYPK | 0.000000203 | | |
| GAS6-AS2 | 4.88E−08 | EHD4 | 0.000000215 | | |
| ATP6V1D | 5.47E−08 | FOS | 0.000000218 | | |
| ZNF486 | 5.53E−08 | ERVMER34-1 | 0.000000222 | | |
| APLP1 | 6.22E−08 | SLC25A34 | 0.000000258 | | |
| CATSPER2 | 6.35E−08 | ZNF154 | 0.000000295 | | |
| CISD1 | 6.81E−08 | SFMBT2 | 0.00000031 | | |
| AC004453.8 | 6.94E−08 | RDH13 | 0.000000322 | | |
| YWHAB | 6.96E−08 | PARK7 | 0.00000035 | | |
| ZNF772 | 7.78E−08 | RBP1 | 0.00000035 | | |
| RP5-1065J22.8 | 8.81E−08 | JUND | 0.000000368 | | |
| POR | 9.15E−08 | CLSPN | 0.000000375 | | |
| ALDOC | 9.49E−08 | SPARC | 0.000000376 | | |
| ZC3H12B | 0.000000104 | LRCH4 | 0.000000401 | | |
| ARF5 | 0.000000104 | APAF1 | 0.000000413 | | |
| SMTN | 0.000000105 | ZBTB3 | 0.000000421 | | |
| NDUFC1 | 0.00000011 | TWSG1 | 0.000000438 | | |
| ATRN | 0.000000116 | L1NC00689 | 0.000000441 | | |

TABLE 4-continued

| A vs B and C | | B vs A and C | | C vs A and B | |
|---|---|---|---|---|---|
| Gene Name | P value | Gene Name | P value | Gene Name | P value |
| BEX5 | 0.000000124 | PAWR | 0.000000479 | | |
| LINC00689 | 0.000000137 | CAPZA1 | 0.000000513 | | |
| ZNF385D | 0.000000144 | TAPBP | 0.000000529 | | |
| GPX3 | 0.000000147 | MAB21L1 | 0.000000563 | | |
| LAMP5 | 0.000000151 | AHI1 | 0.000000565 | | |
| JDP2 | 0.000000159 | TMEM205 | 0.00000057 | | |
| LINC01102 | 0.000000161 | LIPH | 0.000000591 | | |
| SEPT4 | 0.000000162 | ARHGAP44 | 0.000000598 | | |
| TACO1 | 0.000000163 | SRP14-AS1 | 0.000000662 | | |
| ATP5G1 | 0.000000167 | CDC42 | 0.000000697 | | |
| MICALL1 | 0.000000174 | RP11-192H23.5 | 0.000000707 | | |
| TUBA4A | 0.000000179 | DYNC1I1 | 0.000000791 | | |
| CLTB | 0.000000181 | PTPRF | 0.000000816 | | |
| RP11-192H23.5 | 0.000000183 | CLU | 0.000000818 | | |
| SEMA4C | 0.000000187 | PURB | 0.00000083 | | |
| MEIS1 | 0.000000192 | PRRT3 | 0.000000831 | | |
| DYNLT1 | 0.000000199 | PGRMC1 | 0.000000852 | | |
| HSPA9 | 0.000000202 | TES | 0.00000089 | | |
| TMSB4XP8 | 0.000000215 | GOT1 | 0.000000899 | | |
| CYCS | 0.000000239 | CX3CL1 | 0.000000981 | | |
| TMEM120A | 0.000000241 | | | | |
| ACTA2 | 0.000000268 | | | | |
| SPOCK3 | 0.000000276 | | | | |
| SUMF2 | 0.000000286 | | | | |
| PBX3 | 0.000000288 | | | | |
| DOCK5 | 0.000000295 | | | | |
| ZNF225 | 0.000000297 | | | | |
| TMSB10 | 0.000000304 | | | | |
| RNF181 | 0.000000321 | | | | |
| AC027763.2 | 0.000000338 | | | | |
| C14orf166 | 0.000000358 | | | | |
| FAIM2 | 0.00000037 | | | | |
| CDH13 | 0.000000387 | | | | |
| PSTPIP2 | 0.000000405 | | | | |
| RP11-178G16.4 | 0.000000409 | | | | |
| MGST3 | 0.00000041 | | | | |
| IDH3B | 0.000000414 | | | | |
| GULP1 | 0.000000415 | | | | |
| TMEM216 | 0.000000417 | | | | |
| PARVA | 0.000000417 | | | | |
| GS1-72M22.1 | 0.000000418 | | | | |
| TMEM205 | 0.00000043 | | | | |
| NAP1L5 | 0.000000436 | | | | |
| C21orf33 | 0.000000437 | | | | |
| TMEM132B | 0.000000447 | | | | |
| WDR55 | 0.000000475 | | | | |
| PSMD12 | 0.000000479 | | | | |
| STMN4 | 0.000000483 | | | | |
| CHRD | 0.000000506 | | | | |
| MOAP1 | 0.000000509 | | | | |
| CTB-60E11.9 | 0.000000524 | | | | |
| ATF7IP2 | 0.000000535 | | | | |
| RNF5 | 0.000000536 | | | | |
| LRRC36 | 0.000000541 | | | | |
| MRPL22 | 0.000000545 | | | | |
| OTUD6B | 0.000000557 | | | | |
| TMEM106A | 0.000000566 | | | | |
| PSMB1 | 0.000000581 | | | | |
| SUMF1 | 0.000000585 | | | | |
| PSMD13 | 0.000000611 | | | | |
| RAB3C | 0.00000062 | | | | |
| PGM2L1 | 0.000000633 | | | | |
| DNAJC17 | 0.000000639 | | | | |
| ZCCHC17 | 0.000000643 | | | | |
| PPA2 | 0.000000665 | | | | |
| RBP1 | 0.000000668 | | | | |
| PDP2 | 0.000000668 | | | | |
| MLEC | 0.000000694 | | | | |
| CARD14 | 0.000000696 | | | | |
| ATP1B1 | 0.000000702 | | | | |
| NDE1 | 0.000000709 | | | | |
| TMED9 | 0.000000735 | | | | |
| KB-1107E3.1 | 0.000000743 | | | | |
| CCDC167 | 0.000000758 | | | | |
| ATP6V1A | 0.00000077 | | | | |
| B3GNT1 | 0.000000774 | | | | |

TABLE 4-continued

| A vs B and C | | B vs A and C | | C vs A and B | |
| --- | --- | --- | --- | --- | --- |
| Gene Name | P value | Gene Name | P value | Gene Name | P value |
| MATR3 | 0.000000808 | | | | |
| TUBB2A | 0.000000884 | | | | |
| DNAH9 | 0.00000089 | | | | |
| GPRC5A | 0.000000903 | | | | |
| USP11 | 0.000000935 | | | | |
| TUBB4A | 0.000000984 | | | | |

Figure 14A:
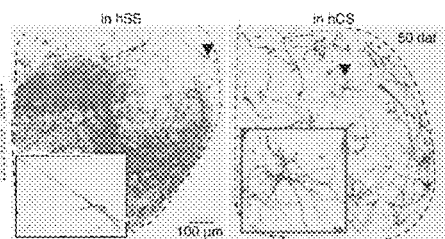
FIG. 14A-14F. Characterization of Dlxi1/2b::eGFP+ cells after migration (FIG. 14A) Representative images of 3D-reconstructed Dlxi1/2b::eGFP+ cell morphologies before and after migration from hSS into hCS.
Figure 14B:
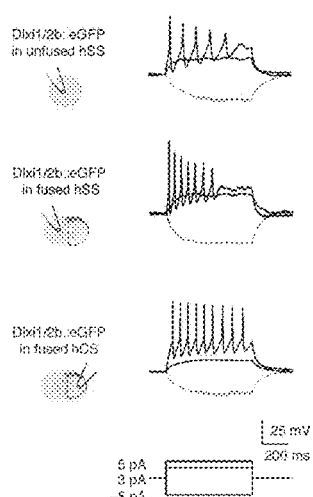
Figure 14C:
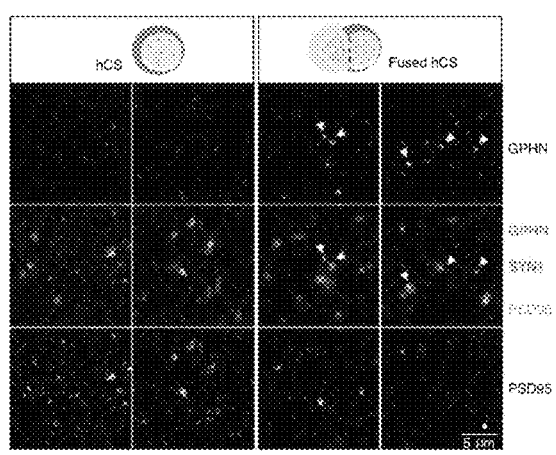
Figure 14D:
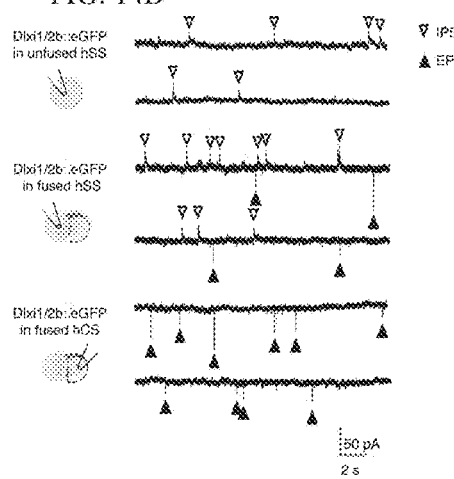
Figure 14E:
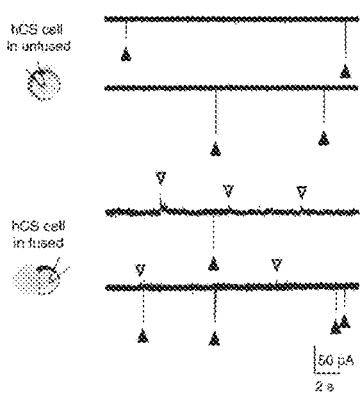
Figure 14F:
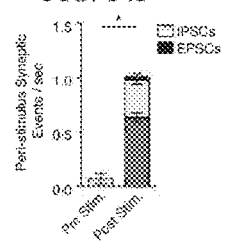

To further investigate integration of migrated hSS-derived, we examined the dendritic morphology of Dlxi1/2b::eGFP+ cells in hSS and in fused hSS-hCS. We found that the mostly bipolar hSS-derived cells that moved into hCS increased the complexity of their dendritic branching (FIG. 4e, f; P<0.001; FIG. 14a). We then measured their electrical properties in hSS before and after fusion by quantifying action potential generation in response to steps of depolarizing current. We found that Dlxi1/2b::eGFP+ cells that had migrated into hCS had double the maximum action potential generation rate as compared to Dlxi1/2b::eGFP+ cells in unfused hSS or to non-migrated Dlxi1/2b::eGFP+ cells in fused hSS-hCS (FIG. 4g; P<0.001; FIG. 14b). We then assessed the synaptic integration of migrated neurons by using array tomography to detect pre- and post-synaptic proteins in hCS before and after fusion to hSS, and observed the presence of gephyrin (GPHN), a postsynaptic protein localized to GABAergic synapses, in hCS fused to hSS but not unfused hCS (FIG. 14c). To further examine these synaptic puncta in fused hSS-hCS, we constructed 'synaptograms' consisting of a series of high-resolution sections through a single synapse, and found colocalization of eGFP from Dlxi1/2b labeled cells with the presynaptic proteins SYN1 and VGAT as well as the postsynaptic protein GPHN (FIG. 4h-i). To investigate the presence of functional synapses in migrated Dlxi1/2b::eGFP neurons, we sliced fused hSS-hCS into 250 µm sections and performed whole-cell voltage clamp recordings of synaptic responses. To reliably distinguish between excitatory postsynaptic currents (EPSCs, downward deflecting) and IPSCs (upward deflecting), we used a low Cl− solution in the patch pipette and held the cells at −50 mV. We found that Dlxi1/2b::eGFP that migrated into hCS display both EPSCs and IPSCs (FIG. 4j). Moreover, after migration into hCS, these cells primarily receive EPSCs rather than IPSCs and their synaptic input increases approximately 3-fold (FIG. 4k, P<0.001; FIG. 14d; electrical properties of patched cells are shown in Table 5). In parallel, glutamatergic neurons from hCS, which exhibit only EPSCs before fusion, also begin receiving IPSCs and show an overall increase in synaptic input following the migration of interneurons from hSS (FIG. 4l, FIG. 14e, P<0.05). Lastly, in order to assess the functional integration of hCS and hSS neurons into neural networks, we applied electrical stimulation to the hCS side of fused hSS-hCS to trigger glutamate release from excitatory neurons in the vicinity of the stimulation electrode while simultaneously recording EPSCs and IPSCs in Dlxi1/2b::eGFP cells that migrated into hCS (FIG. 4m; FIG. 14f). We found that electrical simulation evoked EPSCs (eEPSCs) immediately following simulation (>5 ms); this was followed by presumed disynaptic IPSCs (<15 ms) sensitive to gabazine, suggesting the assembly of a 3D cortical microphysiological system that incorporates both excitatory and inhibitory synaptic activity.

TABLE 5

SUPPLEMENTARY TABLE 5

| | RMP* | Rheobase | Threshold | Max Spike/Sec | Overshoot | Half-Width | EPSPs/min | IPSPs/min | n |
| --- | --- | --- | --- | --- | --- | --- | --- | --- | --- |
| DIxi1/2b::eGFP neurons in hSS | −61.8 ± 3.2 | 6.1 ± 0.7 | −46.8 ± 4.2 | 3.1 ± 0.6 | 8.6 ± 1.6 | 4.2 ± 0.3 | 2.0 ± 0.7 | 8.7 ± 1.6 | 11 |
| DIxi1/2b::eGFP neurons in hCS | −66.4 ± 4.7 | 5.6 ± 0.7 | −49.3 ± 5.0 | 6.8 ± 1.0 | 15.6 ± 2.1 | 3.8 ± 0.2 | 15.5 ± 2.2 | 3.6 ± 1.0 | 11 |
| DIxi1/2b::eGFP neurons in unfused | −63.4 ± 2.9 | 6.2 ± 0.9 | −42.5 ± 3.2 | 2.8 ± 0.5 | 12.2 ± 1.6 | 3.9 ± 0.4 | 0.4 ± 0.2 | 5.5 ± 1.8 | 15 |
| hCS neurons in fused | −61.2 ± 4.3 | 6.6 ± 1.1 | −41.7 ± 3.9 | 4.5 ± 1.0 | 10.8 ± 0.8 | 5.8 ± 0.7 | 11.0 ± 1.7 | 6.8 ± 2.3 | 9 |
| hCS neurons in unfused | −59.8 ± 3.9 | 8.8 ± 1.4 | −44.7 ± 4.3 | 4.2 ± 0.7 | 10.5 ± 1.2 | 6.2 ± 0.8 | 8.3 ± 2.0 | 0.2 ± 0.2 | 6 |

*Resting Membrane Potential

In this study, we show the generation of a human 3D microphysiological system (MPS) that includes functionally-integrated excitatory glutamatergic and GABAergic neurons. This platform has several advantages in comparison to previous methods for deriving organoids or cortical interneurons in adherent conditions. First, it involves the directed differentiation of subdomains of the forebrain that functionally interact in development. In contrast to whole-brain organoids and organoids resembling broader brain regions, this approach allows for modularity by combining separately patterned spheroids into multi-region neural 3D cultures. Second, this system captures in vitro more elaborate processes during CNS development, including the saltatory migration of interneurons towards the cerebral cortex. Using live imaging of the mid-fetal human forebrain, we demonstrate that this saltatory interneuron migration is accurately recapitulated with this assembled 3D platform.

Third, by enabling their migration into an active neural network, interneurons mature and integrate into a synaptically connected microphysiological system without the requirement of seeding onto rodent cortical cultures or brain slices. Assembling networks using this modular system may facilitate the study of excitation to inhibition interplay during cortical development.

We also demonstrate that forebrain subdomains derived from hiPSCs and fused in vitro can be used to identify the transcriptional changes associated with interneuron migration and to model disease processes that take place in mid to late human fetal development and are otherwise inaccessible. We find that cortical interneurons derived from TS subjects carrying a mutation in the $Ca_V1.2$ channel display a cell-autonomous migration defect whereby they move more frequently but less efficiently. Moreover, the abnormal migration in TS cultures is rescued by pharmacologically manipulating voltage-gated calcium channels, further demonstrating the key role of calcium signaling in cortical assembly. This aberrant interneuron migration taken together with our previous studies showing defects in cortical excitatory neurons, suggest the presence of abnormal cortical development and function in TS.

Lastly, the specification in vitro of various subdomains of the developing human brain from hPSC and their assembly into 3D cultures, opens the opportunity for studying the interaction of specific neuronal cell types and for generating and probing microphysiological systems that includes neural circuits.

Material and Methods

Culture of hiPSCs. The lines of hiPSC used in this study were validated using standardized methods as previously shown. Cultures were tested for and maintained *Mycoplasma* free. A total of 6 control iPSC lines derived from 5 subjects, plus the human embryonic stem cell line H9, and 7 hiPSC lines derived from 3 subjects with TS carrying the pG406R mutation were used for experiments (Table 1). The TS point mutation in exon 8a of CACNA1C was verified by PCR as previously described. The hiPSC line H20961 was derived by the Gilad laboratory. Approval for this study was obtained from the Stanford IRB Panel and informed consent was obtained from all subjects.

Generation from hiPSC of hCS and hSS. Human pluripotent stem cells (hiPSC or hESC) were cultured on inactivated mouse embryonic fibroblast feeders (EmbryoMax PMEF; Millipore) in hPSC medium containing DMEM/F12 (1:1, Life Technologies, 11330), Knockout Serum (20%, Life Technologies, 10828), non-essential amino acids (1 mM, Life Technologies, 11140), GlutaMax (1:200, Life Technologies, 35050), β-mercaptoethanol (0.1 mM; Sigma-Aldrich M3148), penicillin and streptomycin (1:100, Life Technologies, 15070), and supplemented with FGF2 (10 ng/ml diluted in 0.1% BSA; R&D Systems).

The generation of hCS from hiPSC was performed as previously described. To initiate the generation of hCS or hSS, intact hiPSC colonies were lifted from the plates using dispase (0.35 mg/ml) and transferred into ultralow attachment plastic dishes (Corning) in hPSC medium supplemented with the two SMAD inhibitors dorsomorphin (DM; 5 µM; Sigma) and SB-431542 (SB; 10 µM, Tocris), and the ROCK inhibitor Y-27632 (10 µM; EMD Chemicals). For the first five days, the hPSC medium was changed every day and supplemented with dorsomorphin and SB-431542. On the sixth day in suspension, neural spheroids were transferred to neural medium (NM) containing Neurobasal-A (Life Technologies, 10888), B-27 supplement without vitamin A (Life Technologies, 12587), GlutaMax (Life Technologies, 1:100), penicillin and streptomycin (Life Technologies, 1:100) and supplement with the growth factors EGF (20 ng/ml; R&D Systems) and FGF2 (20 ng/ml; R&D Systems) until day 24. For the generation of hSS, the medium was supplemented with additional small molecules during the first 23 days in culture; a schematic showing the recipes is presented in FIG. 8a). The hSS-IS condition involved the addition of the Wnt pathway inhibitor IWP-2 (5 µM; Selleckchem) from day 4 until day 24, and the SHH pathway agonist SAG (smoothened agonist; 100 nM; Selleckchem) from day 12 to day 24. The hSS-ISA condition also included IWP2 and SAG with the addition of allopregnanolone (AlloP 100 nM; Cayman Chemicals) from day 15 to day 23, while the hSS-ISRA condition included AlloP (100 nM) from day 15-23, and a brief exposure (day 12-15) to retinoic acid (RA 100 nM; Sigma). From day 25 to 42, the NM for both the hCS and hSS conditions, was supplemented with the growth factors BDNF (20 ng/ml; Peprotech) and NT3 (20 ng/ml; Peprotech) with medium changes every other day. From day 43 onwards, hCS and hSS were maintained in unsupplemented NM with medium changes every four to six days.

Viral labeling and fusion of neural spheroids. hCS or hSS were transferred to a 1.5 ml Eppendorf tube containing 300 µl NM with virus and incubated overnight. The next day, neural spheroids were transferred into fresh NM medium in ultralow attachment plates. Lentivirus (*Lenti*-Dlxi1/2b::eGFP) was generated by transfecting HEK293T cells with Lipofectamine 2000 (Thermo Fisher Scientific) and concentrating the supernatant with the *Lenti*-X concentrator (Clontech) 72 hrs later. Adenovirus (AAV-DJ1-hSyn1::mCherry) was generated in the Stanford Gene Vector and Virus Core at Stanford.

To fuse the forebrain spheroids, hCS and hSS (~60 to 90 days of in vitro differentiation), which were virally labeled 8-10 days before, were transferred to a 1.5 ml Eppendorf tube for three days and placed in an incubator. During this time, more than 95% of hCS and hSS fused. These hSS-hCS cultures were carefully transferred into 24 well ultralow attachment plates (Corning) using a cut P-1000 pipette tip and medium changes were performed very gently every two to three days.

Cryopreservation. hCS were fixed in 4% paraformaldehyde (PFA) and 8% sucrose for 30 min to 2 hrs. They were then washed in PBS, transferred to 15% sucrose solution over night at 4° C. and then to 30% sucrose for 48-72 hrs. Subsequently, they were transferred into embedding medium (Tissue-Tek OCT Compound 4583, Sakura Finetek), snap-frozen on dry ice and stored at −80° C. For immunohistochemistry, 10 to 20 µm thick sections were cut using a cryostat (Leica). Human brain tissue was fixed in 4% PFA for 48 hrs, washed in PBS and transferred to 30% sucrose for one week. Sections were then embedded in OCT and 30% sucrose (1:1) and sectioned into 40 µm sections using a Leica cryostat.

Immunohistochemistry. Cryosections were washed with PBS to remove excess OCT and blocked in 10% goat serum (NGS), 0.3% Triton X-100 diluted in PBS for 1 hr at room temperature. The sections were then incubated overnight at 4° C. with primary antibodies diluted in PBS containing 10% GS and 0.3% Triton X-100. PBS was used to wash off the primary antibodies and the cryosections were incubated with secondary antibodies in PBS with 10% NGS and 0.3% Triton X-100 for 1 hr. The following primary antibodies were used for immunohistochemistry: anti-NKX2.1 (rabbit, 1:200; Santa Cruz: sc-13040), anti-MAP2 (guinea pig, 1:1000; Synaptic Systems: 188004), anti-GABA (rabbit, 1:1000; Sigma: A2052), anti-GAD67 (mouse, 1:1000; Millipore: MAB5406), anti-SST (rat, 1:200; Millipore: MAB354), anti-CR (rabbit, 1:1000; Swant: CR7697), anti-CB (rabbit, 1:1000; Swant: CB38), anti-PV (rabbit, 1:6000; Swant: PV27), anti-PV (mouse 1:1000; Millipore: MAB1572), anti-GFP (chicken, 1:1500; GeneTex: GTX13970), anti-DCX (guinea pig, 1:1000; Millipore: AB2253); anti-TBR1 (rabbit, 1:200; Abcam: AB31940), anti-GFAP (rabbit, 1:1000; DAKO Z0334), anti-CTIP2 (rat, 1:300; Abcam: AB18465), anti-OCT4 (rabbit, 1:200, Cell Signaling Technology), anti-SSEA4 (mouse, 1:200, Cell Signaling Technology). AlexaFluo Dyes (Life Technologies) were used at 1:1000 dilution for amplifying the signal. Nuclei were visualized with Hoechst 33258 (Life Technologies). Cryosections were mounted for microscopy on glass slides using Aquamount (Thermo Scientific) and imaged on a Zeiss M1 Axioscope or Leica TCS SP8 confocal microscope. Images were processed in ImageJ (Fiji).

Dissociation of hCS and hSS. For the enzymatic dissociation of hCS and hSS for culture in monolayer and immunocytochemistry, spheroids were incubated with Accutase (Innovative Cell Technologies) for 25 min at 37° C., washed with NM and gently triturated using a P-200 pipet. Cells were plated on poly-ornithine/laminin (Sigma) coated glass coverslips (15 mm; Werner) at a density of ~1 spheroid per two coverslips in NM supplemented for BDNF and NT3. To dissociate hCS and hSS for single cell profiling, we adapted a previously published protocol used for primary human fetal brain tissue 52. Briefly, up to 6 spheroids were chopped using a #10 blade and then incubated in papain enzyme solution (27.3 U/ml; Worthington), EBSS (1×, Sigma), 0.46% Sucrose (Sigma), 26 mM $NaHCO_3$(Sigma), 0.5 mM EDTA (Sigma) at 37° C. for 70 min in an incubator (5% $CO2$). The digested spheroids were then washed and carefully triturated in a trypsin inhibitor solution EBSS, 0.46% Sucrose (Sigma), 26 mM $NaHCO_3$(Sigma), 15-30 mg Trypsin Inhibitor (Sigma). After centrifugation, the pellet was resuspended in 0.2% BSA diluted in PBS and supplemented with Y-27632 (10 µM; EMD Chemicals) and the cells were used for FACS.

Mouse slice cultures. Whole brains from E14-E18 mouse embryos were embedded in 4% low-melting point agarose and slices were cut at 250-300 µm using a Leica VT1200 vibratome in complete HBSS (100 ml of 10×HBSS without Ca or Mg, 2.5 ml of 1M HEPES buffer at pH 7.4, 30 ml of 1M D-glucose, 10 ml of 100 mM $CaCl2$), 10 ml of 100 mM $MgSO4$, and 4 ml of 1 M $NaHCO3$). Slices with visible forebrain structures were placed in membrane inserts (diameter, 13 mm; pore size, 8 µm; Costar) coated with Poly-L-orthinine and Laminin (Sigma) overnight. They were cultured in a Basal Medium Eagle (39 mL, Life Technologies, #21010046) supplemented with 12.9 ml of complete HBSS, 1.35 ml of 1M D-glucose, 250 µl of 200 mM GlutaMax (Life Technologies) and 5% heat-inactivated horse serum (Life Technologies, 26050070). The slices were imaged using a Leica SP8 confocal microscope.

Electroporation of mouse slices. Coronal slices of mouse embryonic forebrain at E14 were prepared as described above. Sections were transferred into tissue culture dishes containing complete HBSS for ~1 hour, after which CAG-Cav1.2 (WT- or TS-CACNA1C) plasmids were focally co-injected with CAG::GFP at a ratio of 1:0.5 directly into the ganglionic eminence through a glass micropipette. Cav1.2 overexpression constructs were generated by insertion of PCR-amplified WT- and TS-Cav1.2 coding sequences from dihydropyridine-insensitive Cav1.2 constructs47 into pCAGIG (kind gift from C. Cepko through Addgene, plasmid 11159). Slices were then electroporated using two horizontally oriented platinum electrodes powered by a BTX Square Pulse Electroporator, and placed onto cell culture membrane inserts for subsequent live imaging 48 hrs later as described below.

Human Tissue. Human tissue was obtained under a protocol approved by the Research Compliance Office at Stanford University. The tissue was processed using an adapted protocol55. Briefly, GW18 or GW20 frontal brain tissue was embedded in 4% low-melting point agarose in bubbled artificial cerebrospinal fluid (ACSF: 125 mM NaCl, 2.5 mM KCl, 1 mM $MgCl2$, 2 mM $CaCl2$), 1.25 mM $NaH2PO4$, 25 mM $NaHCO_3$, 25 mM D-(+)-Glucose) and either sectioned using a Leica VT1200 Vibratome at 300-500 µm in ice-cold, bubbled ACSF, or cut using the sharp end of a gauge-22 needle to obtain 1-2 mm thick sections. The sections were then placed in tissue culture plates containing culture media (66% BME, 25% Hanks, 5% FBS, 1% N-2, 1% penicillin, streptomycin and glutamine; all from Invitrogen) and 0.66% D-(+)-Glucose (Sigma) and incubated (37° C., 5% $CO2$) with the Dlxi1/2b::eGFP lentivirus for 30 min to 1 hr. Sections were then transferred to cell culture membrane inserts (diameter, 13 mm; pore size, 8 µm; Costar) and incubated in culture media at 37° C., 8% 02, 5% $CO2$ for up to 8 days. Half media changes were performed every other day. After ~5 days in culture, Dlxi1/2b::eGFP+ cells could be detected and were subsequently imaged as described below.

Live imaging and analysis of Dlxi1/2b::eGFP+ cell migration. The migration of Dlxi1/2b::eGFP+ cells was imaged for 8-12 hrs under environmentally controlled conditions (37° C., 5% $CO2$) in intact, fused hSS-hCS using a confocal microscope with a motorized stage (Leica SP8). Fused hSS-hCS were transferred to a well of a 96-well plate (glass-bottom plates, Corning) in 200 µl of NM. Spheroids were incubated in the environmentally controlled chamber for 30-60 min prior to imaging. During a given recording session, up to 8 fused hSS-hCS were imaged at a depth of 50-150 µm depth and a rate of 15-20 min/frame. For pharmacological manipulation, cells were imaged for 12 hrs to record a baseline. Then, the media was carefully removed and new media with small molecules (AMD3100 at 100 nM; nimodipine at 5 µM; or roscovitine at 15 µM) was gently added to the well. The field of view was readjusted to capture the previous region of interest and cells in fused hSS-hCS were imaged for an additional 12 hrs. For imaging of Dlxi1/2b::eGFP+ cells, E17-E18 slices were placed on inserts and infected with Dlxi1/2b::eGFP lentivirus after 24 hrs. The slices were imaged 2 days later using a Leica SP8 confocal microscope (see above). For measuring the branch to soma length ratio of human cells on mouse slices, hSSs infected with Dlxi1/2b::eGFP lentivirus were dissociated and placed on top of E13-14 mouse slices, which were placed on cell culture inserts 8-24 hrs before. The hSS-derived Dlxi1/2b::eGFP+ cells were imaged with the Leica SP8 confocal microscope system at least 48 hrs later. The migration of mouse Dlxi1/2b::eGFP+ cells or Cav1.2-electroporated cells and the migration of human fetal Dlxi1/2b::eGFP-infected cells both imaged using the same setting as described for intact, fused hSS-hCS. Slices were kept on the cell culture inserts during imaging. For quantification of migration of Dlxi1/2b::eGFP+ cells after plating on coverslips, intact hSS were plated on Poly-ornithine/laminin (Sigma) coated glass coverslips (15 mm; Werner). Cells were imaged 7-10 days after using a confocal microscope (Leica SP8) as described above. ImageJ and the Chemotaxis & Migration Tool (Ibidi) were used for the post-acquisition analysis of cell mobility. The StackReg plugin in ImageJ was used to correct for minor drifts during imaging. To estimate the length of individual saltations, Dlxi1/2b::eGFP cells displaying a swelling of the soma were identified, and distance (in µm) to the new position of the soma following nucleokinesis was recorded manually. The time necessary for this movement was used to calculate the speed when mobile. To estimate directness of movement, the x and y coordinates of each cell per frame and time were extracted with the Manual Tracking plugin (ImageJ) and the Chemotaxis & Migration Tool (Ibidi) was used to calculate the Accumulated (A) and Euclidian (E) distances traveled per cell over time. Path directness was calculated as the E/A ratio. Videos were processed using ImageJ and Final Cut Pro X.

Fura-2 calcium imaging of hSS or hCS cultures Dissociated hSS (day 62) or hCS (day 123) derived from control and TS lines were cultured on poly-L-ornithine and laminin (Sigma) coated coverslips for 4-5 days. The cultures were incubated with 1 µM Fura-2 acetoxymethyl ester (Fura-2AM; Invitrogen) for 25 min at 37° C. in NM medium, washed for 5 min and placed in a perfusion chamber on the stage of an inverted fluorescence microscope (TE2000U; Nikon). Cells were then stimulated with high-KCl Tyrode's solution (67 mM KCl, 67 mM NaCl2 mM CaCl2), 1 mM MgCl2, 30 mM glucose and 25 mM HEPES, pH 7.4). Imaging was performed at room temperature (25° C.) on an epifluorescence microscope equipped with an excitation filter wheel and an automated stage. Openlab software (PerkinElmer) was used to collect and quantify time-lapse excitation ratio images. Fluorescence images were analyzed using the IGOR Pro software (WaveMetrics). Residual calcium following high-KCl depolarization was calculated by dividing the plateau calcium level by the peak calcium elevation ((C−A)/(B−A); FIG. 3b).

Fluo-4 calcium imaging in intact hSS. Intact hSS at day 43-52 were incubated with 10 µM Fluo-4 acetoxymethyl ester (Fluo-4AM; Invitrogen) for 30 min in NM media followed by a 15 min wash with NM. A Leica SP8 confocal microscope with a resonant scanner was used for imaging. Spontaneous calcium activity was recorded for 10 min (one frame every 8-10 s) in one 10 µm z-stack plane. Fluorescence intensity (F) was exported as mean gray values in ImageJ. Signal decay was controlled by subtracting the mean fluorescence of the background (Fb). To estimate changes in intracellular calcium, ΔF was computed as (Fcell−Fb)/F0, where F0 represents the minimum F value per cell across the whole 10 min of recording from which Fb was subtracted. A ΔF>1.2 was defined as a spike.

iDISCO. To optically clear fixed fused spheroids, we adapted the iDISCO protocol described by Renier et al56. Briefly, after fixation with 4% PFA for 3 hrs, spheroids were dehydrated with a day-long methanol (MetOH) dilution series (20% to 100% MetOH). Next, they were incubated in 5% H2O2 overnight at 4° C. The following day, they were rehydrated with a reverse MetOH dilution series and incubated overnight in 0.2% Triton-X, 20% DMSO, 0.3 M Glycine/PBS at 37° C. The spheroids were then blocked with 0.2% Triton-X, 10% DMSO, 6% goat serum/PBS at 37° C. for 2 days, followed by a heparin treatment for 2 hrs (PTwH: 0.2% Tween-20, 10 µg/mL Heparin/PBS) to reduce non-specific antibody binding. They were next incubated with a chicken anti-GFP (1:1500; GeneTex: GTX13970) antibody for 2 days in PTwH with 5% DMSO and 3% goat serum at 37° C. After a day-long wash series with PTwH, a secondary antibody diluted in PTwH, 3% Donkey Serum was added for an additional two days at 37° C. After 2 days of PTwH washes, the spheroids were cleared by a three-step tetrahydrofuran (THF) series (80%, 100%, 100% THF/H2O), a 10 min dichloromethane step, and a short incubation in dichloromethane (DBE). The cleared spheroids were stored and imaged in DBE on a Leica SP8 confocal microscope.

Real time quantitative PCR (qPCR). mRNA was isolated using the RNeasy Mini Kit and RNase-Free DNase set (Qiagen), and template cDNA was prepared by reverse transcription using the SuperScript III First-Strand Synthesis SuperMix for qRT-PCR (Life Technologies). Real time qPCR was performed using SYBR GREEN (Roche) on a ViiA7 machine (Applied Biosystems, Life Technologies). Data was processed using the QuantStudio RT-PCR software (Applied Biosystems).

Single cell gene expression (BD Resolve system). To capture transcriptomic information of hiPSCs-derived hCS and hSS (IS) single-cells, we used the BDTM Resolve system (BD Genomics, Menlo Park, CA) as previously reported with modifications. Multiple hCS or hSS at day 105 of differentiation were combined and dissociated enzymatically into single cells, and processed in one batch. Single cell capture was achieved by random distribution of a single cell suspension across >200,000 microwells via a limited dilution approach. Beads with oligonucleotide barcodes were added to saturation such that a bead was paired with a cell in a microwell. Cell lysis buffer was added such that poly-adenylated RNA molecules hybridized to the beads. Beads were collected into a single tube for reverse transcription. Upon cDNA synthesis, each cDNA molecule was tagged on the 5' end (i.e., 3' end of mRNA transcript) with a molecular index and cell label indicating its cell of origin. Whole transcriptome libraries were prepared using the BD Resolve single cell whole transcriptome amplification workflow. Briefly, second strand cDNA was synthesized, followed by ligation of adaptor for universal amplification. Eighteen cycles of PCR were used to amplify the adaptor ligated cDNA products. Sequencing libraries were prepared using random priming PCR of the whole transcriptome amplification products to enrich the 3' end of the transcripts linked with the cell label and molecular indices.

Sequencing libraries were quantified using a High Sensitivity DNA Chip (Agilent) on a Bioanalyzer 2100 and the Qubit High Sensitivity DNA Assay (Thermo Fisher Scientific). 1.5 pM of the library for each sample was loaded onto a NextSeq 500 system and sequenced using High Output sequencing kits (75×2 bp) (Illumina).

The BD Resolve analysis pipeline is used to process sequencing data (fastq files). Cell labels and molecular indices were identified, and gene identity was determined by alignment against the gencode comprehensive hg19 reference. A table containing molecule counts per gene per cell was output. 7,663 and 4,983 cells were identified for hCS and hSS, respectively, with an average number of reads of ~14,800, an average of ~3,710 molecules and ~1,700 number genes detected per cell with an average molecular index coverage (i.e. number of times a molecule was sequenced) of ~2. A total of 34,242 genes were detected across all cells. Cells with mitochondrial gene (with gene symbol starting with MT) content >25%, were discarded retaining 7,126 and 4,712 cells for hCS and hSS (IS), respectively. Pseudogenes were removed. The distribution of reads per single cell is shown in FIG. 61. For visualization and clustering, the data tables of the two libraries were concatenated, and the combined table was further reduced to retain only the most variable genes using the method outlined in Macosko et a/57, yielding 1,102 genes. t-SNE projection of the data was performed using default parameters19. To determine the set of genes contributing to the separation of cell clusters, differential gene expression analysis (DEseq) based on negative binomial distribution58 was conducted to compare gene expression profiles in cells in each cluster versus those in the rest of the data set. Genes are ranked by smallest P values (expressed in terms of −log 10) and the list of significantly over-represented genes with −log 10 (p-value)<10 of each cluster is provided as Table 2. Patterns of expression for the top 25 genes in each cluster is shown in FIG. 6d-k).

Single cell RNA-seq (Smart-seq2). For assessing gene expression in Dlxi1/2b::eGFP+ cells before and after migration, we used a single-cell RNA-Seq assay adapted from the Smart-seq-2 protocol reported by Picelli et al. In short, hSS and hCS that had been fused for ~15 days were separated with a scalpel blade and dissociated independently as described. Single-cells were isolated by FACS into a 96-well PCR plate containing 5 μl of lysis buffer containing 0.04% Triton X-100 (10%, Sigma BioUltra), 0.1 μl recombinant RNase inhibitor (TaKaRa), 1 μl Oligo-dT30VN (10 μM), 1 μl of 10 mM dNTP mix (Fermentas) and nuclease-free H20 for a final volume of 5 μl. A known number of internal RNA control (ERCC) was added to the lysis master mix to estimate the technical variability between the wells of the same plate and between plates. Reverse transcription and PCR amplification were performed using the parameters described by Picelli et al. The quality of the cDNA library was checked using a High-Sensitivity DNA chip (Agilent Bioanalyzer). Libraries were prepared using the Nextera XT library prep kit (96 index primers, Illumina). Because the Nextera XT kit is very sensitive to the concentration of cDNA, we screened pre-amplified cDNA libraries from all plates using the Qubit dsDNA HS Assay kit and used 125 pg cDNA from each positive well to further process the tagmentation and indexing. We used 12 additional PCR cycles to further enrich for pre-amplified tagmented DNA. The quality of the tagmented library was checked using the High-Sensitivity Bioanalyzer chip. The final pooled library was diluted to 2 nM using the elution buffer (Qiagen), and 10 pM was loaded on an Illumina HiSeq 2500 instrument for sequencing. Libraries were sequenced to obtain 50 bp single end reads (TruSeq Rapid kit, Illumina) with 8 additional cycles for indexing. On average, we obtained 2 million pass filter reads per single cell (FIG. 11c). We considered a gene expressed if there were at least 10 reads detected for that gene. Cells that expressed more than 1,000 genes and <10% mitochondrial RNAs were kept for analysis. To avoid bias during FACS from RNA contamination from the glutamatergic neurons on the hCS side of the fused hSS-hCS, we analyzed STMN2+ cells that did not expressed SLC17A6 or SLC17A7. To control for technical noise, we used a quantitative statistical analysis60 to detect biological variable genes and used them for further analysis. To cluster and visualize the cells, we used the tSNE method in the computational software package Seurat.

Array tomography (AT). AT was used to collect high-resolution images of synapses within neural spheroids using previously published protocols. Briefly, fused hSS-hCS were fixed in 4% paraformaldehyde, 2.5% sucrose in phosphate buffered saline. To preserve GFP fluorescence, the tissue was dehydrated up to 70% alcohol only, with processing through 50% ethanol, 70% ethanol, 1:3 70% ethanol:LR White Resin (LRW, medium grade, SPI supplies), and LRW overnight before embedding in LRW. The embedded tissue was sectioned into ribbons of 70 nm thick sections (~30 sections/ribbon) and each ribbon was immunostained in 2-3 rounds of staining with the antibodies eluted after each round. The following primary antibodies were used for immunostaining: anti-GFP (chicken, 1:200; Genetex: 13970, 1:200), anti-SYN1 (rabbit, Cell Signalling: 5297S, 1:500), anti-PSD95 (rabbit, Cell Signalling: 3450S), anti-VGUT1 (guinea pig, 1:5000; Millipore: AB5905), anti-Gephyrin (mouse, 1:100; BD Biosciences: 612632), anti-VGAT (guinea pig, 1:200; Synaptic Systems 131004), anti-VGAT (mouse, 1:200; Synaptic Systems: 131011), anti-GFAP (chicken, 1:300; Ayes), anti-MAP2 (guinea pig, 1:1000; Synaptic Systems: 188004). Sections were visualized on a Zeiss Axio Imager.Z1 upright fluorescence microscope using AxioVision software (rel 4.7, Zeiss). Images were processed and registered using FIJI/ImageJ with standard and custom plugins.

Electrophysiology. Sections of hCS (day 96-141) or fused hSS-hCS (29-53 daf) for physiological recordings were obtained using an approach we previously described16. Briefly, spheroids were incubated in bicarbonate buffered artificial cerebrospinal fluid (ACSF) at 23° C. and equilibrated with a mixture of 95% 02 and 5% CO2. The ACSF solution contained: 126 mM NaCl, 26 mM $NaHCO_3$, 10 mM glucose, 2.5 mM KCl, 1.25 mM NaH2PO4, 1 mM MgSO4, and 2 mM CaCl2). Slicing was performed using a Leica VT1200 vibratome. Immediately after sectioning, slices were moved to a circulation chamber containing ACSF at 32° C.

For patch-clamp recording, cells were identified by the presence of a fluorescent reporter using an upright Axoscop II microscope (Zeiss). Recording electrodes of borosilicate glass had a resistance of 4-6 MΩ when filled with internal solution. A low Cl− internal solution was used to distinguish between EPSCs and IPSCs containing: 145 mM K+ gluconate, 0.1 mM CaCl2), 2.5 mM MgCl2, 10 mM HEPES, 0.2 mM EGTA, 4 mM Na+ phosphocreatine. Cl− reversal was calculated to be at −91 mV according to the Nernst equation. A high Cl− internal solution was used to measure EPSCs in a subset of unfused hSS containing: 135 mM CsCl, 10 mM HEPES, 10 mM EGTA, 3 mM MgATP, 0.3 mM GTP. The Cl− reversal potential was calculated to be 0 mV according to the Nernst equation. IPSCs were blocked by application of the GABAA receptor antagonist gabazine (10 μM, Abcam), which was added to superfused ACSF. EPSCs were blocked by application of the glutamate receptor antagonist kynurenic acid (1 mM, Abcam), which was added to superfused ACSF. Electrical simulation was delivered using a bipolar tungsten electrode (FHS) placed 200-400 μM away from a recorded neuron. Stimulations were delivered to slices for 0.1 ms at 300 μV and separated by at least 10 s. Inward EPSCs and outward IPSPs were recorded by filling the patch pipette with a low chloride internal solution (ECI-=−90 mV) and holding the cell at −40 mV, which is the midpoint between ECI− and EK+/Na+. Data were collected using a 1550 A digitizer (Molecular Devices), a 700B patch-clamp amplifier (Molecular Devices) and acquired with the pClamp 10.6 software (Molecular Devices). Recordings were filtered at 10 kHz. Synaptic recordings were analyzed using custom software developed by J. R. H. (Wdetecta). Action potentials were analyzed using custom MATLAB (MathWorks) programs. IPSCs and EPSCs were detected based on their direction and shape. We calculated the first time derivative of the current recording and set a detection threshold that was above the noise for each trace. Detected responses were then evaluated to confirm the detection accuracy.

Gene expression accession codes. Gene expression data are available in the Gene Expression Omnibus under accession codes: GSE93811 (BDTM Resolve) and GSE93321 (Smartseq-2).

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. An in vitro generated integrated human forebrain structure produced by the method,
   (A) inducing in a pluripotent stem cell suspension culture a neural fate by culturing pluripotent stem cells in medium comprising an effective dose of an inhibitor of bone morphogenetic protein (BMP) and an inhibitor of TGFβ to derive spheroids of neural progenitor cells;
   (B) differentiating neural progenitor cells in a spheroid of step A into cortical spheroids (hCS) by the steps comprising:
      (i) culturing the spheroid in neural medium comprising an effective dose of fibroblast growth factor 2 (FGF2) and epidermal growth factor (EGF) for a period of from 1 to 4 weeks;
      (ii) moving the spheroid to medium comprising an effective dose of brain-derived neurotrophic factor (BDNF) and neurotrophin-3 (NT3) for a period of from 4 to 7 weeks to generate hCS;
   (C) differentiating neural progenitor cells in a spheroid of step A to subpallial spheroids (hSS) by the steps comprising:
      (i) culturing a spheroid of step A in the presence of medium comprising an effective dose of a Wnt inhibitor and Agonist of Smoothened for a period of from 7 to 24 days;
      (ii) culturing the spheroid in neural medium comprising an effective dose of fibroblast growth factor 2 (FGF2) and epidermal growth factor (EGF) for a period of from 1 to 4 weeks;
      (iii) moving the spheroid to medium comprising an effective dose of brain-derived neurotrophic factor (BDNF) and neurotrophin-3 (NT3) for a period of from 4 to 7 weeks to generate hSS;
   (D) culturing the hCS and hSS in close proximity for an extended period of time in neural medium to provide an integrated forebrain structure called an assembled organoid comprising human GABAergic interneurons synaptically integrated with human glutamatergic neurons.

2. The integrated human forebrain structure of claim 1, wherein the pluripotent stem cells or derived neural cells comprise at least genetic variant or genetic mutation associated with a neurologic or psychiatric disorder; wherein the disorder is selected from the group consisting of Schizophrenia, Autism Spectrum Disorders, Huntington's disease, Parkinson's disease, Alzheimer's disease, Dementia, Bipolar Disease, Angelman's disease, Rett's disease, Tuberous sclerosis, Epilepsy, Trisomy 21, Down Syndrome, and Fragile X syndrome.

* * * * *

```
                              SEQUENCE LISTING

<160> NUMBER OF SEQ ID NOS: 68

<210> SEQ ID NO 1
<211> LENGTH: 19
<212> TYPE: DNA
<213> ORGANISM: Artificial sequence
<220> FEATURE:
<223> OTHER INFORMATION: synthetic sequence

<400> SEQUENCE: 1
tcttcgcccg aactgatgc                                                  19

<210> SEQ ID NO 2
<211> LENGTH: 23
<212> TYPE: DNA
<213> ORGANISM: Artificial sequence
<220> FEATURE:
<223> OTHER INFORMATION: synthetic sequence

<400> SEQUENCE: 2
tatgagcctc gaatccacat agt                                             23

<210> SEQ ID NO 3
<211> LENGTH: 23
<212> TYPE: DNA
<213> ORGANISM: Artificial sequence
<220> FEATURE:
<223> OTHER INFORMATION: synthetic sequence

<400> SEQUENCE: 3
agggaatcaa aatgtgtggg aaa                                             23

<210> SEQ ID NO 4
<211> LENGTH: 20
<212> TYPE: DNA
<213> ORGANISM: Artificial sequence
<220> FEATURE:
<223> OTHER INFORMATION: synthetic sequence

<400> SEQUENCE: 4
tttgcagaca agccaggatg                                                 20

<210> SEQ ID NO 5
<211> LENGTH: 20
<212> TYPE: DNA
<213> ORGANISM: Artificial sequence
<220> FEATURE:
<223> OTHER INFORMATION: synthetic sequence

<400> SEQUENCE: 5
acatgattga gcgctgcatc                                                 20
```

```
<210> SEQ ID NO 6
<211> LENGTH: 20
<212> TYPE: DNA
<213> ORGANISM: Artificial sequence
<220> FEATURE:
<223> OTHER INFORMATION: synthetic sequence

<400> SEQUENCE: 6
tgttggctga aaaggtggtc                                               20

<210> SEQ ID NO 7
<211> LENGTH: 20
<212> TYPE: DNA
<213> ORGANISM: Artificial sequence
<220> FEATURE:
<223> OTHER INFORMATION: synthetic sequence

<400> SEQUENCE: 7
atcttgaacc tggccattgc                                               20

<210> SEQ ID NO 8
<211> LENGTH: 20
<212> TYPE: DNA
<213> ORGANISM: Artificial sequence
<220> FEATURE:
<223> OTHER INFORMATION: synthetic sequence

<400> SEQUENCE: 8
atcctcaccc tgttttgtgc                                               20

<210> SEQ ID NO 9
<211> LENGTH: 20
<212> TYPE: DNA
<213> ORGANISM: Artificial sequence
<220> FEATURE:
<223> OTHER INFORMATION: synthetic sequence

<400> SEQUENCE: 9
atgcactgtt tacactcggc                                               20

<210> SEQ ID NO 10
<211> LENGTH: 20
<212> TYPE: DNA
<213> ORGANISM: Artificial sequence
<220> FEATURE:
<223> OTHER INFORMATION: synthetic sequence

<400> SEQUENCE: 10
acgggaagcc aagaaagtc                                                20

<210> SEQ ID NO 11
<211> LENGTH: 20
<212> TYPE: DNA
<213> ORGANISM: Artificial sequence
<220> FEATURE:
<223> OTHER INFORMATION: synthetic sequence

<400> SEQUENCE: 11
ttccaagctc cgttccagac                                               20

<210> SEQ ID NO 12
<211> LENGTH: 19
<212> TYPE: DNA
<213> ORGANISM: Artificial sequence
<220> FEATURE:
<223> OTHER INFORMATION: synthetic sequence
```

-continued

<400> SEQUENCE: 12
cgcaggtgaa ggtgtggtt                                                    19

<210> SEQ ID NO 13
<211> LENGTH: 20
<212> TYPE: DNA
<213> ORGANISM: Artificial sequence
<220> FEATURE:
<223> OTHER INFORMATION: synthetic sequence

<400> SEQUENCE: 13
aacaatgtga cggcagatgc                                                   20

<210> SEQ ID NO 14
<211> LENGTH: 20
<212> TYPE: DNA
<213> ORGANISM: Artificial sequence
<220> FEATURE:
<223> OTHER INFORMATION: synthetic sequence

<400> SEQUENCE: 14
aacctgtgtt gcgcaaatgc                                                   20

<210> SEQ ID NO 15
<211> LENGTH: 20
<212> TYPE: DNA
<213> ORGANISM: Artificial sequence
<220> FEATURE:
<223> OTHER INFORMATION: synthetic sequence

<400> SEQUENCE: 15
atgcaaccag atgtgtgcag                                                   20

<210> SEQ ID NO 16
<211> LENGTH: 23
<212> TYPE: DNA
<213> ORGANISM: Artificial sequence
<220> FEATURE:
<223> OTHER INFORMATION: synthetic sequence

<400> SEQUENCE: 16
catgagaagt atgacaacag cct                                               23

<210> SEQ ID NO 17
<211> LENGTH: 20
<212> TYPE: DNA
<213> ORGANISM: Artificial sequence
<220> FEATURE:
<223> OTHER INFORMATION: synthetic sequence

<400> SEQUENCE: 17
atgaaactga ctgccgttgg                                                   20

<210> SEQ ID NO 18
<211> LENGTH: 20
<212> TYPE: DNA
<213> ORGANISM: Artificial sequence
<220> FEATURE:
<223> OTHER INFORMATION: synthetic sequence

<400> SEQUENCE: 18
tcctcgtttt cagctttggc                                                   20

<210> SEQ ID NO 19

```
<211> LENGTH: 20
<212> TYPE: DNA
<213> ORGANISM: Artificial sequence
<220> FEATURE:
<223> OTHER INFORMATION: synthetic sequence

<400> SEQUENCE: 19
tgagagtcag gtacagtgcg                                              20

<210> SEQ ID NO 20
<211> LENGTH: 20
<212> TYPE: DNA
<213> ORGANISM: Artificial sequence
<220> FEATURE:
<223> OTHER INFORMATION: synthetic sequence

<400> SEQUENCE: 20
aaacccacgc aaacacacac                                              20

<210> SEQ ID NO 21
<211> LENGTH: 20
<212> TYPE: DNA
<213> ORGANISM: Artificial sequence
<220> FEATURE:
<223> OTHER INFORMATION: synthetic sequence

<400> SEQUENCE: 21
tggccggatg catttttgag                                              20

<210> SEQ ID NO 22
<211> LENGTH: 20
<212> TYPE: DNA
<213> ORGANISM: Artificial sequence
<220> FEATURE:
<223> OTHER INFORMATION: synthetic sequence

<400> SEQUENCE: 22
acagctggag tggcaaaaag                                              20

<210> SEQ ID NO 23
<211> LENGTH: 19
<212> TYPE: DNA
<213> ORGANISM: Artificial sequence
<220> FEATURE:
<223> OTHER INFORMATION: synthetic sequence

<400> SEQUENCE: 23
agcacacgac tccgttctc                                               19

<210> SEQ ID NO 24
<211> LENGTH: 20
<212> TYPE: DNA
<213> ORGANISM: Artificial sequence
<220> FEATURE:
<223> OTHER INFORMATION: synthetic sequence

<400> SEQUENCE: 24
agcacaaacc ctcgaacttg                                              20

<210> SEQ ID NO 25
<211> LENGTH: 20
<212> TYPE: DNA
<213> ORGANISM: Artificial sequence
<220> FEATURE:
<223> OTHER INFORMATION: synthetic sequence

<400> SEQUENCE: 25
```

```
cgctgcgaca ctacatcaac                                               20

<210> SEQ ID NO 26
<211> LENGTH: 23
<212> TYPE: DNA
<213> ORGANISM: Artificial sequence
<220> FEATURE:
<223> OTHER INFORMATION: synthetic sequence

<400> SEQUENCE: 26
ccccagggcc ccattttggt acc                                           23

<210> SEQ ID NO 27
<211> LENGTH: 20
<212> TYPE: DNA
<213> ORGANISM: Artificial sequence
<220> FEATURE:
<223> OTHER INFORMATION: synthetic sequence

<400> SEQUENCE: 27
ggacaagcta ggaggcagtg                                               20

<210> SEQ ID NO 28
<211> LENGTH: 22
<212> TYPE: DNA
<213> ORGANISM: Artificial sequence
<220> FEATURE:
<223> OTHER INFORMATION: synthetic sequence

<400> SEQUENCE: 28
ggacaaaagt ggcttcatcg ag                                            22

<210> SEQ ID NO 29
<211> LENGTH: 19
<212> TYPE: DNA
<213> ORGANISM: Artificial sequence
<220> FEATURE:
<223> OTHER INFORMATION: synthetic sequence

<400> SEQUENCE: 29
ggccatcctg gggtttacc                                                19

<210> SEQ ID NO 30
<211> LENGTH: 20
<212> TYPE: DNA
<213> ORGANISM: Artificial sequence
<220> FEATURE:
<223> OTHER INFORMATION: synthetic sequence

<400> SEQUENCE: 30
tttttgacgg cttgctggtg                                               20

<210> SEQ ID NO 31
<211> LENGTH: 20
<212> TYPE: DNA
<213> ORGANISM: Artificial sequence
<220> FEATURE:
<223> OTHER INFORMATION: synthetic sequence

<400> SEQUENCE: 31
agcagaagac gcattgcttc                                               20

<210> SEQ ID NO 32
<211> LENGTH: 20
<212> TYPE: DNA
```

```
<213> ORGANISM: Artificial sequence
<220> FEATURE:
<223> OTHER INFORMATION: synthetic sequence

<400> SEQUENCE: 32
tgcgcaagtt gatgaactgc                                               20

<210> SEQ ID NO 33
<211> LENGTH: 19
<212> TYPE: DNA
<213> ORGANISM: Artificial sequence
<220> FEATURE:
<223> OTHER INFORMATION: synthetic sequence

<400> SEQUENCE: 33
gtggaccgca cggaatttg                                                19

<210> SEQ ID NO 34
<211> LENGTH: 24
<212> TYPE: DNA
<213> ORGANISM: Artificial sequence
<220> FEATURE:
<223> OTHER INFORMATION: synthetic sequence

<400> SEQUENCE: 34
ttcacatgtc ccagcactac caga                                          24

<210> SEQ ID NO 35
<211> LENGTH: 21
<212> TYPE: DNA
<213> ORGANISM: Artificial sequence
<220> FEATURE:
<223> OTHER INFORMATION: synthetic sequence

<400> SEQUENCE: 35
caaagcccag gttgaccaac t                                             21

<210> SEQ ID NO 36
<211> LENGTH: 22
<212> TYPE: DNA
<213> ORGANISM: Artificial sequence
<220> FEATURE:
<223> OTHER INFORMATION: synthetic sequence

<400> SEQUENCE: 36
cctcgttctg ataagcagtc ac                                            22

<210> SEQ ID NO 37
<211> LENGTH: 23
<212> TYPE: DNA
<213> ORGANISM: Artificial sequence
<220> FEATURE:
<223> OTHER INFORMATION: synthetic sequence

<400> SEQUENCE: 37
tccttcagta aagcatccag ttc                                           23

<210> SEQ ID NO 38
<211> LENGTH: 20
<212> TYPE: DNA
<213> ORGANISM: Artificial sequence
<220> FEATURE:
<223> OTHER INFORMATION: synthetic sequence

<400> SEQUENCE: 38
tgtttcaccg tgaactgcac                                               20
```

<210> SEQ ID NO 39
<211> LENGTH: 20
<212> TYPE: DNA
<213> ORGANISM: Artificial sequence
<220> FEATURE:
<223> OTHER INFORMATION: synthetic sequence

<400> SEQUENCE: 39
acttgtcgta ccagcgattg                                                     20

<210> SEQ ID NO 40
<211> LENGTH: 20
<212> TYPE: DNA
<213> ORGANISM: Artificial sequence
<220> FEATURE:
<223> OTHER INFORMATION: synthetic sequence

<400> SEQUENCE: 40
aacacaacca cccacaagtc                                                     20

<210> SEQ ID NO 41
<211> LENGTH: 20
<212> TYPE: DNA
<213> ORGANISM: Artificial sequence
<220> FEATURE:
<223> OTHER INFORMATION: synthetic sequence

<400> SEQUENCE: 41
tgtgtgactt tgcacgtgag                                                     20

<210> SEQ ID NO 42
<211> LENGTH: 20
<212> TYPE: DNA
<213> ORGANISM: Artificial sequence
<220> FEATURE:
<223> OTHER INFORMATION: synthetic sequence

<400> SEQUENCE: 42
aggtgggcaa acaagcaaac                                                     20

<210> SEQ ID NO 43
<211> LENGTH: 21
<212> TYPE: DNA
<213> ORGANISM: Artificial sequence
<220> FEATURE:
<223> OTHER INFORMATION: synthetic sequence

<400> SEQUENCE: 43
gactgcaccg aactgatgta g                                                   21

<210> SEQ ID NO 44
<211> LENGTH: 20
<212> TYPE: DNA
<213> ORGANISM: Artificial sequence
<220> FEATURE:
<223> OTHER INFORMATION: synthetic sequence

<400> SEQUENCE: 44
ttttggaaac gccgctgaag                                                     20

<210> SEQ ID NO 45
<211> LENGTH: 21
<212> TYPE: DNA
<213> ORGANISM: Artificial sequence
<220> FEATURE:

<223> OTHER INFORMATION: synthetic sequence

<400> SEQUENCE: 45
gaatcggtag ctgaagactc g                                              21

<210> SEQ ID NO 46
<211> LENGTH: 19
<212> TYPE: DNA
<213> ORGANISM: Artificial sequence
<220> FEATURE:
<223> OTHER INFORMATION: synthetic sequence

<400> SEQUENCE: 46
tccagcttct gccgtttgt                                                 19

<210> SEQ ID NO 47
<211> LENGTH: 20
<212> TYPE: DNA
<213> ORGANISM: Artificial sequence
<220> FEATURE:
<223> OTHER INFORMATION: synthetic sequence

<400> SEQUENCE: 47
ttcatgcagg caaagcagtc                                                20

<210> SEQ ID NO 48
<211> LENGTH: 20
<212> TYPE: DNA
<213> ORGANISM: Artificial sequence
<220> FEATURE:
<223> OTHER INFORMATION: synthetic sequence

<400> SEQUENCE: 48
aaacacgggc atatgaccac                                                20

<210> SEQ ID NO 49
<211> LENGTH: 20
<212> TYPE: DNA
<213> ORGANISM: Artificial sequence
<220> FEATURE:
<223> OTHER INFORMATION: synthetic sequence

<400> SEQUENCE: 49
tgccctttgc tttccacatc                                                20

<210> SEQ ID NO 50
<211> LENGTH: 22
<212> TYPE: DNA
<213> ORGANISM: Artificial sequence
<220> FEATURE:
<223> OTHER INFORMATION: synthetic sequence

<400> SEQUENCE: 50
agtccttcca cgataccaaa gt                                             22

<210> SEQ ID NO 51
<211> LENGTH: 20
<212> TYPE: DNA
<213> ORGANISM: Artificial sequence
<220> FEATURE:
<223> OTHER INFORMATION: synthetic sequence

<400> SEQUENCE: 51
atgtgctcgc tgttgatgtg                                                20

```
<210> SEQ ID NO 52
<211> LENGTH: 20
<212> TYPE: DNA
<213> ORGANISM: Artificial sequence
<220> FEATURE:
<223> OTHER INFORMATION: synthetic sequence

<400> SEQUENCE: 52
tcatttgtta gcgggtgtcg                                               20

<210> SEQ ID NO 53
<211> LENGTH: 21
<212> TYPE: DNA
<213> ORGANISM: Artificial sequence
<220> FEATURE:
<223> OTHER INFORMATION: synthetic sequence

<400> SEQUENCE: 53
gcccatccat atcggctttg a                                             21

<210> SEQ ID NO 54
<211> LENGTH: 22
<212> TYPE: DNA
<213> ORGANISM: Artificial sequence
<220> FEATURE:
<223> OTHER INFORMATION: synthetic sequence

<400> SEQUENCE: 54
tctctttctg acaaggcagg ac                                            22

<210> SEQ ID NO 55
<211> LENGTH: 20
<212> TYPE: DNA
<213> ORGANISM: Artificial sequence
<220> FEATURE:
<223> OTHER INFORMATION: synthetic sequence

<400> SEQUENCE: 55
aagcaccatg cggttcatac                                               20

<210> SEQ ID NO 56
<211> LENGTH: 20
<212> TYPE: DNA
<213> ORGANISM: Artificial sequence
<220> FEATURE:
<223> OTHER INFORMATION: synthetic sequence

<400> SEQUENCE: 56
aaattgtcaa gcccccgaac                                               20

<210> SEQ ID NO 57
<211> LENGTH: 22
<212> TYPE: DNA
<213> ORGANISM: Artificial sequence
<220> FEATURE:
<223> OTHER INFORMATION: synthetic sequence

<400> SEQUENCE: 57
gcccactttc ttgtagcttt cc                                            22

<210> SEQ ID NO 58
<211> LENGTH: 22
<212> TYPE: DNA
<213> ORGANISM: Artificial sequence
<220> FEATURE:
<223> OTHER INFORMATION: synthetic sequence
```

```
<400> SEQUENCE: 58
cccccggatt ctgcaaaaat ag                                              22

<210> SEQ ID NO 59
<211> LENGTH: 20
<212> TYPE: DNA
<213> ORGANISM: Artificial sequence
<220> FEATURE:
<223> OTHER INFORMATION: synthetic sequence

<400> SEQUENCE: 59
cagggtcttc aagccgagtt                                                 20

<210> SEQ ID NO 60
<211> LENGTH: 26
<212> TYPE: DNA
<213> ORGANISM: Artificial sequence
<220> FEATURE:
<223> OTHER INFORMATION: synthetic sequence

<400> SEQUENCE: 60
acctcagttt gaatgcatgg gagagc                                          26

<210> SEQ ID NO 61
<211> LENGTH: 20
<212> TYPE: DNA
<213> ORGANISM: Artificial sequence
<220> FEATURE:
<223> OTHER INFORMATION: synthetic sequence

<400> SEQUENCE: 61
atggcgatgt tgaggtcgtg                                                 20

<210> SEQ ID NO 62
<211> LENGTH: 20
<212> TYPE: DNA
<213> ORGANISM: Artificial sequence
<220> FEATURE:
<223> OTHER INFORMATION: synthetic sequence

<400> SEQUENCE: 62
tcgtcaaccc caattttgcc                                                 20

<210> SEQ ID NO 63
<211> LENGTH: 19
<212> TYPE: DNA
<213> ORGANISM: Artificial sequence
<220> FEATURE:
<223> OTHER INFORMATION: synthetic sequence

<400> SEQUENCE: 63
ggtcgagggg cttcgtact                                                  19

<210> SEQ ID NO 64
<211> LENGTH: 20
<212> TYPE: DNA
<213> ORGANISM: Artificial sequence
<220> FEATURE:
<223> OTHER INFORMATION: synthetic sequence

<400> SEQUENCE: 64
tcccaaatcc gaaagcactg                                                 20

<210> SEQ ID NO 65
<211> LENGTH: 20
```

```
<212> TYPE: DNA
<213> ORGANISM: Artificial sequence
<220> FEATURE:
<223> OTHER INFORMATION: synthetic sequence

<400> SEQUENCE: 65
accagttgcc tacttgtgtg                                            20

<210> SEQ ID NO 66
<211> LENGTH: 21
<212> TYPE: DNA
<213> ORGANISM: Artificial sequence
<220> FEATURE:
<223> OTHER INFORMATION: synthetic sequence

<400> SEQUENCE: 66
tcacgttgaa cccagagatg g                                          21

<210> SEQ ID NO 67
<211> LENGTH: 20
<212> TYPE: DNA
<213> ORGANISM: Artificial sequence
<220> FEATURE:
<223> OTHER INFORMATION: synthetic sequence

<400> SEQUENCE: 67
ggagattcac accggagtca                                            20

<210> SEQ ID NO 68
<211> LENGTH: 26
<212> TYPE: DNA
<213> ORGANISM: Artificial sequence
<220> FEATURE:
<223> OTHER INFORMATION: synthetic sequence

<400> SEQUENCE: 68
tcacatgtgt gagagggca gtgtgc                                      26
```